US011766441B2

(12) United States Patent
Parikh et al.

(10) Patent No.: US 11,766,441 B2
(45) Date of Patent: *Sep. 26, 2023

(54) ORAL LIQUID COMPOSITIONS INCLUDING CHLORPROMAZINE

(71) Applicant: GENUS LIFESCIENCES INC., Allentown, PA (US)

(72) Inventors: Vaishnavi Parikh, Sellersville, PA (US); Suhas Gumaste, Bethlehem, PA (US)

(73) Assignee: GENUS LIFESCIENCES INC., Allentown, PA (US)

( * ) Notice: Subject to any disclaimer, the term of this patent is extended or adjusted under 35 U.S.C. 154(b) by 179 days.

This patent is subject to a terminal disclaimer.

(21) Appl. No.: 17/225,469

(22) Filed: Apr. 8, 2021

(65) Prior Publication Data

US 2022/0096488 A1    Mar. 31, 2022

Related U.S. Application Data

(63) Continuation of application No. 17/036,121, filed on Sep. 29, 2020, now Pat. No. 11,071,739.

(51) Int. Cl.
*A61K 31/5415* (2006.01)
*A61J 1/14* (2023.01)
*A61K 9/00* (2006.01)

(52) U.S. Cl.
CPC ......... *A61K 31/5415* (2013.01); *A61J 1/1468* (2015.05); *A61K 9/0053* (2013.01)

(58) Field of Classification Search
CPC .................................................. A61K 31/5415
See application file for complete search history.

(56) References Cited

U.S. PATENT DOCUMENTS

| | | | |
|---|---|---|---|
| 3,777,019 A | 12/1973 | Levin | |
| 4,036,227 A | 7/1977 | Zaffaroni et al. | |
| 4,175,119 A | 11/1979 | Porter | |
| 4,952,402 A | 8/1990 | Sparks et al. | |
| 5,133,374 A | 7/1992 | Paradissis et al. | |
| 5,262,171 A | 11/1993 | Login et al. | |
| 5,288,503 A | 2/1994 | Wood et al. | |
| 5,602,150 A | 2/1997 | Lidsky | |
| 5,785,976 A | 7/1998 | Westesen et al. | |
| 5,885,486 A | 3/1999 | Westesen et al. | |
| 6,207,178 B1 | 3/2001 | Westesen et al. | |
| 6,372,254 B1 | 4/2002 | Ting et al. | |
| 6,383,471 B1 | 5/2002 | Chen et al. | |
| 6,566,389 B1 | 5/2003 | Zisapel et al. | |
| 6,602,521 B1 | 8/2003 | Ting et al. | |
| 6,730,321 B2 | 5/2004 | Ting et al. | |
| 6,872,405 B2 | 3/2005 | Takaishi et al. | |
| 6,977,070 B2 | 12/2005 | Dugger, III | |
| 7,122,201 B2 | 10/2006 | Yu et al. | |
| 7,601,337 B2 | 10/2009 | Rabinowitz et al. | |
| 7,713,551 B2 | 5/2010 | McGurk et al. | |
| 7,799,782 B2 | 9/2010 | Munson et al. | |
| 7,879,360 B2 | 2/2011 | Cunningham et al. | |
| 8,242,110 B2 | 8/2012 | Deregnaucourt et al. | |
| 8,268,352 B2 | 8/2012 | Vaya et al. | |
| 8,618,130 B2 | 12/2013 | Weiner et al. | |
| 8,921,393 B2 | 12/2014 | Weiner et al. | |
| 9,254,268 B2 | 2/2016 | Temtsin Krayz et al. | |
| 9,415,030 B2 | 8/2016 | Cleveland | |
| 9,421,179 B2 | 8/2016 | Fogel et al. | |
| 9,757,371 B2 | 9/2017 | Haswani et al. | |
| 11,071,739 B1 * | 7/2021 | Parikh | A61K 47/183 |
| 11,426,413 B2 * | 8/2022 | Parikh | A61K 9/0053 |
| 2003/0175354 A1 | 9/2003 | Drizen et al. | |
| 2007/0148100 A1 | 6/2007 | Jenkins et al. | |
| 2012/0309704 A1 | 12/2012 | Arcangeli et al. | |
| 2013/0217777 A1 | 8/2013 | Kirkorian | |
| 2014/0056998 A1 | 2/2014 | Cleiland et al. | |
| 2014/0193517 A1 | 7/2014 | Agarwal et al. | |
| 2015/0250742 A1 | 9/2015 | Nhamias et al. | |
| 2016/0128944 A1 | 5/2016 | Chawrai et al. | |
| 2016/0228379 A1 | 8/2016 | Kumar et al. | |
| 2016/0271070 A1 | 9/2016 | Singh et al. | |
| 2016/0317388 A1 | 11/2016 | Bhargava et al. | |
| 2017/0119627 A1 | 5/2017 | Bhargava et al. | |
| 2017/0173037 A1 | 6/2017 | Bosse et al. | |
| 2017/0189443 A1 | 7/2017 | Parsons et al. | |
| 2017/0216272 A1 | 8/2017 | Sinclair et al. | |
| 2017/0281652 A1 | 10/2017 | Altschul et al. | |
| 2017/0290781 A1 | 10/2017 | Mo et al. | |
| 2022/0096489 A1 | 3/2022 | Parikh et al. | |

OTHER PUBLICATIONS

Gadalla et al., CAS: 99: 163958, 1983.*
Belozerova et al. CAS: 73: 7156, 1969.*
Degert et al. CAS: 131:23524, 1999.*
Physician's Desk Reference, Thorazine, copyright 1999, Smithkline Beecham, pp. 3101-3104.
Center for Drug Evaluation and Research, Application No. 40-231 for Chlorpromazine HCI, Oral Concentrate, Bioequivalency Review(s), 2000, 5 pages.
Center for Drug Evaluation and Research, Application No. 40-231 for Chlorpromazine HCI, Oral Concentrate, Chemistry Review(s), 2000, 6 pages.
Center for Drug Evaluation and Research, Application No. 40-231 for Chlorpromazine HCI, Oral Concentrate, Correspondence, 2000, 11 pages.
Center for Drug Evaluation and Research, Application No. 40-231 for Chlorpromazine HCI, Oral Concentrate, Draft Final Printed Labeling, 2000, 7 pages.
Center for Drug Evaluation and Research, Application No. 40-231 for Chlorpromazine HCI, Oral Concentrate, Administrative Documents, 2000, 3 pages.
Center for Drug Evaluation and Research, Application No. 40-231 for Chlorpromazine HCI, Oral Concentrate, Dec. 30, 1999 Approval Letter from the Office of Generic Drugs, Center for Drug Evaluation and Research to Pharmaceutical Associates, Inc., available 2000, 2 pages.

(Continued)

*Primary Examiner* — Rei Tsang Shiao
(74) *Attorney, Agent, or Firm* — K&L Gates LLP

(57) ABSTRACT

Stable oral liquid compositions including chlorpromazine or a pharmaceutically acceptable salt or solvate of chlorpromazine, and methods of administering the compositions, are disclosed.

24 Claims, 6 Drawing Sheets

(56) References Cited

OTHER PUBLICATIONS

Center for Drug Evaluation and Research, Application No. 40-231 for Chlorpromazine HCI, Oral Concentrate, Dec. 30, 1999 Approval Letter from the Office of Generic Drugs, Center for Drug Evaluation and Research to Pharmaceutical Associates, Inc., available 2000, 3 pages.
Center for Drug Evaluation and Research, Application No. 40-224 for Chlorpromazine HCI, Oral Concentrate, Draft Final Printed Labeling, 1999, 7 pages.
Center for Drug Evaluation and Research, Application No. 40-224 for Chlorpromazine HCI, Oral Concentrate, Chemistry Review(s), 1998. 6 pages.
Center for Drug Evaluation and Research, Application No. 40-224 for Chlorpromazine HCI, Oral Concentrate, Bioequivalency Review(s), 1999, 5 pages.
Center for Drug Evaluation and Research, Application No. 40-224 for Chlorpromazine HCI, Oral Concentrate, Correspondence, 1999, 13 pages.
Center for Drug Evaluation and Research, Application No. 40-224 for Chlorpromazine HCI, Oral Concentrate, Administrative Documents, 1999, 3 pages.
Center for Drug Evaluation and Research, Application No. 40-224 for Chlorpromazine HCI, Oral Concentrate, Jan. 26, 1999 Approval Letter from the Office of Generic Drugs, Center for Drug Evaluation and Research to Pharmaceutical Associates, Inc., available 1999, 2 pages.
Center for Drug Evaluation and Research, Application No. 40-224 for Chlorpromazine HCI, Oral Concentrate, Jan. 26, 1999 Approval Letter from the Office of Generic Drugs, Center for Drug Evaluation and Research to Pharmaceutical Associates, Inc., available 1999, 3 pages.
Guidance for Industry Q3B(R2) Impurities in New Drug Products, U.S. Department of Health and Human Services, Food and Drug Administration, Center for Drug Evaluation and Research (CDER), Center for Biologies Evaluation and Research (CBER), 2066, Revision 2, accessed from https://www.fda.gov/drugs/guidances-drugs/international-council-harmonisation-quality, 18 pages.
NCT02943213, Assessment of Intra-subject Variability in the Bioavailability of Chlorpromazine Hydrochloride, Study Details and Tabular View, ClinicalTrials.gov, Oct. 2016, 22 pages.
NCT02943213, Assessment of Intra-subject Variability in the Bioavailability of Chlorpromazine Hydrochloride, Study Results, ClinicalTrials.gov, Oct. 2017, 20 pages.
NCT03021486, Haloperidol With or Without Chlorpromazine in Treating Delirium in Patients With Advanced, Metastatic, or Recurrent Cancer, Study Details and Tabular View, ClinicalTrials.gov, Jan. 2017, 21 pages.
NCT00169039, Clozapine Versus Chlorpromazine for Treatment-Unresponsive Schizophrenia, Study Details and Tabular view, ClinicalTriais.gov, Sep. 2005, 12 pages.
NCT02810782, How to Treat Opiate Withdrawal in Neonates, Study Details and Tabular View, ClinicalTriais.gov, Jun. 2016, 14 pages.
Gadalla et al., Formulation of chlorpromazine hydrochloride syrup, CAS: 99: 163958, 1983.
Belozerova et al., Comparative effectiveness of preservatives for oral medicinal suspensions, CAS: 73: 7156, 1969.
Degert et al., improved method for avoiding the degradation of an active principle. CAS: 131: 23524, 1999.
Michigan Collaborative Standardization of Compounded Oral Liquids, Chlorpromazine, 2013, retrieved from https://www.mipedscompounds.org/sites/default/files/standard-formulations/Chlorpromazine.pdf, 1 page.
Attwood et al., "Chemical Kinetics and Drug Stability", Fifth Edition Modern Pharmaceutics, vol. 1, Basic Principles and Systems, 2009, Informa Healthcare USA, Inc. pages 207-208.
Sodium Benzoate In: Handbook of Pharmaceutical Excipients, Jan. 2009, p. 627.
Prohotsky et al., Formulation and Stability of an Extemporaneously Compounded Oral Solution of Chlorpromazine HCI, Journal of Pain & Palliative Care Pharmacotherapy, 2014, 13 pages.
Chlorpromazine 25 mg/5 ml Solution—Summary of Product Characteristics (SmPC) Pinewood Healthcare, 2017, accessed from https://www.medicines.org.uk/emc/product/4558/smpc, 15 pages.

\* cited by examiner

DETAIL "A"
SCALE 4:1

ORAL LIQUID COMPOSITIONS INCLUDING CHLORPROMAZINE

CROSS REFERENCE TO RELATED APPLICATION

This application is a continuation application claiming priority under 35 U.S.C. § 120 to U.S. patent application Ser. No. 17/036,121, filed Sep. 29, 2020, the entire disclosure of which is hereby incorporated herein by reference.

FIELD

Provided herein are oral liquid compositions including chlorpromazine exhibiting enhanced stability.

BACKGROUND

Chlorpromazine hydrochloride has a chemical structure of 2-chloro-10-[3-(dimethylamino) propyl] phenothiazine hydrochloride as shown in Formula 1 below:

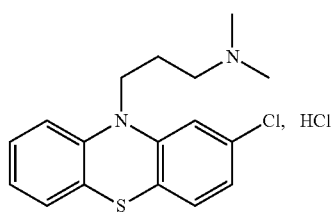

Formula 1

Chlorpromazine hydrochloride has a relative molecular mass of 355.33 g/mol. Two different forms of chlorpromazine hydrochloride (Form I and Form II) have been identified. Polymorphic Form I can be the more stable and have a higher melting point (195-198° C.) than Form II (110-120° C.). Chlorpromazine hydrochloride can exhibit a solubility greater than 1 g/mL across the pH range of 1 to 12 at ambient temperature. Chlorpromazine hydrochloride is slightly hygroscopic and adsorbs no more than 0.2% w/w moisture at up to 75% relative humidity (RH), and not more than 2.5% water at up to 90% relative humidity (RH). The acid dissociation constant (pKa) of chlorpromazine hydrochloride is 9.30 at 25° C.

Chlorpromazine has been used in treatment of manifestations of psychotic disorders; nausea and vomiting; restlessness and apprehension before surgery; acute intermittent *porphyria*; tetanus (e.g., as an adjunct); manifestations of the manic type of manic-depressive illness; intractable hiccups; and severe behavioral problems in children. Chlorpromazine is typically administered as a solid oral dosage form such as, for example, tablets, pills, and capsules. Oral ingestion is the most convenient and commonly employed route of drug delivery due to its ease of administration, high patient compliance, cost effectiveness, reduced sterility constraints, and flexibility in the design of dosage form. However, pediatric and geriatric patient populations may dislike or have difficulty swallowing solid oral dosage forms, which can lead to associated disadvantages, such as patient non-compliance. In such situations, oral liquid dosage forms, including solutions, suspensions and emulsions, can be easier to administer and more suitable for use.

Previously marketed oral solutions or syrups included formulations with ascorbic acid or sodium bisulfite, which negatively impact the stability of the solution, or alcohol, which is undesirable for formulations that may involve pediatric use. For example, Pharmaceutical Associates, Inc. previously marketed a chlorpromazine hydrochloride oral concentrate under ANDA Nos. 040224 and 040231 that included sodium bisulfite and ascorbic acid. Rosemont Pharmaceuticals markets chlorpromazine oral syrups in the United Kingdom that contain ascorbic acid and isopropyl alcohol.

Extemporaneously-prepared formulations are a sub-optimal option in instances where commercial liquid formulations are not available. For example, liquid dosage forms for chlorpromazine can be prepared by compounding tablets into a suspension. However, developing and compounding of pediatric formulations can be challenging for dispensing pharmacists, resulting in a variety of issues, such as, for example, inaccurate dosing, poor stability, poor taste, adherence problems, and lack of standardizations in extemporaneous compounding.

SUMMARY

Provided herein are stable oral liquid compositions including chlorpromazine or a pharmaceutically acceptable salt or solvate of chlorpromazine. According to one non-limiting aspect, the present disclosure provides an oral liquid pharmaceutical composition comprising chlorpromazine or a pharmaceutically acceptable salt or solvate thereof; preservative; chelating agent; and water. The oral liquid pharmaceutical composition retains at least about 90%, or at least about 95%, of an initial amount of the chlorpromazine or pharmaceutically acceptable salt or solvate thereof after three months stored at a temperature ranging from about 38° C. to about 42° C. and a relative humidity ranging from about 70% to about 80%. In certain non-limiting embodiment, the oral liquid pharmaceutical composition comprises less than 5% of impurity A after three months stored at a temperature ranging from about 38° C. to about 42° C. and a relative humidity ranging from about 70% to about 80%. In certain non-limiting embodiment, the oral liquid pharmaceutical composition comprises less than 1% of impurity A after three months stored at a temperature ranging from about 38° C. to about 42° C. and a relative humidity ranging from about 70% to about 80%.

According to another non-limiting aspect, the present disclosure provides an oral liquid pharmaceutical composition comprising chlorpromazine or a pharmaceutically acceptable salt or solvate thereof; sodium benzoate; EDTA; and water. The oral liquid pharmaceutical composition retains at least about 90%, or at least about 95%, of an initial amount of the chlorpromazine or pharmaceutically acceptable salt or solvate thereof after three months stored at a temperature ranging from about 38° C. to about 42° C. and a relative humidity ranging from about 70% to about 80%. In certain non-limiting embodiment, the oral liquid pharmaceutical composition comprises less than 5% of impurity A after three months stored at a temperature ranging from about 38° C. to about 42° C. and a relative humidity ranging from about 70% to about 80%. In certain non-limiting embodiment, the oral liquid pharmaceutical composition comprises less than 1% of impurity A after three months stored at a temperature ranging from about 38° C. to about 42° C. and a relative humidity ranging from about 70% to about 80%.

According to another non-limiting aspect, the present disclosure provides an oral liquid pharmaceutical composition comprising a total of about 25 mg/mL to about 35 mg/mL of chlorpromazine or a pharmaceutically acceptable salt or solvate thereof; about 0.1 mg/mL to about 5 mg/mL sodium benzoate; about 0.5 mg/mL to about 5 mg/mL EDTA; and water. The oral liquid pharmaceutical composition retains at least about 90% of an initial amount of chlorpromazine or pharmaceutically acceptable salt or solvate thereof after three months stored at a temperature ranging from about 38° C. to about 42° C. and a relative humidity ranging from about 70% to about 80%. In certain non-limiting embodiment, the oral liquid pharmaceutical composition comprises less than 5% of impurity A after three months stored at a temperature ranging from about 38° C. to about 42° C. and a relative humidity ranging from about 70% to about 80%. In certain non-limiting embodiment, the oral liquid pharmaceutical composition comprises less than 1% of impurity A after three months stored at a temperature ranging from about 38° C. to about 42° C. and a relative humidity ranging from about 70% to about 80%.

According to another non-limiting aspect, the present disclosure provides an oral liquid pharmaceutical composition comprising a total of about 25 mg/mL to about 35 mg/mL of chlorpromazine or a pharmaceutically acceptable salt or solvate thereof; about 0.1 mg/mL to about 5 mg/mL sodium benzoate; about 0.5 mg/mL to about 5 mg/mL EDTA; and water. The oral liquid pharmaceutical composition retains at least about 95% of an initial amount of chlorpromazine or pharmaceutically acceptable salt or solvate thereof after three months stored at a temperature ranging from about 38° C. to about 42° C. and a relative humidity ranging from about 70% to about 80%. In certain non-limiting embodiment, the oral liquid pharmaceutical composition comprises less than 5% of impurity A after three months stored at a temperature ranging from about 38° C. to about 42° C. and a relative humidity ranging from about 70% to about 80%. In certain non-limiting embodiment, the oral liquid pharmaceutical composition comprises less than 1% of impurity A after three months stored at a temperature ranging from about 38° C. to about 42° C. and a relative humidity ranging from about 70% to about 80%.

According to another non-limiting aspect, the present disclosure provides an oral liquid pharmaceutical composition comprising a total of about 90 mg/mL to about 110 mg/mL chlorpromazine or a pharmaceutically acceptable salt or solvate thereof; about 0.1 mg/mL to about 5 mg/mL sodium benzoate; about 0.5 mg/mL to about 5 mg/mL EDTA; and water. The oral liquid pharmaceutical composition retains at least about 90% of an initial amount of the chlorpromazine or pharmaceutically acceptable salt or solvate thereof after three months stored at a temperature ranging from about 38° C. to about 42° C. and a relative humidity ranging from about 70% to about 80%. In certain non-limiting embodiment, the oral liquid pharmaceutical composition comprises less than 5% of impurity A after three months stored at a temperature ranging from about 38° C. to about 42° C. and a relative humidity ranging from about 70% to about 80%. In certain non-limiting embodiment, the oral liquid pharmaceutical composition comprises less than 1% of impurity A after three months stored at a temperature ranging from about 38° C. to about 42° C. and a relative humidity ranging from about 70% to about 80%.

According to another non-limiting aspect, the present disclosure provides an oral liquid pharmaceutical composition comprising a total about 90 mg/mL to about 110 mg/mL chlorpromazine or a pharmaceutically acceptable salt or solvate thereof; about 0.1 mg/mL to about 5 mg/mL sodium benzoate; about 0.5 mg/mL to about 5 mg/mL EDTA; and water. The oral liquid pharmaceutical composition retains at least about 95% of an initial amount of the chlorpromazine or pharmaceutically acceptable salt or solvate thereof after three months stored at a temperature ranging from about 38° C. to about 42° C. and a relative humidity ranging from about 70% to about 80%. In certain non-limiting embodiment, the oral liquid pharmaceutical composition comprises less than 5% of impurity A after three months stored at a temperature ranging from about 38° C. to about 42° C. and a relative humidity ranging from about 70% to about 80%. In certain non-limiting embodiment, the oral liquid pharmaceutical composition comprises less than 1% of impurity A after three months stored at a temperature ranging from about 38° C. to about 42° C. and a relative humidity ranging from about 70% to about 80%.

BRIEF DESCRIPTION OF THE DRAWINGS

Various features and characteristics of non-limiting and non-exhaustive embodiments disclosed and described in this specification may be better understood by reference to the accompanying figures, wherein all dimensions are in inches, and in which:

FIG. 2C is a top view of the bottle of FIG. 2A;

FIG. 2D is a bottom view of the bottle of FIG. 2A; and

DETAILED DESCRIPTION OF CERTAIN NON-LIMITING EMBODIMENTS

Figure 1A:
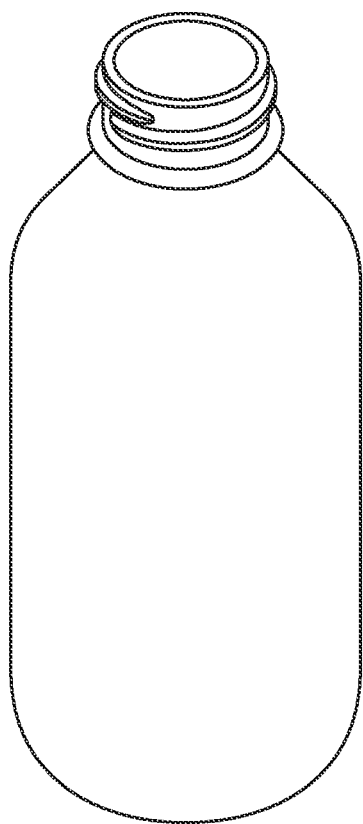
FIG. 1A is a perspective view of a 4 oz. amber polyethylene terephthalate (PET) bottle suitable to receive embodiments of an oral liquid composition comprising chlorpromazine according to the present disclosure.
Figure 1B:
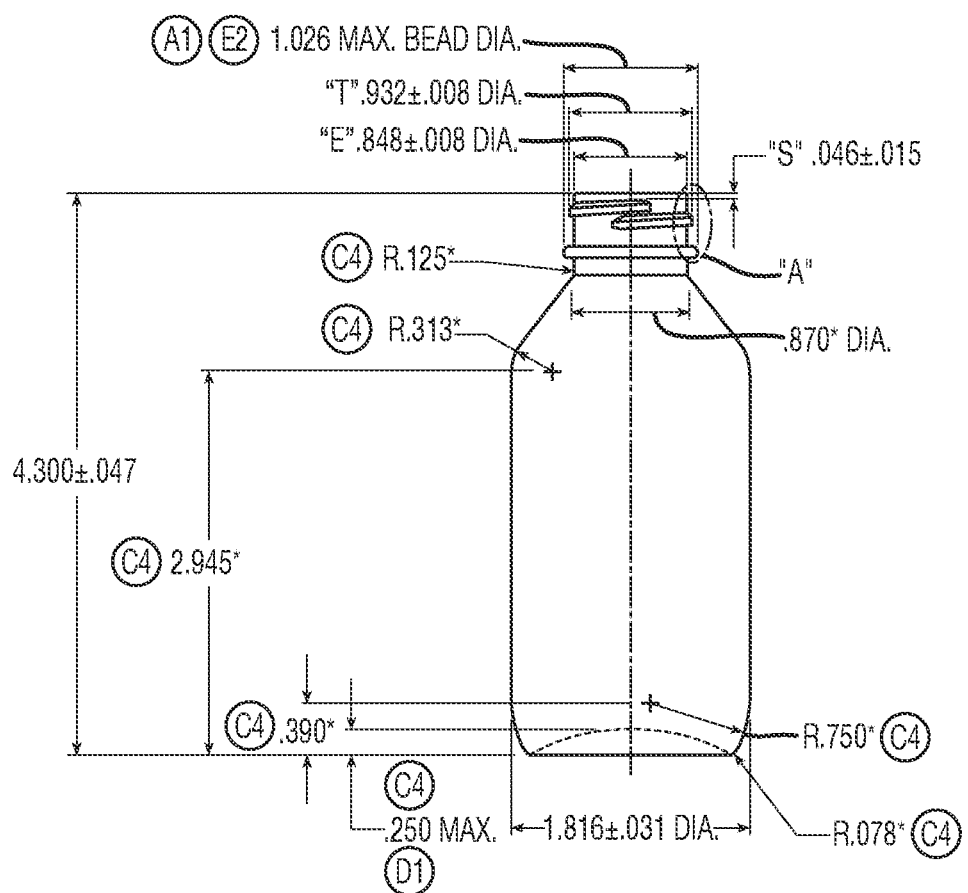
FIG. 1B is a side elevational view of the bottle of FIG. 1A.
Figure 1C:
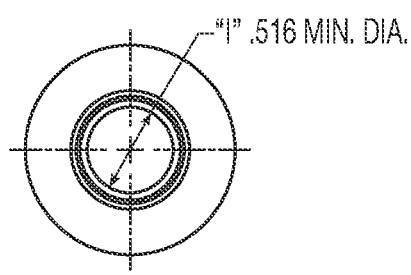
FIG. 1C is a top view of the bottle of FIG. 1A.
Figure 1D:
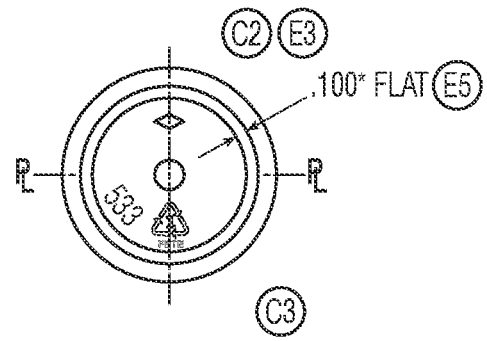
FIG. 1D is a bottom view of the bottle of FIG. 1A.
Figure 1E:
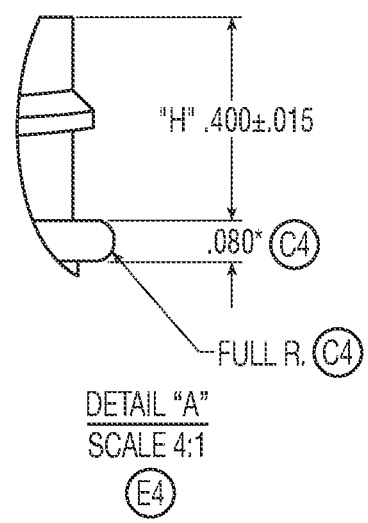
FIG. 1E is a detail view of area "A" in FIG. 1B.
Figure 2A:
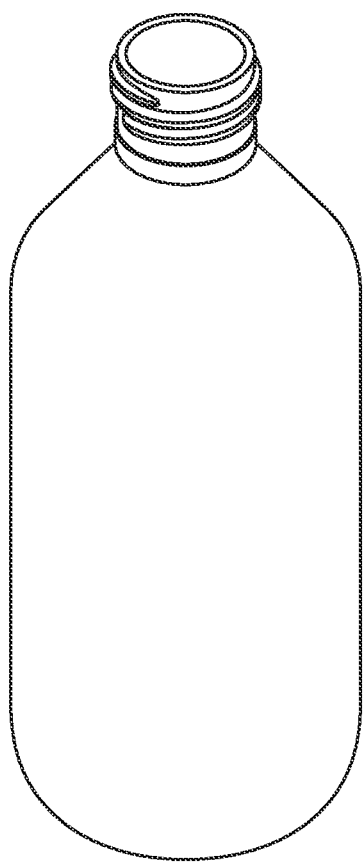
FIG. 2A is a perspective view of an 8 oz. amber PET bottle suitable to receive embodiments of oral liquid compositions comprising chlorpromazine according to the present disclosure.
Figure 2B:
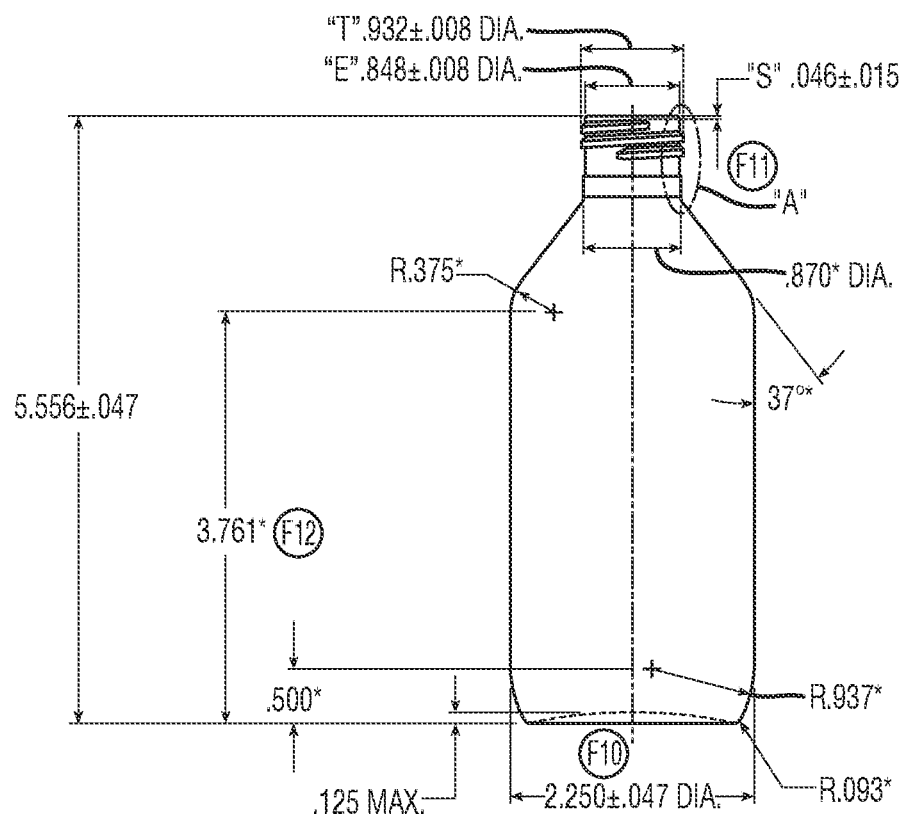
FIG. 2B is a side elevational view of the bottle of FIG. 2A.
Figure 2E:
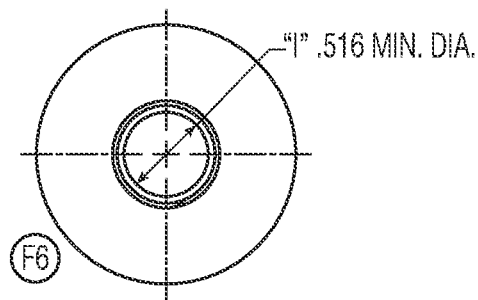
FIG. 2E is a detail view of area "A" in FIG. 2B.
Figure 2E:
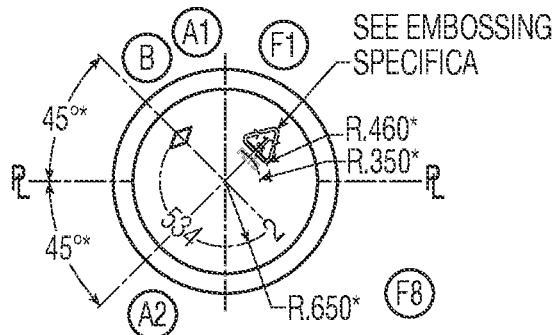
Figure 2E:
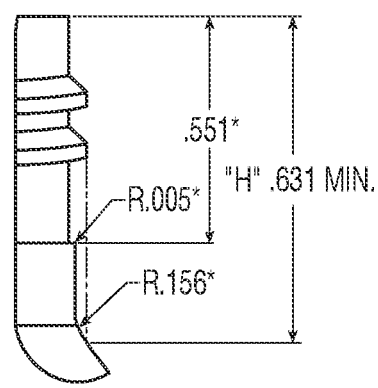

Various examples are described and illustrated herein to provide an overall understanding of the structure, function, and use of the disclosed compositions and methods. The various examples described and illustrated herein are non-limiting and non-exhaustive. Thus, the invention is not limited by the description of the various non-limiting and non-exhaustive examples disclosed herein. The features and characteristics illustrated and/or described in connection with various examples may be combined with the features and characteristics of other examples. Such modifications and variations are intended to be included within the scope of the present disclosure. As such, the claims may be amended to recite any features or characteristics expressly or inherently described in, or otherwise expressly or inherently supported by, the present disclosure. Further, Applicant reserves the right to amend the claims to affirmatively disclaim features or characteristics that may be present in the prior art. The various non-limiting embodiments disclosed and described in the present disclosure can comprise, consist of, or consist essentially of the features and characteristics as variously described herein.

Any references herein to "various embodiments," "some embodiments," "one embodiment," "an embodiment," or like phrases mean that a particular feature, structure, or characteristic described in connection with the example is included in at least one embodiment. Thus, appearances of the phrases "in various embodiments," "in some embodiments," "in one embodiment," "in an embodiment," or like phrases in the specification do not necessarily refer to the same non-limiting embodiment. Furthermore, the particular described features, structures, or characteristics may be combined in any suitable manner in one or more non-limiting embodiments. Thus, the particular features, structures, or characteristics illustrated or described in connection with one non-limiting embodiment may be combined, in whole or in part, with the features, structures, or characteristics of one or more other non-limiting embodiments without limitation. Such modifications and variations are intended to be included within the scope of the present non-limiting embodiments.

Any numerical range recited herein includes all sub-ranges subsumed within the recited range. For example, a range of "1 to 10" includes all sub-ranges between (and including) the recited minimum value of 1 and the recited maximum value of 10, that is, having a minimum value equal to or greater than 1 and a maximum value equal to or less than 10. Any maximum numerical limitation recited in this specification is intended to include all lower numerical limitations subsumed therein, and any minimum numerical limitation recited in the present disclosure is intended to include all higher numerical limitations subsumed therein. Accordingly, Applicant reserves the right to amend the present disclosure, including the claims, to expressly recite any sub-range subsumed within the ranges expressly recited. All such ranges are inherently described in the present disclosure.

The grammatical articles "a," "an," and "the," as used herein, are intended to include "at least one" or "one or more," unless otherwise indicated, even if "at least one" or "one or more" is expressly used in certain instances. Thus, the foregoing grammatical articles are used herein to refer to one or more than one (i.e., to "at least one") of the particular identified elements. Further, the use of a singular noun includes the plural, and the use of a plural noun includes the singular, unless the context of the usage requires otherwise.

Provided herein are stable oral liquid compositions including chlorpromazine or a pharmaceutically acceptable salt or solvate of chlorpromazine. Embodiments of the compositions according to the present disclosure can provide advantages over conventional oral solid dosage forms comprising chlorpromazine including, for example, ease of administration, improved absorption, increased patient compliance, and accurate/precise delivery of chlorpromazine to the patient. Additionally, embodiment of the present compositions can provide advantages over conventional liquid dosage forms comprising chlorpromazine including, for example, increased stability.

The present inventors have discovered that embodiments of oral liquid compositions comprising chlorpromazine or a pharmaceutically acceptable salt or solvate of chlorpromazine as an active pharmaceutical ingredient (API), a limited number of excipients, and a solution pH in a particular pH range, surprisingly and unexpectedly exhibit markedly improved stability of chlorpromazine and reduction in generation of impurities. For example, embodiments of compositions according to the present disclosure can be stable for at least 18 months, at least 24 months, or longer when stored under certain environmental conditions.

Excipients included in the liquid oral compositions can be selected to aid development of a simple manufacturing process and result in a stable product that meets the Quality Target Product Profile (QTPP). The selection of excipients can achieve an optimal compatibility, processability, stability, shelf life, palatability, and other quality attributes of the resulting pharmaceutical product. In various non-limiting embodiments, excipients included in embodiments of compositions according to the present disclosure comprise one or more of a buffering system, a preservative, a chelating agent, a sweetener, a flavoring agent, and a coloring agent, along with water.

Degradation products of the excipients and/or chlorpromazine should be controlled to limit their concentration over time. The individual, unknown, and total impurities limit for liquid oral compositions comprising chlorpromazine can be set according to, for example, the International Council for Harmonization of Technical Requirements for Pharmaceuticals for Human Use (ICH) and/or the United States Pharmacopeia (USP) thresholds. For example, embodiments of liquid oral compositions comprising chlorpromazine or a pharmaceutically acceptable salt or solvate of chlorpromazine according to the present disclosure can comprise an impurity A content of no greater than about 5% based on the total weight of the liquid oral composition, such as, for example, no greater than about 4%, no greater than about 3%, no greater than about 2%, no greater than about 1%, no greater than about 0.75%, no greater than about 0.58%, or no greater than about 0.5%, based on the total weight of the liquid oral composition. In the present disclosure, "impurity A" refers to chlorpromazine sulfoxide. In certain non-limiting embodiments, the liquid oral compositions according to the present disclosure can comprise an impurity content of a specific unidentified impurity no greater than about 0.1%, based on the total weight of the composition, such as, for example, no greater than about 0.05%, based on the total weight of the composition. In various non-limiting embodiments, the liquid oral composition according to the present disclosure can comprise a total impurity content no greater than about 7% based on the composition, such as, for example, no greater than about 6%, no greater than about 5%, no greater than about 4%, no greater than about 3%, no greater than about 2%, no greater than about 1%, no greater than about 0.75%, or no greater than about 0.5%, based on the total weight of the composition. For example, in some non-limiting embodiments, the liquid oral compositions according to the present disclosure can comprise an impurity A content no greater than about 5% based on the total weight of the composition, an unidentified impurity content no greater than about 0.1% based on the total weight of the composition, and a total impurity content no greater than about 7.0% based on the total weight of the composition. In various non-limiting embodiments, liquid oral compositions according to the present disclosure can comply with ICT Q3B(R) Impurities in New Drug Products requirements (Revision 2), August 2006.

Excipients for embodiments of liquid oral compositions according to the present disclosure can be selected to create and/or maintain a desirable pH that enhances stability of chlorpromazine or pharmaceutically acceptable salt or solvate of chlorpromazine in the compositions. The pH of the liquid oral composition can affect stability of chlorpromazine and/or other excipients. For example, a pH of liquid oral compositions according to the present disclosure can enhance the effectiveness of sodium benzoate as a preservative. In some non-limiting embodiments, the oral liquid compositions comprising chlorpromazine or a pharmaceutically acceptable salt or solvate of chlorpromazine according to the present disclosure comprise a pH no greater than 5.4, such as, for example, no greater than about 5.0, no greater than about 4.5, no greater than about 4.4, no greater than about 4.3, no greater than about 4.2, no greater than about 4.1, no greater than about 4.0, or no greater than about 3.95. In certain non-limiting embodiments, the oral liquid compositions comprising chlorpromazine or a pharmaceutically acceptable salt or solvate of chlorpromazine according to the present disclosure comprise a pH of at least about 2, such as, for example, at least about 2.5, at least about 3, at least about 3.5, at least about 3.6, at least about 3.7, at least about 3.8, or at least about 3.85.

Certain non-limiting embodiments of the oral liquid compositions according to the present disclosure comprise a pH in a range of about 2.0 to about 5.0, such as, for example, about 2.5 to about 4.5, about 3.0 to about 4.5, about 3.0 to about 5.0, about 3.5 to about 4.5, about 3.6 to about 4.4, about 3.7 to about 4.3, about 3.6 to about 4.3, about 3.7 to about 4.2, about 3.7 to about 4.1, about 3.8 to about 4.0, or about 3.85 to about 3.95. In various non-limiting embodiments, the oral liquid compositions according to the present disclosure can comprise a pH of about 3.7, about 3.8, about 3.85, about 3.9, about 3.95, about 4.0, or about 4.1.

Chlorpromazine

The oral liquid compositions according to the present disclosure comprise chlorpromazine or a pharmaceutically acceptable salt or solvate thereof as an API. Suitable compounds include the free base, organic and inorganic salts, isomers, isomer salts, solvates, polymorphs, amorphous forms, complexes, etc. Chlorpromazine and its various derivatives can be purchased from commercial sources or can be prepared according to known methods. In certain non-limiting embodiments, the compositions disclosed herein include chlorpromazine free base. In various non-limiting embodiments, the compositions disclosed herein include a chlorpromazine salt. For example, in certain non-limiting embodiments, the compositions disclosed herein include chlorpromazine hydrochloride and, in some non-limiting embodiments, the chlorpromazine hydrochloride is polymorph form I. In some non-limiting embodiments, the compositions disclosed herein include a solvate of chlorpromazine.

In the remainder of the present detailed description, "chlorpromazine" refers collectively to chlorpromazine and all pharmaceutically acceptable salts and solvates of chlorpromazine unless stated otherwise.

In various non-limiting embodiments, oral liquid compositions according to the present disclosure can comprise a total content of chlorpromazine is no greater than about 200 mg/mL, based on the volume of the composition, such as, for example, no greater than about 150 mg/mL, no greater than about 110 mg/mL, no greater than about 105 mg/mL, no greater than about 104 mg/mL, no greater than about 103 mg/mL, no greater than about 102 mg/mL, no greater than about 101 mg/mL, no greater than about 100 mg/mL, no greater than about 35 mg/mL, no greater than about 34 mg/mL, no greater than about 33 mg/mL, no greater than about 32 mg/mL, no greater than about 31 mg/mL, or no greater than about 30 mg/mL, based on total volume of the composition. In certain non-limiting embodiments, oral liquid compositions according to the present disclosure comprise a content of chlorpromazine of at least about 1.0 mg/mL, such as, for example, at least about 5.0 mg/mL, at least about 25 mg/mL, at least about 26 mg/mL, at least about 27 mg/mL, at least about 28 mg/mL, at least about 29 mg/mL, at least about 30 mg/mL, at least about 90 mg/mL, at least about 95 mg/mL, at least about 96 mg/mL, at least about 97 mg/mL, at least about 98 mg/mL, at least about 99 mg/mL, or at least about 100 mg/mL, based on the total volume of the composition. In various non-limiting embodiments, oral liquid compositions according to the present disclosure comprise a content of chlorpromazine in a range of about 1.0 mg/mL to about 200.0 mg/mL, such as, for example, about 5.0 mg/mL to about 150 mg/mL, about 25.0 mg/mL to about 35 mg/mL, about 26.0 mg/mL to about 34.0 mg/mL, about 27.0 mg/mL to about 33.0 mg/mL, about 28.0 mg/mL to about 32.0 mg/mL, about 29.0 mg/mL to about 31 mg/mL, about 29.5 mg/mL to about 30.5 mg/mL, about 90 mg/mL to about 110 mg/mL, about 95 mg/mL to about 105 mg/mL, about 96 mg/mL to about 104 mg/mL, about 97 mg/mL to about 103 mg/mL, about 98 mg/mL to about 102 mg/mL, about 99 mg/mL to about 101 mg/mL, or about 99.5 mg/mL to about 100.5 mg/mL, based on total volume of the composition. In certain non-limiting embodiments, oral liquid compositions according to the present disclosure comprise a content of chlorpromazine of about 29 mg/mL, about 30 mg/mL, about 31 mg/mL, about 99 mg/mL, about 100 mg/mL, or about 101 mg/mL, based on total volume of the composition. In certain non-limiting embodiments, oral liquid compositions according to the present disclosure can comprise chlorpromazine content of about 30 mg/mL or about 100 mg/mL, based on total volume of the composition.

Preservative

In various non-limiting embodiments, oral liquid compositions according to the present disclosure can comprise a preservative such as, for example, one or more of sodium benzoate, methyl-, ethyl-, propyl-, or butyl-esters of hydroxy benzoic acid or sodium salts thereof, benzoic acid, sodium benzoate, chlorhexidine, benzalkonium chloride, 2-phenoxyethanol, cetrimide, potassium sorbate, imidurea, dichlorobenzyl alcohol, thiomersal, and parabens. In certain non-limiting embodiments, oral liquid compositions according to the present disclosure comprise sodium benzoate.

Sodium benzoate can be an antimicrobial preservative including bacteriostatic and antifungal properties attributed to undissociated benzoic acid. The preservative efficacy of sodium benzoate may be enhanced in acidic solutions (e.g., a pH in a range of about 2.0 to about 5.0). Sodium benzoate can occur as a white granular or crystalline, slightly hygroscopic powder and can be odorless, or with faint odor of benzoin, and can comprise an unpleasant sweet and saline taste. It has been observed that sodium benzoate can interact with chlorpromazine hydrochloride and, thus, the concentration of sodium benzoate and the pH of the oral liquid composition according to the present disclosure can be optimized to limit the interaction between sodium benzoate and chlorpromazine hydrochloride.

In various non-limiting embodiments, oral liquid compositions according to the present disclosure comprise a preservative content no greater than about 5 mg/mL, such as, for example, no greater than about 2 mg/mL, no greater than about 1.5 mg/mL, no greater than about 1.2 mg/mL, no greater than about 1.1 mg/mL, no greater than about 1.05 mg/mL, no greater than about 1 mg/mL, no greater than about 0.95 mg/mL, no greater than about 0.8 mg/mL, no greater than about 0.7 mg/mL, no greater than about 0.6 mg/mL, no greater than about 0.5 mg/mL, no greater than about 0.4 mg/mL, no greater than about 0.35 mg/mL, or no greater than about 0.3 mg/mL, based on total volume of the composition. In certain non-limiting embodiments, oral liquid compositions according to the present disclosure comprise a preservative content of at least about 0.05 mg/mL, such as, for example, at least about 0.1 mg/mL, at least about 0.2 mg/mL, at least about 0.25 mg/mL, at least about 0.3 mg/mL, at least about 0.35 mg/mL, at least about 0.4 mg/mL, at least about 0.5 mg/mL, at least about 0.6 mg/mL, at least about 0.7 mg/mL, at least about 0.8 mg/mL, at least about 0.9 mg/mL, at least about 0.95 mg/mL, or at least about 1.0 mg/mL, based on the total volume of the composition. For example, in various non-limiting embodiments, the oral liquid compositions according to the present disclosure can comprise a preservative content in a range of about 0.05 mg/mL to about 5.0 mg/mL, such as, for example, about 0.1 mg/mL to about 2 mg/mL, about 0.1 mg/mL to about 1.5 mg/mL, about 0.2 mg/mL to about 0.4 mg/mL, about 0.25 mg/mL to about 0.35 mg/mL, about 0.9 mg/mL to about 1.1 mg/mL, or about 0.95 mg/mL to about 1.05 mg/mL, based on total volume of the composition.

In certain non-limiting embodiments, the oral liquid compositions according to the present disclosure can comprise a preservative content of about 0.25 mg/mL, about 0.3 mg/mL, about 0.35 mg/mL, about 0.95 mg/mL, about 1.0 mg/mL, or about 1.05 mg/mL. In certain non-limiting embodiments, the oral liquid compositions according to the present disclosure can comprise a preservative content of about 0.30 mg/mL and a chlorpromazine content of about 30 mg/mL. In certain non-limiting embodiments, the oral liquid compositions according to the present disclosure comprise a preservative content of about 1.0 mg/mL and a chlorpromazine content of about 100 mg/mL.

In various non-limiting embodiments, the oral liquid compositions according to the present disclosure comprise a chlorpromazine to preservative weight ratio in a range of about 500:1 to about 1:1, such as, for example, about 300:1 to about 2:1, about 200:1 to about 5:1, about 150:1 to about 10:1, about 120:1 to about 80:1, about 110:1 to about 90:1, about 105:1 to about 95:1, or about 101:1 to about 99:1. In certain non-limiting embodiments, the oral liquid compositions according to the present disclosure comprise a chlorpromazine to preservative weight ratio of about 99:1, about 100:1, or about 101:1. In various non-limiting embodiments, oral liquid compositions according to the present disclosure comprise a chlorpromazine to preservative weight ratio of about 100:1.

In various non-limiting embodiments, the oral liquid compositions according to the present disclosure can comprise a chlorpromazine to preservative mole ratio in a range of about 500:1 to about 1:1, such as, for example, about 300:1 to about 2:1, about 200:1 to about 5:1, about 150:1 to about 10:1, about 100:1 to about 20:1, about 60:1 to about 20:1, about 50:1 to about 40:1, or about 46:1 to about 44:1. In certain non-limiting embodiments, the oral liquid compositions according to the present disclosure comprise a chlorpromazine to preservative mole ratio of about 44:1, about 45:1, or about 46:1. In certain non-limiting embodiments, the oral liquid compositions according to the present disclosure comprise a chlorpromazine to preservative mole ratio of about 45:1.

In various non-limiting embodiments, the oral liquid compositions according to the present disclosure comprise sodium benzoate in a concentration no greater than about 5 mg/mL, such as, for example, no greater than about 2 mg/mL, no greater than about 1.5 mg/mL, no greater than about 1.2 mg/mL, no greater than about 1.1 mg/mL, no greater than about 1.05 mg/mL, no greater than about 1 mg/mL, no greater than about 0.95 mg/mL, no greater than about 0.8 mg/mL, no greater than about 0.7 mg/mL, no greater than about 0.6 mg/mL, no greater than about 0.5 mg/mL, no greater than about 0.4 mg/mL, no greater than about 0.35 mg/mL, or no greater than about 0.3 mg/mL, based on total volume of the composition. In certain non-limiting embodiments, the oral liquid compositions according to the present disclosure comprise a sodium benzoate content of at least about 0.05 mg/mL, such as, for example, at least about 0.1 mg/mL, at least about 0.2 mg/mL, at least about 0.25 mg/mL, at least about 0.3 mg/mL, at least about 0.35 mg/mL, at least about 0.4 mg/mL, at least about 0.5 mg/mL, at least about 0.6 mg/mL, at least about 0.7 mg/mL, at least about 0.8 mg/mL, at least about 0.9 mg/mL, at least about 0.95 mg/mL, or at least about 1.0 mg/mL, based on total volume of the composition. For example, in various non-limiting embodiments, the oral liquid compositions according to the present disclosure comprise a sodium benzoate content in a range of about 0.05 mg/mL to about 5.0 mg/mL, such as, for example, about 0.1 mg/mL to about 2 mg/mL, about 0.1 mg/mL to about 1.5 mg/mL, about 0.2 mg/mL to about 0.4 mg/mL, about 0.25 mg/mL to about 0.35 mg/mL, about 0.9 mg/mL to about 1.1 mg/mL, or about 0.95 mg/mL to about 1.05 mg/mL, based on total volume of the composition. In certain non-limiting embodiments, the oral liquid compositions according to the present disclosure comprise a sodium benzoate content of about 0.25 mg/mL, about 0.3 mg/mL, about 0.35 mg/mL, about 0.95 mg/mL, about 1.0 mg/mL, or about 1.05 mg/mL, based on total volume of the composition. In certain non-limiting embodiments, the oral liquid compositions according to the present disclosure comprise a sodium benzoate content of about 0.30 mg/mL and a chlorpromazine content of about 30 mg/mL, based on total volume of the composition. In certain non-limiting embodiments, the oral liquid compositions according to the present disclosure comprise a sodium benzoate content of about 1.0 mg/mL and a chlorpromazine content of about 100 mg/mL, based on total volume of the composition.

In various non-limiting embodiments, the oral liquid compositions according to the present disclosure comprise a chlorpromazine to sodium benzoate weight ratio in a range of about 500:1 to about 1:1, such as, for example, about 300:1 to about 2:1, about 200:1 to about 5:1, about 150:1 to about 10:1, about 120:1 to about 80:1, about 110:1 to about 90:1, about 105:1 to about 95:1, or about 101:1 to about 99:1. In certain non-limiting embodiments, the oral liquid compositions according to the present disclosure comprise a chlorpromazine to sodium benzoate weight ratio of about 99:1, about 100:1, or about 101:1. In certain non-limiting embodiments, the oral liquid composition according to the present disclosure comprises a chlorpromazine to sodium benzoate weight ratio of about 100:1.

In various non-limiting embodiments, the oral liquid compositions according to the present disclosure comprise a chlorpromazine to sodium benzoate mole ratio in a range of about 500:1 to about 1:1, such as, for example, about 300:1 to about 2:1, about 200:1 to about 5:1, about 150:1 to about 10:1, about 100:1 to about 20:1, about 60:1 to about 20:1, about 50:1 to about 40:1, or about 46:1 to about 44:1. In certain non-limiting embodiments, the oral liquid composition according to the present disclosure comprises a chlorpromazine to sodium benzoate mole ratio of about 44:1, about 45:1, or about 46:1. In certain non-limiting embodiments, the oral liquid composition according to the present disclosure comprises a chlorpromazine to sodium benzoate mole ratio of about 45:1.

Buffering System

Non-limiting embodiments of the oral liquid compositions according to the present disclosure can comprise a buffering system to obtain and/or enhance stability of a selected pH or pH range. For example, the buffering system can comprise a pair of an acid and a salt thereof, such as, for example, at least one of citric acid and a citrate salt, a phosphoric acid and phosphate salt, an acetic acid and acetate salt, a carbonic acid and carbonate salt, and hydrochloric acid and tris(hydroxymethyl)aminomethane (Tris). In other non-limiting embodiments, the buffering system can comprise arginine. In various non-limiting embodiments, the buffering system can comprise citric acid and a citrate salt. The citrate salt can comprise at least one of sodium citrate, potassium citrate, calcium citrate, magnesium citrate, a hydrate, a solvate, or an anhydrous form thereof. In some non-limiting embodiments, the citrate salt can comprise at least one of monosodium citrate, disodium citrate, trisodium citrate, trisodium citrate dihydrate, anhydrous trisodium citrate, disodium hydrogen citrate, disodium citrate sesquihydrate, calcium citrate, and magnesium citrate. In certain non-limiting embodiments, the buffering system can comprise citric acid and sodium citrate. In various non-limiting embodiments, the sodium citrate is sodium citrate dihydrate.

In non-limiting embodiments, oral liquid compositions according to the present disclosure can comprise a sufficient concentration of a buffering system to provide a pH in a range of about 2.0 to about 5.4, such as, for example, about 2.0 to about 5.0, about 2.5 to about 4.5, about 3.0 to about 4.5, about 3.5 to about 4.5, about 3.6 to about 4.4, about 3.7 to about 4.3, about 3.7 to about 4.2, about 3.7 to about 4.1, about 3.8 to about 4.0, or about 3.85 to about 3.95.

In certain non-limiting embodiments, oral liquid compositions according to the present disclosure comprise a sufficient concentration of a buffering system to provide a pH of about 3.7, about 3.8, about 3.85, about 3.9, about 3.95, about 4.0, or about 4.1. For example, in various non-limiting embodiments, the oral liquid composition according to the present disclosure can comprise a pH of about 3.9.

In various non-limiting embodiments, the oral liquid compositions according to the present disclosure comprise a buffering system acid concentration no greater than about 5 mg/mL, such as, for example, no greater than about 4 mg/mL, no greater than about 3.5 mg/mL, no greater than about 3.4 mg/mL, no greater than about 3.39 mg/mL, no greater than about 3.35 mg/mL, no greater than about 3.3 mg/mL, no greater than about 3.2 mg/mL, no greater than about 3.0 mg/mL, no greater than about 2.0 mg/mL, no greater than about 1.5 mg/mL, no greater than about 1.1 mg/mL, no greater than about 1.05 mg/mL, or no greater than about 1 mg/mL, based on total volume of the composition. In certain non-limiting embodiments, oral liquid compositions according to the present disclosure comprise a buffering system acid content of at least about 0.05 mg/mL, such as, for example, at least about 0.1 mg/mL, at least about 0.5 mg/mL, at least about 0.8 mg/mL, at least about 0.9 mg/mL, at least about 0.95 mg/mL, at least about 1.0 mg/mL, at least about 1.05 mg/mL, at least about 1.1 mg/mL, at least about 1.5 mg/mL, at least about 2.0 mg/mL, at least about 3.0 mg/mL, at least about 3.2 mg/mL, or at least about 3.3 mg/mL, based on total volume of the composition. For example, in various non-limiting embodiments, oral liquid compositions according to the present disclosure comprise a buffering system acid content in a range of about 0.05 mg/mL to about 5.0 mg/mL, such as, for example, about 0.1 mg/mL to about 4 mg/mL, about 0.9 mg/mL to about 1.1 mg/mL, about 1.0 mg/mL to about 1.05 mg/mL, about 3.0 mg/mL to about 3.5 mg/mL, about 3.2 mg/mL to about 3.4 mg/mL, about 3.3 mg/mL to about 3.4 mg/mL, or about 3.35 mg/mL to about 3.4 mg/mL, based on total volume of the composition In certain non-limiting embodiments, the oral liquid compositions according to the present disclosure comprise a buffering system acid content of about 1.0 mg/mL, about 1.018 mg/mL, about 3.393 mg/mL, or about 3.4 mg/mL. In certain non-limiting embodiments, the oral liquid composition according to the present disclosure comprises a buffering system acid content of about 1.018 mg/mL and a chlorpromazine content of about 30 mg/mL. In certain other non-limiting embodiments, the oral liquid composition according to the present disclosure comprises a buffering system acid content of about 3.393 mg/mL and a chlorpromazine content of about 100 mg/mL.

In various non-limiting embodiments, oral liquid compositions according to the present disclosure comprise a chlorpromazine to buffering system acid weight ratio in a range of about 100:1 to about 1:1, such as, for example, about 75:1 to about 2:1, about 60:1 to about 5:1, about 50:1 to about 10:1, about 40:1 to about 20:1, about 35:1 to about 25:1, or about 31:1 to about 29:1. In certain non-limiting embodiments, oral liquid compositions according to the present disclosure comprise an API to buffering system acid weight ratio of about 29:1, about 29.5:1, or about 30:1.

In various non-limiting embodiments, oral liquid compositions according to the present disclosure comprise chlorpromazine to buffering system acid mole ratio in a range of about 100:1 to about 1:1, such as, for example, about 75:1 to about 2:1, about 60:1 to about 5:1, about 50:1 to about 5:1, about 30:1 to about 10:1, about 20:1 to about 10:1, or about 18:1 to about 16:1.

In certain non-limiting embodiments, the oral liquid composition according to the present disclosure comprises a chlorpromazine to buffering system acid mole ratio of about 17:1, about 18:1, or about 19:1.

In various non-limiting embodiments, oral liquid compositions according to the present disclosure comprise a buffering system salt content no greater than about 10 mg/mL, such as, for example, no greater than about 7 mg/mL, no greater than about 6 mg/mL, no greater than about 5.5 mg/mL, no greater than about 5.3 mg/mL, no greater than about 5.25 mg/mL, no greater than about 5.21 mg/mL, no greater than about 5.2 mg/mL, no greater than about 5.1 mg/mL, no greater than about 5.0 mg/mL, no greater than about 2.0 mg/mL, no greater than about 1.75 mg/mL, no greater than about 1.6 mg/mL, or no greater than about 1.57 mg/mL, based on total volume of the composition. In certain non-limiting embodiments, oral liquid compositions according to the present disclosure comprise a buffering system salt content of at least about 0.1 mg/mL, such as, for example, at least about 0.5 mg/mL, at least about 1.0 mg/mL, at least about 1.4 mg/mL, at least about 1.5 mg/mL, at least about 1.55 mg/mL, at least about 1.57 mg/mL, at least about 1.6 mg/mL, at least about 1.75 mg/mL, at least about 2.0 mg/mL, at least about 5.0 mg/mL, or at least about 5.25 mg/mL, based on total volume of the composition. For example, in various non-limiting embodiments, oral liquid compositions according to the present disclosure comprise a buffering system salt content in a range of about 0.1 mg/mL to about 10.0 mg/mL, such as, for example, about 0.5 mg/mL to about 7 mg/mL, about 1.4 mg/mL to about 1.7 mg/mL, about 1.5 mg/mL to about 1.6 mg/mL, about 1.55 mg/mL to about 1.57 mg/mL, about 5.0 mg/mL to about 5.5 mg/mL, about 5.1 mg/mL to about 5.4 mg/mL, about 5.2 mg/mL to about 5.3 mg/mL, or about 5.2 mg/mL to about 5.25 mg/mL, based on total volume of the composition. In certain non-limiting embodiments, the oral liquid composition according to the present disclosure comprises a buffering system salt content of about 1.5 mg/mL, about 1.566 mg/mL, about 5.2 mg/mL, or about 5.220 mg/mL, based on total volume of the composition. In certain non-limiting embodiments, oral liquid compositions according to the present disclosure comprise a buffering system salt content of about 1.566 mg/mL and a chlorpromazine content of about 30 mg/mL. In certain other non-limiting embodiments, oral liquid compositions according to the present disclosure comprise a buffering system acid content of about 5.220 mg/mL and a chlorpromazine content of about 100 mg/mL.

In various non-limiting embodiments, oral liquid compositions according to the present disclosure comprise a chlorpromazine to buffering system salt weight ratio in a range of about 100:1 to about 1:1, such as, for example, about 75:1 to about 2:1, about 50:1 to about 5:1, about 40:1 to about 5:1, about 30:1 to about 10:1, about 25:1 to about 15:1, or about 20:1 to about 19:1.

In certain non-limiting embodiments, oral liquid compositions according to the present disclosure comprise a chlorpromazine to buffering system salt weight ratio of about 19:1, about 20:1, or about 21:1.

In various non-limiting embodiments, the oral liquid compositions according to the present disclosure comprise a chlorpromazine to buffering system salt mole ratio in a range of about 100:1 to about 1:1, such as, for example, about 75:1 to about 2:1, about 60:1 to about 5:1, about 50:1 to about 5:1, about 30:1 to about 10:1, about 20:1 to about 10:1, or about 18:1 to about 16:1. In certain non-limiting embodiments, the oral liquid compositions according to the present disclosure comprise a chlorpromazine to buffering system salt mole ratio of about 17:1, about 18:1, or about 19:1.

In various non-limiting embodiments, the oral liquid compositions according to the present disclosure comprise a buffering system salt to buffering system acid mole ratio in a range of about 10:1 to about 0.1:1, such as, for example, about 5:1 to about 0.5:1, about 4:1 to about 0.6:1, about 3:1 to about 0.7:1, about 2:1 to about 0.8:1, or about 1.1:1 to about 0.9:1. In certain non-limiting embodiments, the oral liquid compositions according to the present disclosure comprise a buffering system salt to buffering system acid mole ratio of about 0.9:1, about 1:1, or about 1.1:1.

In various non-limiting embodiments, the acid and salt thereof of the buffering system can comprise citric acid and sodium citrate. In addition to buffering, citric acid (e.g., anhydrous or monohydrate) can be used an acidifying agent, antioxidant, chelating agent, flavor enhancer, and/or preservative. Citric acid can be an odorless, white crystalline powder and have a strong acidic taste. In addition to buffering, sodium citrate (e.g., anhydrous or dihydrate) can be used as an alkalizing agent, emulsifying agent, and/or sequestering agent. Sodium citrate dihydrate can be odorless, colorless, monoclinic crystals, or a white crystalline powder with a cooling, saline taste.

The concentration of citric acid and sodium citrate included in compositions according to the present disclosure can affect the pH of the solution, which can affect oxidation and hydrolysis rates of chlorpromazine hydrochloride and consequently the stability of chlorpromazine hydrochloride. Additionally, the efficacy of preservatives and palatability of the oral liquid compositions according to the present disclosure can be affected by the pH. Thus, in various non-limiting embodiments, the content of the citric acid and sodium citrate and the pH of the oral liquid compositions according to the present disclosure may be optimized to enhance stability of chlorpromazine hydrochloride, the efficacy of the preservatives, and palatability of the oral liquid composition.

In various non-limiting embodiments, oral liquid compositions according to the present disclosure comprise a sufficient concentration of citric acid and sodium citrate to provide a pH in a range of about 2.0 to about 5.0, such as, for example, about 2.5 to about 4.5, about 3.0 to about 4.5, about 3.5 to about 4.5, about 3.6 to about 4.4, about 3.7 to about 4.3, about 3.7 to about 4.2, about 3.7 to about 4.1, about 3.8 to about 4.0, or about 3.85 to about 3.95. In certain non-limiting embodiments, the oral liquid compositions according to the present disclosure comprise a sufficient amount of citric acid and sodium citrate to provide a pH of about 3.7, about 3.8, about 3.85, about 3.9, about 3.95, about 4.0, or about 4.1. For example, in various non-limiting embodiments, an oral liquid composition according to the present disclosure comprises a pH of about 3.9.

In various non-limiting embodiments, the oral liquid compositions according to the present disclosure comprise a citric acid content of no greater than about 5 mg/mL, such as, for example, no greater than about 4 mg/mL, no greater than about 3.5 mg/mL, no greater than about 3.4 mg/mL, no greater than about 3.39 mg/mL, no greater than about 3.35 mg/mL, no greater than about 3.3 mg/mL, no greater than about 3.2 mg/mL, no greater than about 3.0 mg/mL, no greater than about 2.0 mg/mL, no greater than about 1.5 mg/mL, no greater than about 1.1 mg/mL, no greater than about 1.05 mg/mL, or no greater than about 1 mg/mL, based on total volume of the composition. In certain non-limiting embodiments, oral liquid compositions according to the present disclosure comprise a citric acid content of at least about 0.05 mg/mL, such as, for example, at least about 0.1 mg/mL, at least about 0.5 mg/mL, at least about 0.8 mg/mL, at least about 0.9 mg/mL, at least about 0.95 mg/mL, at least about 1.0 mg/mL, at least about 1.05 mg/mL, at least about 1.1 mg/mL, at least about 1.5 mg/mL, at least about 2.0 mg/mL, at least about 3.0 mg/mL, at least about 3.2 mg/mL, or at least about 3.3 mg/mL, based on total volume of the composition. For example, in various non-limiting embodiments, oral liquid compositions according to the present disclosure comprise a citric acid content in a range of about 0.05 mg/mL to about 5.0 mg/mL, such as, for example, about 0.1 mg/mL to about 4 mg/mL, about 0.9 mg/mL to about 1.1 mg/mL, about 1.0 mg/mL to about 1.05 mg/mL, about 3.0 mg/mL to about 3.5 mg/mL, about 3.2 mg/mL to about 3.4 mg/mL, about 3.3 mg/mL to about 3.4 mg/mL, or about 3.35 mg/mL to about 3.4 mg/mL, based on total volume of the composition.

In certain non-limiting embodiments, oral liquid compositions according to the present disclosure comprise a citric acid content of about 1.0 mg/mL, about 1.018 mg/mL, about 3.393 mg/mL, or about 3.4 mg/mL, based on total volume of the composition. In certain non-limiting embodiments, an oral liquid composition according to the present disclosure comprises a citric acid content of about 1.018 mg/mL and a chlorpromazine hydrochloride content of about 30 mg/mL. In certain non-limiting embodiments, an oral liquid composition according to the present disclosure can comprise a citric acid content of about 3.393 mg/mL and a chlorpromazine hydrochloride content of about 100 mg/mL.

In various non-limiting embodiments, oral liquid compositions according to the present disclosure comprise a chlorpromazine hydrochloride to citric acid weight ratio in a range of about 100:1 to about 1:1, such as, for example, about 75:1 to about 2:1, about 60:1 to about 5:1, about 50:1 to about 10:1, about 40:1 to about 20:1, about 35:1 to about 25:1, or about 31:1 to about 29:1. In certain non-limiting embodiments, the oral liquid compositions according to the present disclosure can comprise a chlorpromazine hydrochloride to citric acid weight ratio of about 29:1, about 29.5:1, or about 30:1.

In various non-limiting embodiments, oral liquid compositions according to the present disclosure comprise a chlorpromazine hydrochloride to citric acid mole ratio in a range of about 100:1 to about 1:1, such as, for example, about 75:1 to about 2:1, about 60:1 to about 5:1, about 50:1 to about 5:1, about 30:1 to about 10:1, about 20:1 to about 10:1, or about 18:1 to about 16:1.

In certain non-limiting embodiments, oral liquid compositions according to the present disclosure comprise a chlorpromazine hydrochloride to citric acid mole ratio of about 17:1, about 18:1, or about 19:1.

In various non-limiting embodiments, oral liquid compositions according to the present disclosure can comprise a sodium citrate content no greater than about 10 mg/mL, such as, for example, no greater than about 7 mg/mL, no greater than about 6 mg/mL, no greater than about 5.5 mg/mL, no greater than about 5.3 mg/mL, no greater than about 5.25 mg/mL, no greater than about 5.21 mg/mL, no greater than about 5.2 mg/mL, no greater than about 5.1 mg/mL, no greater than about 5.0 mg/mL, no greater than about 2.0 mg/mL, no greater than about 1.75 mg/mL, no greater than about 1.6 mg/mL, or no greater than about 1.57 mg/mL. In certain non-limiting embodiments, oral liquid compositions according to the present disclosure can comprise a sodium citrate content of at least about 0.1 mg/mL, such as, for example, at least about 0.5 mg/mL, at least about 1.0 mg/mL, at least about 1.4 mg/mL, at least about 1.5 mg/mL, at least about 1.55 mg/mL, at least about 1.57 mg/mL, at least about 1.6 mg/mL, at least about 1.75 mg/mL, at least about 2.0 mg/mL, at least about 5.0 mg/mL, or at least about 5.25 mg/mL, based on total volume of the composition. For example, in various non-limiting embodiments, oral liquid compositions according to the present disclosure comprise a sodium citrate content in a range of about 0.1 mg/mL to about 10.0 mg/mL, such as, for example, about 0.5 mg/mL to about 7 mg/mL, about 1.4 mg/mL to about 1.7 mg/mL, about 1.5 mg/mL to about 1.6 mg/mL, about 1.55 mg/mL to about 1.57 mg/mL, about 5.0 mg/mL to about 5.5 mg/mL, about 5.1 mg/mL to about 5.4 mg/mL, about 5.2 mg/mL to about 5.3 mg/mL, or about 5.2 mg/mL to about 5.25 mg/mL, based on total volume of the composition. In certain non-limiting embodiments, oral liquid compositions according to the present disclosure comprise a sodium citrate content of about 1.5 mg/mL, about 1.566 mg/mL, about 5.2 mg/mL, or about 5.220 mg/mL. In certain non-limiting embodiments, an oral liquid composition according to the present disclosure comprises a sodium citrate content of about 1.566 mg/mL and a chlorpromazine hydrochloride content of about 30 mg/mL. In certain non-limiting embodiments, an oral liquid composition according to the present disclosure comprises a sodium citrate content of about 5.220 mg/mL and a chlorpromazine hydrochloride content of about 100 mg/mL.

In various non-limiting embodiments, oral liquid compositions according to the present disclosure comprise a chlorpromazine hydrochloride to sodium citrate weight ratio in a range of about 100:1 to about 1:1, such as, for example, about 75:1 to about 2:1, about 50:1 to about 5:1, about 40:1 to about 5:1, about 30:1 to about 10:1, about 25:1 to about 15:1, or about 20:1 to about 19:1. In certain non-limiting embodiments, oral liquid compositions according to the present disclosure comprise a chlorpromazine hydrochloride to sodium citrate weight ratio of about 19:1, about 20:1, or about 21:1.

In various non-limiting embodiments, oral liquid compositions according to the present disclosure comprise a chlorpromazine hydrochloride to sodium citrate mole ratio in a range of about 100:1 to about 1:1, such as, for example, about 75:1 to about 2:1, about 60:1 to about 5:1, about 50:1 to about 5:1, about 30:1 to about 10:1, about 20:1 to about 10:1, or about 18:1 to about 16:1. In certain non-limiting embodiments, oral liquid compositions according to the present disclosure comprise a chlorpromazine hydrochloride to sodium citrate mole ratio of about 17:1, about 18:1, or about 19:1.

In various non-limiting embodiments, oral liquid compositions according to the present disclosure comprise a sodium citrate to citric acid weight ratio in a range of about 20:1 to about 0.1:1, such as, for example, about 10:1 to about 0.5:1, about 5:1 to about 0.5:1, about 4:1 to about 0.75:1, about 3:1 to about 0.75:1, or about 2:1 to about 1:1. In certain non-limiting embodiments, oral liquid compositions according to the present disclosure comprise a sodium citrate to citric acid weight ratio of 1:1, 1.5:1, or 2:1.

In various non-limiting embodiments, oral liquid compositions according to the present disclosure comprise a sodium citrate to citric acid mole ratio in a range of about 10:1 to about 0.1:1, such as, for example, about 5:1 to about 0.5:1, about 4:1 to about 0.6:1, about 3:1 to about 0.7:1, about 2:1 to about 0.8:1, or about 1.1:1 to about 0.9:1. In certain non-limiting embodiments, oral liquid compositions according to the present disclosure comprise a sodium citrate to citric acid mole ratio of about 0.9:1, about 1:1, or about 1.1:1.

Chelating Agent

Chlorpromazine hydrochloride can be sensitive to oxidation and/or discoloration caused by foreign matter in the solution. Thus, various non-limiting embodiments of oral liquid compositions according to the present disclosure can comprise a chelating agent to inhibit discoloration and/or enhance stability of the compositions caused by foreign matter in the solution. In various non-limiting embodiments, the chelating agent comprises at least one of ethylenediaminetetraacetic acid (EDTA), diethylenetriaminepentaacetic acid (DTPA), deferoxamine, deferasirox, deferiprone, pyridoxal isonicotinoyl hydrazone, rhodotorulic acid, picolinic acid, nicotinic acid, neoaspergillic acid, methionine, lactic acid, N,N-ethylene bis[N-phopsphonomethyl]glycine, tetraethylenepentaamine heptaacetic acid (TPHA), tri(2-aminoethyl)aminehexaacetic acid (TAAHA), triethylenetetraaminehexaacetic acid (TTHA), oxybis(ethylenenitrilo) tetraacetic acid (BAETA), trans-1,2-cyclohexaneediaminetetraacetic acid, salicyclic acid, tartaric acid, 2,3-dihydroxybenzoic acid, penicillamine, etidronic acid (1-hydroxyethan-1,1-diyl)bis(phosphonic acid), dimercaptosuccinic acid, dimercapto-propane sulfonate, and dimercaprol, desferrithiocin (DFT), polycarboxylates, hydroxamates, catecholates, hydroxypyridonates, teraphthalamides, analogues thereof, and derivatives thereof. In certain non-limiting embodiments, the chelating agent can be EDTA, such as, for example, disodium edetate.

Chlorpromazine hydrochloride can be oxidized to impurity A initiated through a catalysis reaction with heavy metal ions. The chelating agent can form stable water-soluble complexes (chelates) with alkaline earth and heavy metal ions. The chelated form has few of the properties of the free ion and thus can remove heavy metal ions from solution. Therefore, the chelating agent can prevent heavy metal catalyzed oxidation of chlorpromazine hydrochloride by sequestering the heavy metal ions in the solution. The amount of chelating agent added in non-limiting embodiments of oral liquid compositions according to the present disclosure can provide a concentration of the chelating agent effective to sequester a desired concentration of metal ions in solution, while limiting interaction between the chelating agent and the chlorpromazine hydrochloride in the composition.

In various non-limiting embodiments, oral liquid compositions according to the present disclosure comprise a chelating agent content no greater than about 10 mg/mL, such as, for example, no greater than about 5 mg/mL, no greater than about 4 mg/mL, no greater than about 3 mg/mL, no greater than about 2 mg/mL, no greater than about 1.5 mg/mL, no greater than about 1.25 mg/mL, no greater than about 1.1 mg/mL, or no greater than about 1 mg/mL, based on total volume of the composition. In certain non-limiting embodiments, oral liquid compositions according to the present disclosure comprise a chelating agent content of at least about 0.05 mg/mL, such as, for example, at least about 0.1 mg/mL, at least about 0.5 mg/mL, at least about 0.8 mg/mL, at least about 0.9 mg/mL, at least about 0.95 mg/mL, or at least about 1.0 mg/mL, based on total volume of the composition. For example, in various non-limiting embodiments, oral liquid compositions according to the present disclosure comprise a chelating agent content in a range of about 0.05 mg/mL to about 10.0 mg/mL, such as, for example, about 0.1 mg/mL to about 5 mg/mL, about 0.5 mg/mL to about 2 mg/mL, about 0.8 mg/mL to about 1.25 mg/mL, or about 0.9 mg/mL to about 1.1 mg/mL, based on total volume of the composition. In certain non-limiting embodiments, oral liquid compositions according to the present disclosure comprise a chelating agent content of about 0.9 mg/mL, about 1.0 mg/mL, or about 1.1 mg/mL. In certain non-limiting embodiments, an oral liquid composition according to the present disclosure comprises a chelating agent content of about 1.0 mg/mL and a chlorpromazine content of about 30 mg/mL or about 100 mg/mL, based on total volume of the composition.

In various non-limiting embodiments, oral liquid compositions according to the present disclosure comprise a chlorpromazine to chelating agent weight ratio in a range of about 500:1 to about 1:1, such as, for example, about 300:1 to about 10:1, about 200:1 to about 50:1, about 200:1 to about 75:1, about 125:1 to about 75:1, about 110:1 to about 90:1, or about 101:1 to about 99:1. In certain non-limiting embodiments, an oral liquid composition according to the present disclosure can comprise a chlorpromazine to chelating agent weight ratio of about 100:1.

In various non-limiting embodiments, oral liquid compositions according to the present disclosure comprise a chlorpromazine to chelating agent mole ratio in a range of about 500:1 to about 1:1, such as, for example, about 300:1 to about 10:1, about 200:1 to about 50:1, about 200:1 to about 75:1, about 125:1 to about 75:1, about 110:1 to about 90:1, about 106:1 to about 104:1, about 50:1 to about 10:1, 40:1 to about 20:1, about 35:1 to about 25:1, or about 33:1 to about 31:1. In certain non-limiting embodiments, the oral liquid compositions according to the present disclosure comprise a chlorpromazine to chelating agent mole ratio of about 31:1, about 32:1, or about 33:1.

In various non-limiting embodiments, oral liquid compositions according to the present disclosure comprise an disodium edetate content no greater than about 10 mg/mL, such as, for example, no greater than about 5 mg/mL, no greater than about 4 mg/mL, no greater than about 3 mg/mL, no greater than about 2 mg/mL, no greater than about 1.5 mg/mL, no greater than about 1.25 mg/mL, no greater than about 1.1 mg/mL, or no greater than about 1 mg/mL, based on total volume of the composition. In certain non-limiting embodiments, oral liquid compositions according to the present disclosure comprise a disodium edetate content of at least about 0.05 mg/mL, such as, for example, at least about 0.1 mg/mL, at least about 0.5 mg/mL, at least about 0.8 mg/mL, at least about 0.9 mg/mL, at least about 0.95 mg/mL, or at least about 1.0 mg/mL, based on total volume of the composition. For example, in various non-limiting embodiments, oral liquid compositions according to the present disclosure comprise a disodium edetate content in a range of about 0.05 mg/mL to about 10.0 mg/mL, such as, for example, about 0.1 mg/mL to about 5 mg/mL, about 0.5 mg/mL to about 2 mg/mL, about 0.8 mg/mL to about 1.25 mg/mL, or about 0.9 mg/mL to about 1.1 mg/mL, based on total volume of the composition. In certain non-limiting embodiments, oral liquid compositions according to the present disclosure comprise a disodium edetate content of about 0.9 mg/mL, about 1.0 mg/mL, or about 1.1 mg/mL, based on total volume of the composition. In certain non-limiting embodiments, an oral liquid composition according to the present disclosure comprises a disodium edetate content of about 1.0 mg/mL and a chlorpromazine hydrochloride content of about 30 mg/mL or about 100 mg/mL.

In various non-limiting embodiments, oral liquid compositions according to the present disclosure comprise a chlorpromazine hydrochloride to disodium edetate weight ratio in a range of about 500:1 to about 1:1, such as, for example, about 300:1 to about 10:1, about 200:1 to about 50:1, about 200:1 to about 75:1, about 125:1 to about 75:1, about 110:1 to about 90:1, or about 101:1 to about 99:1. In certain non-limiting embodiments, oral liquid compositions according to the present disclosure comprise a chlorpromazine hydrochloride to disodium edetate weight ratio of about 100:1.

In various non-limiting embodiments, oral liquid compositions according to the present disclosure comprise a chlorpromazine hydrochloride to disodium edetate mole ratio in a range of about 500:1 to about 1:1, such as, for example, about 500:1 to about 10:1, about 200:1 to about 50:1, about 200:1 to about 75:1, about 125:1 to about 75:1, about 110:1 to about 90:1, about 106:1 to about 104:1, about 50:1 to about 10:1, about 40:1 to about 20:1, about 35:1 to about 25:1, or about 33:1 to about 31:1. In certain non-limiting embodiments, an oral liquid composition according to the present disclosure comprises a chlorpromazine hydrochloride to disodium edetate mole ratio of about 31:1, about 32:1, or about 33:1.

Solvent

The oral liquid compositions according to the present disclosure can comprise a solvent (e.g., liquid carrier). The solvent can provide desired qualities to the oral liquid compositions according to the present disclosure, such as, for example, clarity, nontoxicity, acceptable viscosity, compatibility with excipients, chemical inertness, palatability, acceptable odor and color, and economy. The solvent can include at least one of water, ethyl alcohol, glycerin, propylene glycol, syrup (e.g., sugar or other sweetener based substance, such as, for example, ORA-SWEET™ SF sugar-free flavored syrup), juices (e.g., apple, grape, orange, cranberry, cherry, tomato and the like), other beverages (e.g., tea, coffee, soft drinks, milk and the like), oils (e.g., olive, soybean, corn, mineral, castor and the like), and combinations or mixtures thereof. Certain solvents can be combined to form emulsions for inclusion in the oral liquid compositions. In some non-limiting embodiments, the solvent comprises water (e.g., purified water). In certain non-limiting embodiments, the solvent comprises a syrup. In various non-limiting embodiments, the solvent comprises a juice.

The solvent in the oral liquid compositions can be added in a content effective to dissolve other excipients and create a homogeneous solution. Incomplete dissolution of ingredients may result in retention of undissolved particles in the product which can require excessive mixing, effect the pH of the composition, and affect microbial growth within the composition, which can affect the stability of the oral liquid composition.

In various non-limiting embodiments, solvent can be added to the oral liquid compositions according to the present disclosure to achieve a solids content of no greater than about 500 mg/mL, such as, for example, no greater than about 450 mg/mL, no greater than about 400 mg/mL, no greater than about 300 mg/mL, no greater than about 200 mg/mL, no greater than about 175 mg/mL, no greater than about 150 mg/mL, no greater than about 100 mg/mL, no greater than about 60 mg/mL, no greater than about 50 mg/mL, or no greater than about 45 mg/mL, based on the total volume of the composition. In certain non-limiting embodiments, the solvent can be added to oral liquid compositions according to the present disclosure to achieve a solids content of at least about 5 mg/mL, such as, for example, at least about 10 mg/mL, at least about 30 mg/mL, at least about 35 mg/mL, at least about 40 mg/mL, at least about 50 mg/mL, at least about 60 mg/mL, at least about 100 mg/mL, at least about 120 mg/mL, at least about 130 mg/mL, or at least about 135 mg/mL, based on total volume of the composition. For example, in various non-limiting embodiments, the solvent can be added to oral liquid compositions according to the present disclosure to achieve a solids content in a range of about 5 mg/mL to about 500 mg/mL, such as, for example, about 10 mg/mL to about 200 mg/mL, about 30 mg/mL to about 50 mg/mL, about 35 mg/mL to about 45 mg/mL, about 100 mg/mL to about 200 mg/mL, about 120 mg/mL to about 160 mg/mL, about 130 mg/mL to about 150 mg/mL, or about 135 mg/mL to about 145 mg/mL, based on total volume of the composition. In certain non-limiting embodiments, the solvent can be added to oral liquid compositions according to the present disclosure to achieve a solids content of about 42.9 mg/mL or about 140.6 mg/mL. In certain non-limiting embodiments, the solvent can be added to an oral liquid composition according to the present disclosure to achieve a solids content of about 42.9 mg/mL and a chlorpromazine content of about 30 mg/mL. In certain non-limiting embodiments, the solvent can be added to an oral liquid composition according to the present disclosure to achieve a solids content of about 140.6 mg/mL and a chlorpromazine content of about 100 mg/mL.

In various non-limiting embodiments, oral liquid compositions according to the present disclosure can comprise a solvent content of no greater than about 1000 mg/mL, such as, for example, no greater than about 995 mg/mL, no greater than about 975 mg/mL, no greater than about 970 mg/mL, no greater than about 968 mg/mL, no greater than about 965 mg/mL, no greater than about 960 mg/mL, no greater than about 950 mg/mL, no greater than about 925 mg/mL, no greater than about 910 mg/mL, or no greater than about 900 mg/mL, based on total volume of the composition. In certain non-limiting embodiments, oral liquid compositions according to the present disclosure can comprise a solvent content of at least about 500 mg/mL, such as, for example, at least about 750 mg/mL, at least about 800 mg/mL, at least about 850 mg/mL, at least about 875 mg/mL, at least about 890 mg/mL, at least about 895 mg/mL, at least about 900 mg/mL, at least about 910 mg/mL, at least about 925 mg/mL, at least about 950 mg/mL, or at least about 960 mg/mL, based on total volume of the composition. For example, in various non-limiting embodiments, oral liquid compositions according to the present disclosure can comprise a solvent content in a range of about 500 mg/mL to about 1000 mg/mL, such as, for example, about 750 mg/mL to about 975 mg/mL, about 965 mg/mL to about 970 mg/mL, or about 895 mg/mL to about 905 mg/mL, based on total volume of the composition. In certain non-limiting embodiments, an oral liquid composition according to the present disclosure can comprise a solvent content of about 968 mg/mL or about 898 mg/mL. In certain non-limiting embodiments, an oral liquid composition according to the present disclosure can comprise a solvent content of about 968 mg/mL and a chlorpromazine content of about 30 mg/mL. In certain non-limiting embodiments, an oral liquid composition according to the present disclosure can comprise a solvent content of about 898 mg/mL and a chlorpromazine content of about 100 mg/mL.

In various non-limiting embodiments, water can be added to oral liquid compositions according to the present disclosure to achieve a solids content no greater than about 500 mg/mL, such as, for example, no greater than about 450 mg/mL, no greater than about 400 mg/mL, no greater than about 300 mg/mL, no greater than about 200 mg/mL, no greater than about 175 mg/mL, no greater than about 150 mg/mL, no greater than about 100 mg/mL, no greater than about 60 mg/mL, no greater than about 50 mg/mL, or no greater than about 45 mg/mL, based on total volume of the composition. In certain non-limiting embodiments, water can be added to oral liquid compositions according to the present disclosure to achieve a solids content of at least about 5 mg/mL, such as, for example, at least about 10 mg/mL, at least about 30 mg/mL, at least about 35 mg/mL, at least about 40 mg/mL, at least about 50 mg/mL, at least about 60 mg/mL, at least about 100 mg/mL, at least about 120 mg/mL, at least about 130 mg/mL, or at least about 135 mg/mL, based on total volume of the composition. For example, in various non-limiting embodiments, water can be added to oral liquid compositions according to the present disclosure to achieve a solids content in a range of about 5 mg/mL to about 500 mg/mL, such as, for example, about 10 mg/mL to about 200 mg/mL, about 30 mg/mL to about 50 mg/mL, about 35 mg/mL to about 45 mg/mL, about 100 mg/mL to about 200 mg/mL, about 120 mg/mL to about 160 mg/mL, about 130 mg/mL to about 150 mg/mL, or about 135 mg/mL to about 145 mg/mL, based on total volume of the composition. In certain non-limiting embodiments, water can be added to an oral liquid composition according to the present disclosure to achieve a solids content of about 42.9 mg/mL or about 140.6 mg/mL. In certain non-limiting embodiments, water can be added to thane oral liquid composition according to the present disclosure to achieve a solids content of about 42.9 mg/mL and a chlorpromazine hydrochloride content of about 30 mg/mL. In certain non-limiting embodiments, water can be added to an oral liquid composition according to the present disclosure to achieve a solids content of about 140.6 mg/mL and a chlorpromazine hydrochloride content of about 100 mg/mL.

In various non-limiting embodiments, oral liquid compositions according to the present disclosure can comprise a water content no greater than about 1000 mg/mL, such as, for example, no greater than about 995 mg/mL, no greater than about 975 mg/mL, no greater than about 970 mg/mL, no greater than about 968 mg/mL, no greater than about 965 mg/mL, no greater than about 960 mg/mL, no greater than about 950 mg/mL, no greater than about 925 mg/mL, no greater than about 910 mg/mL, or no greater than about 900 mg/mL, based on total volume of the composition. In certain non-limiting embodiments, the oral liquid compositions according to the present disclosure can comprise a water content of at least about 500 mg/mL, such as, for example, at least about 750 mg/mL, at least about 800 mg/mL, at least about 850 mg/mL, at least about 875 mg/mL, at least about 890 mg/mL, at least about 895 mg/mL, at least about 900 mg/mL, at least about 910 mg/mL, at least about 925 mg/mL, at least about 950 mg/mL, or at least about 960 mg/mL, based on total volume of the composition. For example, in various non-limiting embodiments, oral liquid compositions according to the present disclosure comprise a water content in a range of about 500 mg/mL to about 1000 mg/mL, such as, for example, about 750 mg/mL to about 975 mg/mL, about 965 mg/mL to about 970 mg/mL, or about 895 mg/mL to about 905 mg/mL, based on total volume of the composition. In certain non-limiting embodiments, an oral liquid composition according to the present disclosure comprises a water content of about 968 mg/mL or about 898 mg/mL. In certain non-limiting embodiments, an oral liquid composition according to the present disclosure comprises a water content of about 968 mg/mL and a chlorpromazine hydrochloride content of about 30 mg/mL. In certain non-limiting embodiments, an oral liquid composition according to the present disclosure comprises a water content of about 898 mg/mL and a chlorpromazine hydrochloride content of about 100 mg/mL.

Sweetener

In various non-limiting embodiments, oral liquid compositions according to the present disclosure can comprise additional excipients, such as, for example, one or more of a sweetener, a flavoring agent, a stabilizer, a coloring agent, an antioxidant, and a thickener. Additional excipients can be selected based on function and compatibility with the oral liquid compositions disclosed herein and may be found, for example, in Remington: The Science and Practice of Pharmacy, Nineteenth Ed. (Easton, Pa.: Mack Publishing Company, 1995); Hoover, John E., Remington's Pharmaceutical Sciences, (Easton, Pa.: Mack Publishing Company, 1975); Liberman, H. A. and Lachman, L., Eds., Pharmaceutical Dosage Forms (New York, N.Y.: Marcel Decker, 1980); and Pharmaceutical Dosage Forms and Drug Delivery Systems, Seventh Ed. (Lippincott Williams & Wilkins, 1999), Kibbe, Arthur H., "Handbook of Pharmaceutical Excipients" (3rd ed.) (2000), all of which are herein incorporated by reference in their entireties. In various non-limiting embodiments, the oral liquid compositions according to the present disclosure comprises a sweetener, optionally a flavoring agent, and optionally a coloring agent.

The sweetener can comprise a compound that can provide a sweet taste, such as, for example, natural and synthetic sugars, natural and artificial sweeteners, natural extracts and any material that initiates a sweet sensation in a subject. In some non-limiting embodiments, the sweetener can be solid or liquid. The sweetener can comprise, for example, at least one of glucose, fructose, sucrose, xylitol, tagatose, sucralose, maltitol, isomaltulose, ISOMALT™ (hydrogenated isomaltulose), lactitol, sorbitol, mannitol, erythritol, trehalose, maltodextrin, polydextrose, and the like. Other sweeteners that may be included in the compositions herein include, for example, glycerin, inulin, erythritol, maltol, acesulfame and salts thereof (e.g., acesulfame potassium), alitame, aspartame, neotame, cyclamates (e.g., sodium cyclamate), saccharin and salts thereof (e.g., saccharin sodium or saccharin calcium), neohesperidin dihydrochalcone, stevioside, thaumatin, and the like. The sweetener(s) can be used in the form of crude or refined products, such as, for example, hydrogenated starch hydrolysates, maltitol syrup, high fructose corn syrup, etc., and as branded products, e.g., SWEET AM™ liquid (Product Code 918.003—propylene glycol, ethyl alcohol, and proprietary artificial flavor combination, Flavors of North America), SWEET AM™ powder (Product Code 918.005—maltodextrin, sorbitol, and fructose combination and Product Code 918.010—water, propylene glycol, sorbitol, fructose, and proprietary natural and artificial flavor combination, Flavors of North America), PROSWEET™ product (about 1-10/a proprietary plant/vegetable extract and about 90-99% dextrose combination, Virginia Dare), MALTISWEET™ product (maltitol solution, Ingredion) and SORBO™ product (sorbitol and sorbitol/xylitol solution, SPI Polyols), INVERTOSE™ syrup (high fructose corn syrup, Ingredion), and ORA-SWEET™ sugar-free flavored syrup (Paddock Laboratories, Inc.). In various non-limiting embodiments, sugar added to compositions herein can comprise at least one of a monosaccharide, a disaccharide, and a polysaccharide. For example, in various non-limiting embodiments, sugar added to compositions herein can comprise at least one of xylose, ribose, glucose, mannose, galactose, fructose, dextrose, sucrose, maltose, partially hydrolyzed starch or corn syrup, and sugar alcohols such as sorbitol, xylitol, mannitol, and glycerin.

In some non-limiting embodiments, sweetener added to a composition herein comprises sucralose. Sucralose is an artificial sweetener suitable for oral liquid formulations. Sucralose can be a white to off-white colored, free-flowing, crystalline powder. Because solutions comprising chlorpromazine hydrochloride can have an extremely bitter taste, a sweetener may be added to achieve a desired palatability. Sucralose has a sweetening power approximately about 300-1000 times that of sucrose, with minimal, if any, aftertaste. Thus, utilizing sucralose can minimize the total weight of excipients added to oral liquid compositions according to the present disclosure, which can enhance stability of the chlorpromazine hydrochloride.

In various non-limiting embodiments, oral liquid compositions according to the present disclosure comprise a sweetener content no greater than about 200 mg/mL, such as, for example, no greater than about 100 mg/mL, no greater than about 75 mg/mL, no greater than about 50 mg/mL, no greater than about 40 mg/mL, no greater than about 35 mg/mL, no greater than about 30 mg/mL, no greater than about 25 mg/mL, no greater than about 20 mg/mL, no greater than about 15 mg/mL, no greater than about 10 mg/mL, or no greater than about 9 mg/mL, based on total volume of the composition. In certain non-limiting embodiments, oral liquid compositions according to the present disclosure can comprise a sweetener content of at least about 1 mg/mL, such as, for example, at least about 5 mg/mL, at least about 7 mg/mL, at least about 8 mg/mL, at least about 9 mg/mL, at least about 10 mg/mL, at least about 15 mg/mL, at least about 20 mg/mL, at least about 25 mg/mL, or at least about 30 mg/mL, based on total volume of the composition. For example, in various non-limiting embodiments, oral liquid compositions according to the present disclosure can comprise a sweetener content in a range of about 1 mg/mL to about 200 mg/mL, such as, for example, about 5 mg/mL to about 50 mg/mL, about 5 mg/mL to about 15 mg/mL, about 8 mg/mL to about 10 mg/mL, or about 25 mg/mL to about 35 mg/mL, based on total volume of the composition. In certain non-limiting embodiments, an oral liquid composition according to the present disclosure can comprise a sweetener content of about 9 mg/mL or about 30 mg/mL. In certain non-limiting embodiments, an oral liquid composition according to the present disclosure can comprise a sweetener content of about 9.0 mg/mL and a chlorpromazine content of about 30 mg/mL. In certain non-limiting embodiments, an oral liquid composition according to the present disclosure can comprise a sweetener content of about 30.0 mg/mL and a chlorpromazine content of about 100 mg/mL.

In various non-limiting embodiments, oral liquid compositions according to the present disclosure can comprise a chlorpromazine to sweetener weight ratio in a range of about 50:1 to about 0.5:1, such as, for example, about 25:1 to about 1:1, about 20:1 to about 1:1, about 10:1 to about 1:1, about 5:1 to about 1:1, about 4:1 to about 2:1, or about 3.5:1 to about 3:1. In certain non-limiting embodiments, an oral liquid composition according to the present disclosure can comprise a chlorpromazine to sweetener weight ratio of about 3.3:1.

In various non-limiting embodiments, oral liquid compositions according to the present disclosure comprise a chlorpromazine to sweetener mole ratio in a range of about 50:1 to about 0.1:1, such as, for example, about 25:1 to about 0.5:1, about 20:1 to about 1:1, about 10:1 to about 1:1, about 8:1 to about 2:1, about 7:1 to about 3:1, or about 5:1 to about 3:1. In certain non-limiting embodiments, an oral liquid composition according to the present disclosure comprises a chlorpromazine to sweetener mole ratio of about 4:1 or about 5:1.

In various non-limiting embodiments, oral liquid compositions according to the present disclosure comprise a sucralose content no greater than about 200 mg/mL, such as, for example, no greater than about 100 mg/mL, no greater than about 75 mg/mL, no greater than about 50 mg/mL, no greater than about 40 mg/mL, no greater than about 35 mg/mL, no greater than about 30 mg/mL, no greater than about 25 mg/mL, no greater than about 20 mg/mL, no greater than about 15 mg/mL, no greater than about 10 mg/mL, or no greater than about 9 mg/mL, based on total volume of the composition. In certain non-limiting embodiments, oral liquid compositions according to the present disclosure comprise a sucralose content of at least about 1 mg/mL, such as, for example, at least about 5 mg/mL, at least about 7 mg/mL, at least about 8 mg/mL, at least about 9 mg/mL, at least about 10 mg/mL, at least about 15 mg/mL, at least about 20 mg/mL, at least about 25 mg/mL, or at least about 30 mg/mL, based on total volume of the composition.

For example, in various non-limiting embodiments, oral liquid compositions according to the present disclosure comprise a sucralose content in a range of about 1 mg/mL to about 200 mg/mL, such as, for example, about 5 mg/mL to about 50 mg/mL, about 5 mg/mL to about 15 mg/mL, about 8 mg/mL to about 10 mg/mL, or about 25 mg/mL to about 35 mg/mL, based on total volume of the composition. In certain non-limiting embodiments, an oral liquid composition according to the present disclosure comprises a sucralose content of about 9 mg/mL or about 30 mg/mL. In certain non-limiting embodiments, an oral liquid composition according to the present disclosure comprises a sucralose content of about 9.0 mg/mL and a chlorpromazine hydrochloride content of about 30 mg/mL. In certain non-limiting embodiments, an oral liquid composition according to the present disclosure comprises a sucralose content of about 30.0 mg/mL and a chlorpromazine hydrochloride content of about 100 mg/mL.

In various non-limiting embodiments, oral liquid compositions according to the present disclosure comprise a chlorpromazine hydrochloride to sucralose weight ratio in a range of about 50:1 to about 0.5:1, such as, for example, about 25:1 to about 1:1, about 20:1 to about 1:1, about 10:1 to about 1:1, about 5:1 to about 1:1, about 4:1 to about 2:1, or about 3.5:1 to about 3:1. In certain non-limiting embodiments, an oral liquid composition according to the present disclosure can comprise a chlorpromazine hydrochloride to sucralose weight ratio of about 3.3:1.

In various non-limiting embodiments, oral liquid compositions according to the present disclosure can comprise a chlorpromazine hydrochloride to sucralose mole ratio in a range of about 50:1 to about 0.1:1, such as, for example, about 25:1 to about 0.5:1, about 20:1 to about 1:1, about 10:1 to about 1:1, about 8:1 to about 2:1, about 7:1 to about 3:1, or about 5:1 to about 3:1. In certain non-limiting embodiments, an oral liquid composition according to the present disclosure can comprise a chlorpromazine hydrochloride to sucralose mole ratio of about 4:1 or about 5:1.

Additional Excipients

In certain non-limiting embodiments, oral liquid compositions according to the present disclosure can comprise a coloring agent. The coloring agent can be used for identification and/or aesthetic purposes. The coloring agent can comprise, for example, at least one of FD&C Red No. 3, FD&C Red No. 20, FD&C Red No. 40, FD&C Yellow No. 6, FD&C Blue No. 2, D&C Green No. 5, D&C Orange No. 5, caramel, ferric oxide, or mixtures thereof.

In certain non-limiting embodiments, oral liquid compositions according to the present disclosure can comprise a flavoring agent. The flavoring agent can be used to enhance the taste and/or aroma of the oral liquid composition according to the present disclosure. A natural and/or synthetic flavoring agent can be selected from standard reference books, for example Fenaroli's Handbook of Flavor Ingredients, 3rd edition (1995). Natural flavoring agents can comprise at least one of almond, anise, apple, apricot, bergamot, blackberry, blackcurrant, blueberry, cacao, caramel, cherry, cinnamon, clove, coffee, coriander, cranberry, cumin, dill, *eucalyptus*, fennel, fig, ginger, grape, grapefruit, guava, hop, lemon, licorice, lime, malt, mandarin, molasses, nutmeg, orange, peach, pear, peppermint, pineapple, raspberry, rose, spearmint, strawberry, tangerine, tea, tutti-frutti, vanilla, wintergreen, and the like. In certain non-limiting embodiments, flavoring agents that may be included in the oral liquid compositions include cherry, grape, orange, and bubblegum. In some non-limiting embodiments, the oral liquid composition comprises an orange flavoring agent.

In some non-limiting embodiments, oral liquid compositions according to the present disclosure comprise a flavoring agent content in a range of about 1 mg/mL to about 5 mg/mL, such as, for example, about 1.4 mg/mL to about 3 mg/mL, about 2 mg/mL to about 4 mg/mL, about 2.2 mg/mL to about 3.7 mg/mL, about 2.5 mg/mL to about 3.5 mg/mL, or about 2.8 mg/mL to about 3.7 mg/mL, based on total volume of the composition.

In various non-limiting embodiments, liquid oral compositions according to the present disclosure comprise at least one of a flavoring agent selected from FN-924 Natural and Artificial Orange Flavor and a coloring agent comprising FD&C Yellow #6. FN-924 Natural and Artificial Orange Flavor comprises propylene glycol, triacetin, natural and artificial flavor, and ethanol. FN-924 Natural and Artificial Orange Flavor is approved as GRAS (Generally Recognized as Safe) by the FDA and FEMA.

Stability

Oral liquid compositions according to the present disclosure are stable for a minimum period of time under various storage conditions, including refrigerated and ambient conditions. As used herein, the term "stable" refers to the characteristic that the oral liquid composition retains at least about 90%, at least about 95%, or at least about 98% of an initial chlorpromazine content at the end of a given storage period under specified storage conditions. The term "stable"

can also refer to an oral liquid composition comprising an impurity A content of no greater than about 5% based on the total weight of the composition, such as, for example, no greater than about 4%, no greater than about 3%, no greater than about 2%, no greater than about 1%, no greater than about 0.75%, no greater than about 0.58%, or no greater than about 0.5%, based on the total weight of the composition, at the end of a given storage period under specified storage conditions. The term "stable" can also refer to an oral liquid composition having less than about $10^2$ total aerobic microbial count at the end of a given storage period under specified storage conditions. The term "stable" can also refer to an oral liquid composition having less than about 101 total combined yeast and mold count at the end of a given storage period under specified storage conditions. The term "stable" can also refer to the absence or non-detection of *Escherichia coli* and/or *Burkholderia cepacia* within the oral liquid composition following a given storage period under specified storage conditions.

In non-limiting embodiments according to the present disclosures, oral liquid compositions comprising chlorpromazine according to the present disclosure, stored under ambient (CRT) or refrigerated conditions for a specified storage period, may provide similar, consistent, or equivalent pharmacokinetic parameters as an oral liquid composition that is formulated immediately prior to administration to a subject (i.e., freshly made). For example, various embodiments of oral liquid compositions disclosed herein exhibit high stability after a specified storage period so as to provide similar, consistent, or equivalent pharmacokinetic parameters as a freshly made oral liquid composition. Pharmacokinetic parameters for chlorpromazine include $C_{max}$, $T_{max}$, $AUC_{last}$, $AUC_{inf}$, $T_{1/2}$, and $C_{last}$.

FORMULATION EXAMPLES

In various non-limiting embodiments, a liquid oral composition according to the present disclosure can comprise chlorpromazine hydrochloride, sucralose, sodium benzoate, sodium citrate, citric acid, disodium edetate, and water. For example, the liquid oral composition can comprise, based on total volume of the composition, about 1.0 mg/mL to about 200.0 mg/mL chlorpromazine hydrochloride, about 1 mg/mL to about 200 mg/mL sucralose, about 0.05 mg/mL to about 5.0 mg/mL sodium benzoate, about 0.1 mg/mL to about 10.0 mg/mL sodium citrate, about 0.05 mg/mL to about 5.0 mg/mL citric acid, about 0.05 mg/mL to about 10.0 mg/mL disodium edetate, and water. In various non-limiting embodiments, the liquid oral composition can consist essentially of chlorpromazine hydrochloride, sucralose, sodium benzoate, sodium citrate, citric acid, disodium edetate, water, optionally a flavoring agent, and optionally a coloring agent. In various non-limiting embodiments, the liquid oral composition can consist of chlorpromazine hydrochloride, sucralose, sodium benzoate, sodium citrate, citric acid, disodium edetate, water, optionally a flavoring agent, and optionally a coloring agent. In various embodiments, the liquid oral composition can be formulated to include a 30 mg/mL concentration or a 100 mg/mL concentration of chlorpromazine hydrochloride, as shown in Table 1 below.

TABLE 1

Exemplary formulations

| Ingredients | Strength | |
|---|---|---|
| | 30 mg/ml | 100 mg/ml |
| Chlorpromazine Hydrochloride | 30.000 | 100.000 |
| Sucralose, NF | 9.000 | 30.000 |
| Sodium Benzoate, NF | 0.300 | 1.000 |
| Sodium Citrate, Dihydrate, | 1.566 | 5.220 |
| Citric Acid Anhydrous, USP | 1.018 | 3.393 |
| Disodium Edetate, USP | 1.000 | 1.000 |
| Purified Water, USP | 968.116 | 898.387 |
| Total | 1011.000 | 1039.000 |

Certain non-limiting embodiments of the oral liquid composition according to the present disclosure can comprise a color in a range of clear/colorless to pale yellow, a pH in a range of about 2.0 to about 5.0, a total aerobic microbial count of no greater than about 100 cfu/g, a total combined yeast and mold count of no greater than about 10 cfu/g, and can lack *Escherichia coli* and *Burkholderia cepacia*.

Manufacture

A process of manufacturing embodiments of an oral liquid composition comprising chlorpromazine according to the present disclosure can comprise adding excipients including a solvent in predetermined weights or volumes to a mixing tank (e.g., a stainless steel mixing tank having a volume of about 75 gallons) to form a first solution. In various non-limiting embodiments, the mixing tank can comprise an overhead mixer, such as, for example, a lightning mixer. The first solution is mixed in the mixer until the first solution is clear and substantially free of particulate. The fill level in the mixing tank can affect mixing dynamics and thus the homogeneity of the first solution. The batch size for manufacturing the oral liquid composition can be defined according to the size of the mixing tank to ensure sufficient submersion of the impeller blades, vortex formation, and uniform mixing. However, under or overfilling the mixing tank may affect the homogeneity of the first solution. The batch size can be fixed to ensure that the batch volume does not affect the critical quality attributes (CQAs) of the final oral liquid composition.

Mixing methods encompass any type of mixing resulting in a homogenous oral liquid composition. Mixing can include one or more of stirring, shaking, swirling, agitating, or inverting. In various non-limiting embodiments, the solvent (e.g., water) can be added to the mixing tank prior to introducing the powdered excipients. In some non-limiting embodiments, individual ingredients of the oral liquid composition are added sequentially, concurrently, or in any combination thereof to a solvent. In some non-limiting embodiments, individual ingredients are added sequentially, i.e., one at a time. In certain non-limiting embodiments, the sequential addition of individual ingredients includes mixing for a certain time interval after each or some of the sequential additions. In various non-limiting embodiments, all individual ingredients are added at the same time to a solvent and then mixed for a certain time interval.

In some non-limiting embodiments, the oral liquid composition disclosed herein is homogenous. As used herein, a "homogenous" liquid refers to a liquid that is uniform in appearance, identity, consistency, and active pharmaceutical ingredient concentration per volume. Non-homogenous liquids include liquids that have varied coloring, and/or viscosity, as well as non-uniform active pharmaceutical ingredient concentration in each unit volume.

Homogeneity in liquids can be assessed by qualitative identification or appearance tests and/or quantitative high performance liquid chromatography (HPLC) testing or the like. Exemplary qualitative testing includes visual inspection of the resultant liquid for air bubbles and/or undissolved solids which may cause variable dosing. Analytical HPLC testing can also determine drug concentration uniformity by examining aliquots of certain volume sections (e.g., about 5 or about 10 mL from the top, middle and bottom of about a 150 mL bottle). The mixing methods and excipients disclosed herein may be selected to impart a homogenous quality to the oral liquid compositions according to the present disclosure.

Mixing for a minimum time may be necessary to ensure dissolution of solid ingredients into the liquid phase to achieve a uniform bulk liquid solution. Inadequate mixing time may result in the presence of undissolved particles. In various non-limiting embodiments, mixing occurs for certain time intervals, such as, for example, about 10 seconds to about 90 minutes, about 10 seconds to about 60 minutes, about 1 minute to about 60 minutes, about 5 minutes to about 60 minutes, about 10 minutes to about 45 minutes, about 10 minutes to about 40 minutes, about 15 minutes to about 40 minutes, about 16 minutes to about 34 minutes, or about 21 minutes to about 39 minutes. For example, in certain non-limiting embodiments when the finished composition will include about 30 mg/mL of chlorpromazine, the mixing time interval can be about 16 minutes to about 34 minutes, and when the finished composition will include about 100 mg/mL of chlorpromazine, the mixing time interval can be about 21 minutes to about 39 minutes. In non-limiting embodiments where there are two or more mixing steps, the time intervals for each mixing can be the same or different. In some non-limiting embodiments, the resulting oral liquid composition is allowed to stand for a set amount of time, for example, about 5 minutes, about 10 minutes, about 20 minutes, about 30 minutes, about 40 minutes, about 50 minutes, about 60 minutes, about 90 minutes, about 120 minutes, or more to allow any resulting air bubbles arising from mixing to dissipate.

Adequate mixing speed is necessary to ensure complete dissolution of ingredients to obtain a uniform bulk liquid solution. Mixing at speeds that are suboptimal may result in settling of ingredients, retention of undissolved particulates, and prolong the manufacturing process. High mixing speed can result in splashing of the liquid. Therefore, the mixing speed should be optimized for each step of the process. In various non-limiting embodiments utilizing a mixer, the stirrer can be rotated at a speed in a range of about 50 RPM to about 500 RPM, such as, for example, about 100 RPM to about 300 RPM, about 100 RPM to about 200 RPM, or about 135 RPM to about 195 RPM. Additionally, the angle of the stirrer in the mixing tank, the length of the stirrer shaft, and the type of stirrer propeller should be optimized to effectively mix the solution.

Chlorpromazine hydrochloride exhibits pH dependent solubility and is sensitive to oxidation. Therefore, in various non-limiting embodiments including chlorpromazine hydrochloride and a buffer system (e.g., sodium citrate and citric acid) and/or a chelating agent (e.g., EDTA), solubilizing the buffer system and the chelating agent in the solvent prior to the addition of chlorpromazine hydrochloride can inhibit or prevent potential oxidation or precipitation of the chlorpromazine hydrochloride or other excipients. Therefore, after the excipients are thoroughly mixed together, the API (e.g., chlorpromazine hydrochloride) can be added to the first solution to form a second solution. Thereafter, the second solution is mixed until the second solution is clear and substantially free of particulate. In some non-limiting embodiments, the second solution is substantially free of solids, whereby all components are fully solubilized. The phrase "substantially free of solids", as used herein refers the characteristic wherein a solution is essentially or fundamentally devoid of solid particulates.

The second solution can be filtered through a filter to form a filtered solution. Filtration can remove foreign particulate matter and enhance the appearance of the liquid oral composition. A filter with about 5 um pore size, for example, can be suitable to remove suspended particulate matter. The filter can be made of polypropylene, for example, which can be suitable for filtration of aqueous products.

Thereafter, the filtered solution can be disposed in a holding tank and held for a period of time until the filtered solution can be packaged in a container. Appearance of the liquid oral composition can be affected (e.g., appear discolored) during bulk hold in the holding tank due to oxidative degradation of, for example, chlorpromazine hydrochloride. Therefore, the holding tank can be purged with nitrogen to reduce oxygen levels in the holding tank and/or the filtered solution. The nitrogen purge can be initiated prior to filling the holding tank with the filtered solution. Initiating the purge can be at a nitrogen flow rate of about 50 SCFH and for a time of about 36 minutes, for example. Additionally, purging of the holding tank can be continued after filtration. For example, the post filtrate purge can be at a flow rate of about 50 SCFH for about 24 minutes. Additionally, excessive headspace in the holding tank can increase exposure to oxygen and thus, the holding tank can be properly sized to the volume of liquid oral composition to be produced so as to limit headspace.

The period of time that the filtered solution spends in the holding tank can impact the degradation of chlorpromazine hydrochloride. Although the holding tank can be sealed, the holding tank may not capable of being pressurized and the oxygen level in the tank may not be able to be controlled. Thus, the period of time that the filtered solution spends in the holding tank should be optimized for efficient processing and inhibition of degradation of the chlorpromazine hydrochloride.

From the holding tank, the filtered solution can be packed in individual bottles with nitrogen purging and followed by induction sealing. Each bottle can be purged prior to filling the bottle with the liquid oral chlorpromazine solution. For example, each bottle can be purged at a flow rate of about 60 SL/min for about 10 second prior to filling. Additionally, each bottle can be purged after filling the bottle with the filtered solution. For example, each bottle can be purged at a flow rate of about 22 SCFH (about 10 SL/min) for about 10 second post sealing. Thereafter, the bottles can be sealed, such as, for example, induction sealed. Use of induction sealing can prevent oxygen permeation during storage of the bottles.

The foregoing process can achieve a dissolved oxygen content of less than or equal to about 8 mg/L, for example, in the oral liquid oral composition packaged in the bottle. The extent of dissolved oxygen can have an impact on the oxidative stability of chlorpromazine hydrochloride. The dissolved oxygen can be dependent on the mixing speed, time in the manufacturing process, and environmental conditions during the manufacture of the liquid oral composition. If the level of dissolved oxygen is too high, the dissolved oxygen may lead to oxidation of the chlorpromazine hydrochloride and thus can result in product discoloration and higher impurity levels. In various non-limiting embodiments, the process of manufacturing may not require nitrogen sparging through the liquid oral composition in order to achieve a desired dissolved oxygen content. In various non-limiting embodiments, the process of manufacturing the liquid oral composition can be performed without heating.

In various non-limiting embodiments, the bottle used for packaging the liquid oral composition comprising chlorpromazine according to the present disclosure can inhibit oxygen permeation, contain minimal headspace, and protect the composition from light. Additionally, the bottle can enable ease of handling. The bottle can be capped with a child resistant closure and a heat induction seal liner. Induction sealing can minimize oxygen exposure of the packaged liquid oral composition during storage. In various embodiments, the drug product comprising the packaged liquid oral composition according to the present disclosure can be suitable for storage between about 15° C. and about 30° C. (about 59° F. to about 86° F.) and should be protected from light. In various non-limiting examples, the bottle used to package the oral liquid composition can be constructed from at least one of amber PET/PETE, clear PET/PETE, polyethylene (HDPE, LDPE), polyvinyl chloride (PVC), polypropylene (PP), polystyrene (PS), and glass.

In various examples, an oral liquid composition according to the present disclosure comprising a chlorpromazine (e.g., chlorpromazine hydrochloride) content of about 30 mg/mL can be packaged in a 4 oz. amber polyethylene terephthalate (PET) bottle with about a 24 mm/400 white child resistant cap (e.g., style "M") with a heat induction seal (HIS) liner. FIGS. 1A-1E illustrate a non-limiting embodiment of such a bottle and cap. In various embodiments, the bottle can comprise a fill volume of about 120 ml, a capacity to overflow of about 134 mL±5.0 mL, a weight of 16 grams±1 gram, and a minimum wall thickness of about 0.012 inch. In various non-limiting embodiments, as illustrated in FIG. 1A, the bottle can be a modern boston round bottle.

In various non-limiting examples, an oral liquid composition according to the present disclosure comprising a chlorpromazine (e.g., chlorpromazine hydrochloride) content of about 100 mg/mL can be packaged in an 8 oz. amber polyethylene terephthalate (PET) bottle with about a 24 mm/400 child resistant cap (e.g., Style "M"; Special "H") with a heat induction seal (HIS) liner. FIGS. 2A-2E illustrate a non-limiting embodiment of such a bottle and cap. In various non-limiting embodiments, the bottle can comprise a fill volume of about 240 ml, a capacity to overflow of about 263 mL±7.0 mL, a weight of 29.5 grams±1 gram, and a minimum wall thickness of about 0.020 inch. In various non-limiting embodiments, the bottle can be a modern boston round bottle.

Benefits

The liquid oral compositions according to the present disclosure can be formulated with a desired number and respective amounts of excipients such that the composition is stable. Including a minimum number and amount of excipients can minimize potential interaction between the excipients and the chlorpromazine (e.g., chlorpromazine hydrochloride), and consequently the extent of degradation, i.e., generation of impurity A. Additionally, maintaining the pH of the composition utilizing a buffer system to keep the formulation at a desired pH or within a desired pH range can inhibit degradation of chlorpromazine (e.g., chlorpromazine hydrochloride). Also, for example, adding EDTA can inhibit or prevent a color change induced by the complexation of, for example, chlorpromazine hydrochloride with trace amounts of metal ions present in the excipients as impurities. Further, purging the holding tank with nitrogen before and after the transfer of the bulk liquid formulation to prevent degradation of the solution during storage, prior to packaging, can also inhibit degradation of, for example, chlorpromazine hydrochloride.

In various non-limiting embodiments, packaging the liquid oral composition according to the present disclosure in PET bottles can minimize environmental oxygen permeation and consequently inhibit the generation of impurity A during storage. Minimizing headspace in the bottle in which an oral liquid composition according to the present disclosure is packaged can reduce exposure of the packaged product to oxygen and thus, inhibit oxidative degradation, i.e., generation of impurity A. Purging bottles with nitrogen before and after filling can in certain cases achieve a dissolved oxygen level less than about 8 mg/l which can inhibit oxidative degradation, i.e., generation of impurity A.

Combining formulation, processing, and packaging factors has allowed the inventors to produce compositions according to the present disclosure including about 30 mg/mL chlorpromazine in which impurity A levels do not exceed about 0.6% during a desired shelf life of the product, e.g., 24 months. Also, combining formulation, processing, and packaging factors has allowed the inventors to produce compositions according to the present disclosure including about 100 mg/mL chlorpromazine in which impurity A levels do not exceed about 0.2% during a desired shelf life of the product, e.g., 24 months.

Use of the Compositions

In another aspect according to the present disclosure, methods of treatment comprising administering an oral liquid composition according to the present disclosure comprising chlorpromazine to a subject in need thereof are provided. In certain non-limiting embodiments, an oral liquid composition according to the present disclosure can be used in the treatment of the following indications: manifestations of psychotic disorders; nausea and vomiting; restlessness and apprehension before surgery; acute intermittent porphyria; tetanus (e.g., as an adjunct); manifestations of the manic type of manic-depressive illness; intractable hiccups; severe behavioral problems in children (1 to 12 years of age) marked by combativeness and/or explosive hyperexcitable behavior (out of proportion to immediate provocations), and hyperactive children who show excessive motor activity with accompanying conduct disorder. A method for treating any of the diseases or conditions disclosed herein involves administration of therapeutically effective amounts of the oral liquid compositions herein to a subject in need thereof.

Dosages of the oral liquid compositions disclosed herein can be determined by any suitable method. Maximum tolerated dose (MTD) and maximum response dose (MRD) for chlorpromazine can be determined via established animal and human experimental protocols. For example, toxicity and therapeutic efficacy of chlorpromazine can be determined by standard pharmaceutical procedures in cell cultures or experimental animals, including, but not limited to, determination of the $LD_{50}$ (the dose lethal to about 50% of the population) and the $ED_{50}$ (the dose therapeutically effective in about 50% of the population). The dose ratio between the toxic and therapeutic effects is known as the therapeutic index, and it can be expressed as a ratio between $LD_{50}$ and $ED_{50}$. Chlorpromazine dosages exhibiting high therapeutic indices are desirable. The data obtained from cell culture assays and animal studies can be used in formulating a range of dosage for use in humans. The dosage of such compounds lies preferably within a range of circulating concentrations that include the $ED_{50}$ with minimal toxicity. The dosage may vary within this range depending upon the dosage form employed and the route of administration utilized. Additional relative dosages, represented as a percent of maximum response or of maximum tolerated dose, are readily obtained via these protocols.

In some non-limiting embodiments, an oral liquid composition according to the present disclosure is provided in a dosage that is similar, comparable, or equivalent to a dosage of a known chlorpromazine tablet formulation. In other non-limiting embodiments, the oral liquid composition is provided in a dosage that provides similar, comparable, or equivalent pharmacokinetic parameters (e.g., AUC, $C_{max}$, $T_{max}$, $C_{min}$, $T_{1/2}$) as a dosage of a commercially available chlorpromazine tablet formulation. Similar, comparable, or equivalent pharmacokinetic parameters, in some instances, refer to parameters within about 80% to about 125%, about 80% to about 120%, about 85% to about 125%, of about 90% to about 110% of given values.

As used herein, the term "AUC" refers to the integral of the concentration-time curve. The terms "$AUC_{last}$" and "$AUC_{0-t}$" as used herein refer to the area under a plasma concentration versus time curve from time 0 to the time of the last measured concentration of drug within the plasma. The terms "$AUC_{inf}$" and "$AUC_{0\rightarrow\infty}$" as used herein refer to the area under a plasma concentration versus time curve from time 0 to infinity.

As used herein, the pharmacokinetic parameter $C_{max}$ refers to the maximum (i.e., peak) serum concentration of a specific compound in the body of a subject after a pharmaceutical composition or compound has been administrated to the subject. The term "$C_{last}$" as used herein refers to the last observed quantifiable concentration of a specific compound in the body of a subject after a pharmaceutical composition or compound has been administrated to the subject.

As used herein, the pharmacokinetic parameter $T_{max}$ for a pharmaceutical composition or compound is the time after administration to a subject at which the $C_{max}$ is observed in the subject. As such, the term "$T_{max}$" as used herein refers to the time after administration of a drug when the maximum plasma concentration is reached.

As used herein, the term "absorptivity factor" refers to the maximum (i.e., peak) serum concentration of a specific compound in the body of a subject after a pharmaceutical composition or compound has been administrated to the subject ($C_{max}$) divided by the area under the drug concentration-time curve from time 0 to infinity ($AUC_{inf}$).

Oral liquid compositions described herein can be administered at a dosage disclosed herein or at other appropriate dose levels contemplated by a medical practitioner. In certain non-limiting embodiments, oral liquid compositions according to the present disclosure are administered for prophylactic and/or therapeutic treatments. In certain therapeutic applications, the oral liquid compositions are administered to a patient already suffering from an indication in a therapeutically effective amount sufficient to cure the disease or at least partially arrest or ameliorate the symptoms. Amounts effective for this use depend on, for example, the age of the patient, severity of the disease, previous therapy, the patient's health status, weight, and response to the oral liquid compositions, and are within the judgment of the treating physician. Therapeutically effective amounts are optionally determined by methods including, but not limited to, a dose escalation clinical trial.

In certain non-limiting embodiments wherein the patient's condition does not improve, upon the doctor's discretion, an oral liquid composition according to the present disclosure may be administered chronically, that is, for an extended period of time, including throughout the duration of the patient's life, to ameliorate or otherwise control or limit the symptoms of the patient's disease. In some non-limiting embodiments, administration of the oral liquid composition continues until complete or partial response of a disease occurs.

In some non-limiting embodiments, an oral liquid composition as disclosed herein is administered to a subject who is in a fasted state. A fasted state refers to the state of a subject who has gone without food or fasted for a specified amount of time. General fasting periods include at least 4 hours, at least 6 hours, at least 8 hours, at least 10 hours, at least 12 hours, at least 14 hours, and at least 16 hours without food. In certain non-limiting embodiments, an oral liquid composition herein is administered to a subject who has fasted overnight.

In some non-limiting embodiments, an oral liquid composition as disclosed herein is administered to a subject who is in a fed state. A fed state refers to the state of a subject who has taken food or has had a meal. In certain non-limiting embodiments, an oral liquid composition is administered to a subject in a fed state 5 minutes post-meal, 10 minutes post-meal, 15 minutes post-meal, 20 minutes post-meal, 30 minutes post-meal, 40 minutes post-meal, 50 minutes post-meal, 1 hour post-meal, 2 hours post-meal, or more. In certain non-limiting embodiments, an oral liquid composition is administered to a subject along with food.

In some non-limiting embodiments, the treatment of certain diseases or conditions in a subject with an oral liquid composition as disclosed herein encompasses additional therapies and treatment regimens with other active pharmaceutical ingredients. In some non-limiting embodiments, additional therapies and treatment regimens can include sequential or concurrent administration of a second active ingredient to a subject to treat the same or different disease or condition being treated with the oral liquid composition. In various non-limiting embodiments, additional therapies and treatment regimens include sequential or concurrent administration of a second active ingredient to a subject to treat adjunct conditions associated with the disease or condition or a side effect from the oral liquid composition in the therapy.

In some non-limiting embodiments, an oral liquid composition according to the present disclosure is diluted prior to administration to enhance characteristics such as, for example, palatability. Examples of possible vehicles for dilution include tomato or fruit juice, milk, simple syrup, orange syrup, carbonated beverages, coffee, tea, water, and semisolid foods (soups, puddings, etc.).

Example 1

Common excipients functioning as a solvent, a sweetener, an antioxidant, a chelating agent, a buffer system component, and a preservative were evaluated in the following example for excipient and drug substance compatibility. Compatibility was assessed through high performance liquid chromatography (HPLC) analysis of solutions containing the mixtures of the drug substance and the individual evaluated excipient in purified water. A relatively low concentration (20 mg/ml) of active pharmaceutical ingredient was selected to enhance potential oxidative or hydrolytic degradation of the API in the presence of the excipients. The excipients were used in slight excess to enhance potential interactions. The proportion of each excipient with respect to API is given in Table 2 below. The proportion of excipients was selected such that it was representative of their respective proportions to the API in the finished product. The solutions were filled in amber glass bottles and stored at 60° C. for 15 days or 25° C./60% RH and 40° C./75% RH for 1 month.

TABLE 2

Composition of Solutions for Drug-Excipient Compatibility Studies

| Mixture Components | API to Excipient Ratio (w/w) |
|---|---|
| Chlorpromazine Hydrochloride (API) | NA |
| API/Sucrose | 1:34 |
| API/Sodium Benzoate | 1:0.05 |
| API/Citric Acid Anhydrous | 1:0.17 |
| API/Sodium Citrate Dihydrate | 1:0.26 |
| API/Sodium Metabisulfite | 1:0.05 |
| API/FD&C Yellow #6 | 1:0.003 |
| API/Natural & Artificial Orange Flavor | 1:0.15 |
| API/Sucralose | 1:0.3 |
| API/Disodium Edetate (EDTA) | 1:0.05 |

Table 3 provides a summary of the composition of the API/excipient mixtures and assay values at time zero and after storage for 15 days at 60° C. or for 1 month at 25° C./60% RH and 40° C./75% RH. Tables 4 to 7 provide impurity profiles of samples at time zero and after storage for 15 days at 60° C. or for 1 month at 25° C./60% RH and 40° C./75% RH. In those tables, the impurities are as follows: chlorpromazine sulfoxide (Impurity A); 2-chloro-10{[N-methyl-N-(3-dimethylaminopropyl)]-3-aminopropyl}phenothiazine (Impurity B); phenothiazine (Impurity C); N-dimethyl chlorpromazine (Impurity D); 2-chlorophenothiazine (Impurity E). Compatibility studies with sodium citrate could not be conducted since the drug precipitated in the highly basic environment created by sodium citrate alone. Such precipitation is not expected in the presence of other excipients within the product (e.g., buffering system including both citric acid and sodium citrate). Additionally, the pH of the solution was also monitored during development to ensure the physical stability of the product.

TABLE 3

Summary of assay of chlorpromazine hydrochloride at time zero and after storage at 60° C. for 15 days, and at 25° C./60% RH or 40° C./75% RH for 1 month ("M").

| | Assay of Chlorpromazine Hydrochloride (% Label Claim) | | | |
|---|---|---|---|---|
| Sample Description | $T_0$ | 15 Days, 60° C. | 1 M, 25° C./ 60% RH | 1 M, 40° C./ 75% RH |
| Chlorpromazine Hydrochloride (API) | 98.3 | 100.9 | 98.6 | 98.7 |
| API/Sucrose | 98.7 | 101.1 | 97.6 | 97.8 |
| API/Sodium Benzoate | 98.2 | 100.8 | 98.3 | 99.1 |
| API/Citric Acid Anhydrous | 98.4 | 98.9 | 98.9 | 98.6 |
| API/Sodium Metabisulfite | 97.7 | 102.5 | 97.9 | 96.2 |
| API/FD&C Yellow #6 | 99.0 | 102.9 | 98.3 | 96.8 |
| API/Natural & Artificial Orange Flavor | 99.1 | 102.2 | 98.4 | 98.3 |
| API/Sucralose | 98.2 | 97.5 | 98.9 | 98.6 |
| API/Disodium Edetate (EDTA) | 99.1 | 98.8 | 98.4 | 98.1 |

TABLE 4

Summary of impurities for Chlorpromazine Hydrochloride at time zero

| | Impurities (%) | | | | | | | | | | | | |
|---|---|---|---|---|---|---|---|---|---|---|---|---|---|
| Sample Description | A | B | C | D | E | Brompromazine | UD (RRT 0.49) | UD (RRT 0.55) | UD (RRT 0.61) | UD (RRT 0.82) | UD (RRT 1.31) | UD (RRT 1.42) | Total |
| API + Water | ND | ND | ND | ND | ND | ND | NA | NA | NA | 0.08 | 0.03 | ND | 0.11 |
| API/Sucrose | ND | ND | ND | ND | ND | ND | NA | NA | NA | 0.09 | 0.03 | ND | 0.12 |
| API/Sodium Benzoate | ND | ND | ND | ND | ND | ND | NA | NA | NA | 0.08 | 0.03 | ND | 0.11 |
| API/Citric Acid Anhydrous | ND | ND | ND | ND | ND | ND | NA | NA | NA | 0.08 | 0.03 | ND | 0.11 |
| API/Sodium Metabisulfite | 0.20 | ND | ND | ND | ND | ND | NA | NA | NA | 0.08 | 0.03 | ND | 0.30 |
| API/FD&C Yellow #6 | ND | ND | ND | ND | ND | ND | NA | NA | NA | 0.08 | 0.03 | ND | 0.11 |
| API/Natural & Artificial Orange Flavor | ND | ND | ND | ND | ND | ND | NA | NA | NA | 0.08 | ND | ND | 0.08 |
| API/Sucralose | ≤0.05 | NA | NA | NA | NA | NA | NA | NA | NA | NA | NA | NA | ≤0.05 |
| API/Disodium Edetate (EDTA) | ≤0.05 | NA | NA | NA | NA | NA | NA | NA | NA | NA | NA | NA | ≤0.05 |

ND—Not Detected;

NA—Not Available;

UD—Undefined;

RRT—Relative Retention Time

TABLE 5

Summary of impurities for Chlorpromazine Hydrochloride after storage for 15 days at 60° C.

| | Impurities (%) | | | | | | | | | | | | |
|---|---|---|---|---|---|---|---|---|---|---|---|---|---|
| Sample Description | A | B | C | D | E | Brompromazine | UD (RRT 0.49) | UD (RRT 0.55) | UD (RRT 0.61) | UD (RRT 0.82) | UD (RRT 1.31) | UD (RRT 1.42) | Total |
| API + Water | 0.55 | ND | 0.08 | 0.18 | 0.02 | ND | 0.02 | 0.14 | 0.03 | NA | NA | 0.03 | 1.04 |
| API/Sucrose | 0.63 | ND | 0.09 | 0.03 | ND | ND | 0.02 | 0.11 | 0.02 | NA | NA | 0.03 | 0.93 |
| API/Sodium Benzoate | 0.64 | ND | 0.08 | 0.52 | 0.09 | ND | ND | 0.10 | 0.02 | NA | NA | 0.03 | 1.48 |
| API/Citric Acid Anhydrous | 0.59 | ND | 0.08 | 0.02 | 0.03 | ND | 0.02 | 0.10 | 0.02 | NA | NA | 0.03 | 0.89 |
| API/Sodium Metabisulfite | 0.60 | ND | 0.08 | 0.02 | ND | ND | 0.02 | 0.16 | 0.02 | NA | NA | 0.03 | 0.95 |
| API/FD&C Yellow #6 | 0.62 | ND | 0.08 | 0.21 | 0.03 | ND | 0.02 | 0.08 | 0.03 | NA | NA | 0.03 | 1.10 |
| API/Natural & Artificial Orange Flavor | 0.60 | ND | 0.08 | 0.07 | ND | ND | 0.02 | 0.17 | 0.03 | NA | NA | 0.03 | 1.00 |
| API/Sucralose | 0.68 | NA | NA | NA | NA | NA | NA | NA | NA | NA | NA | NA | 0.68 |
| API/Disodium Edetate (EDTA) | 0.77 | NA | NA | NA | NA | NA | NA | NA | NA | NA | NA | NA | 0.77 |

ND—Not Detected;
NA—Not Available;
UD—Undefined;
RRT—Relative Retention Time

TABLE 6

Summary of impurities for Chlorpromazine Hydrochloride after storage for 1 Month at 25° C./60% RH

| | Impurities (%) | | | | | | | | | | | | |
|---|---|---|---|---|---|---|---|---|---|---|---|---|---|
| Sample Description | A | B | C | D | E | Brompromazine | UD (RRT 0.49) | UD (RRT 0.55) | UD (RRT 0.61) | UD (RRT 0.82) | UD (RRT 1.31) | UD (RRT 1.42) | Total |
| API + Water | 0.07 | ND | 0.07 | 0.03 | ND | ND | NA | 0.02 | 0.02 | NA | NA | 0.03 | 0.24 |
| API/Sucrose | 0.10 | ND | 0.07 | 0.02 | ND | ND | NA | 0.02 | 0.02 | NA | NA | 0.03 | 0.27 |
| API/Sodium Benzoate | 0.48 | 0.03 | 0.07 | 0.04 | ND | ND | NA | 0.02 | NA | NA | NA | 0.03 | 0.67 |
| API/Citric Acid Anhydrous | 0.07 | 0.03 | 0.07 | 0.02 | ND | ND | NA | 0.02 | NA | NA | NA | 0.03 | 0.25 |
| API/Sodium Metabisulfite | 0.75 | 0.03 | 0.07 | 0.02 | ND | ND | NA | 0.02 | NA | NA | NA | 0.03 | 0.92 |
| API/FD&C Yellow #6 | 0.07 | 0.03 | 0.07 | 0.03 | ND | ND | NA | 0.02 | NA | NA | NA | 0.03 | 0.25 |
| API/Natural & Artificial Orange Flavor | 0.11 | 0.03 | 0.07 | 0.02 | ND | ND | NA | 0.02 | NA | NA | NA | 0.03 | 0.29 |
| API/Sucralose | <0.05 | NA | NA | NA | NA | NA | NA | NA | NA | NA | NA | NA | <0.05 |
| API/Disodium Edetate (EDTA) | 0.15 | NA | NA | NA | NA | NA | NA | NA | NA | NA | NA | NA | 0.15 |

ND—Not Detected;
NA—Not Available;
UD—Undefined;
RRT—Relative Retention Time

TABLE 7

Summary of impurities for Chlorpromazine Hydrochloride after storage for 1 Month at 40° C./75% RH

| | Impurities (%) | | | | | | | | | | | | |
|---|---|---|---|---|---|---|---|---|---|---|---|---|---|
| Sample Description | A | B | C | D | E | Brompromazine | UD (RRT 0.39) | UD (RRT 0.55) | UD (RRT 0.61) | UD (RRT 0.82) | UD (RRT 1.31) | UD (RRT 1.42) | Total |
| API + Water | 0.21 | ND | 0.07 | 0.08 | ND | ND | NA | 0.02 | 0.02 | NA | NA | 0.03 | 0.44 |
| API/Sucrose | 0.32 | ND | 0.07 | 0.03 | ND | ND | NA | 0.02 | 0.02 | NA | NA | 0.03 | 0.49 |
| API/Sodium Benzoate | 0.63 | 0.03 | 0.07 | 0.11 | 0.02 | ND | NA | 0.02 | NA | NA | NA | 0.03 | 0.91 |
| API/Citric Acid Anhydrous | 0.21 | 0.03 | 0.07 | 0.02 | ND | ND | NA | 0.02 | NA | NA | NA | 0.03 | 0.38 |
| API/Sodium Metabisulfite | 0.83 | 0.03 | 0.07 | 0.02 | ND | ND | NA | 0.02 | NA | NA | NA | 0.03 | 1.01 |
| API/FD&C Yellow #6 | 0.21 | 0.03 | 0.07 | 0.06 | ND | ND | NA | 0.02 | NA | NA | NA | 0.03 | 0.42 |
| API/Natural & Artificial Orange Flavor | 0.23 | 0.03 | 0.07 | 0.04 | ND | ND | NA | 0.02 | NA | NA | NA | 0.03 | 0.42 |

TABLE 7-continued

Summary of impurities for Chlorpromazine Hydrochloride after storage for 1 Month at 40° C./75% RH

| | Impurities (%) | | | | | | | | | | | | |
|---|---|---|---|---|---|---|---|---|---|---|---|---|---|
| Sample Description | A | B | C | D | E | Brompro-mazine | UD (RRT 0.39) | UD (RRT 0.55) | UD (RRT 0.61) | UD (RRT 0.82) | UD (RRT 1.31) | UD (RRT 1.42) | Total |
| API/Sucralose | <0.05 | NA | NA | NA | NA | NA | NA | NA | NA | NA | NA | NA | <0.05 |
| API/Disodium Edetate (EDTA) | 0.46 | NA | NA | NA | NA | NA | NA | NA | NA | NA | NA | NA | 0.46 |

ND—Not Detected;
NA—Not Available;
UD—Undefined;
RRT—Relative Retention Time

The assay results for chlorpromazine hydrochloride showed a negligible decrease from time zero at all the tested conditions indicating that all the tested excipients are compatible with the drug substance. The impurity levels at time zero were minimal, however, a considerable increase in the level of Impurity A (chlorpromazine sulfoxide) was seen upon storage at controlled room temperature and humidity as well as at the accelerated stability conditions. The level of Impurity A in the bottle containing only the drug substance dissolved in water, i.e., without any other excipient, after 15 days at 60° C. was nearly equivalent to its level in containers with the excipients. This demonstrated that presence of excipients did not accelerate degradation and the drug substance was inherently susceptible to some degradation. However, a considerable difference in the impurity A levels was seen in the samples with and without excipients that had been stored at 25° C./60% RH and 40° C./75% RH. The impurity A levels were found to be comparatively high for samples containing sodium benzoate and sodium metabisulfite. It was surprising to see an increase in the level of impurity A in the presence of sodium metabisulfite since impurity A (chlorpromazine sulfoxide) is a result of oxidative degradation, and sodium metabisulfite is a widely used as an antioxidant, including in injectable formulations of chlorpromazine hydrochloride currently on the market (LARGACTIL®). Similarly, sodium benzoate was present in the reference listed drug formulation of THORAZINE®. Although potential interaction was seen with sodium benzoate and sodium metabisulfite, the extent of degradation was limited. Therefore, the impurity was closely monitored through the development process. Subsequent assurance of compatibility was provided by long-term stability data for product development batches and process performance qualification (PPQ)/stability batches. Other impurities were also detected but found to be in negligible concentrations that did not seem to significantly increase upon storage under the room temperature or accelerated storage conditions.

Example 2

The following examples were performed to prepare product development (PD) batches of compositions according to the present disclosure including about 100 mg/ml of chlorpromazine hydrochloride. Formulations of commercial product with proposed strengths of 30 mg/ml and 100 mg/ml chlorpromazine hydrochloride were intended to be dose proportional. Therefore, product development studies were initiated with the higher strength, i.e., 100 mg/ml, as that would represent the more difficult scenario with respect to drug, excipient solubility and the manufacturing process.

Batches NB538-031 and NB538-034 having the formulations shown in Table 8 below were prepared. Sodium metabisulfite and ascorbic acid were tested as antioxidant in batches NB538-031 and NB538-034, respectively. Additionally, sodium citrate was excluded from the formulation for batch NB538-034 to evaluate if lowering pH in presence of ascorbic acid would lead to an improvement in the stability.

TABLE 8

Formulation Composition
Formulation Composition
Respective Ingredient Concentration in mg/mL; Batch Size: 200 mL

| Ingredients | Lot # NB538-0311 (100 mg/mL) | Lot # NB538-034 (100 mg/mL) |
|---|---|---|
| Chlorpromazine Hydrochloride | 100.000 | 100.000 |
| Sucralose, USP | 1.500 | 1.500 |
| Sodium Benzoate, NF | 1.000 | 1.000 |
| Sodium Citrate, Dihydrate, USP | 5.220 | |
| Citric Acid Anhydrous, USP | 3.393 | 3.393 |
| Citrus Flavor | 3.000 | 3.000 |
| EDTA (ethylenedinitrilotetraacetic acid disodium salt dihydrate | 0.420 | 0.420 |
| Sodium Metabisulfite | 5.000 | |
| Ascorbic Acid | | 0.500 |
| Purified Water, USP | Q.S. to 1 mL | Q.S. to 1 mL |

To prepare NB538-031 and NB538-034, sucralose was dissolved in purified water using an overhead stirrer. Citric acid and sodium citrate (NB538-031 only) were added to this solution and mixed until a clear solution was obtained. Sodium benzoate, EDTA, sodium metabisulfite (NB538-031 only), and ascorbic acid (NB538-034 only) were then added to this solution and mixed until a clear solution was obtained. Chlorpromazine hydrochloride was then added and mixed until a clear solution was obtained. Citrus flavor, which is available in liquid form, was added and mixed for 5 minutes to allow uniform mixing of the flavor in the solution. The solution was then transferred to a volumetric flask and purified water was added q.s. to 200 mL. The resulting batches were then packaged in various manners, stored under selected storage conditions, and monitored over time to determine the stability of chlorpromazine hydrochloride in the solutions. The packaging details, storage conditions, and results are shown in Table 9 below

TABLE 9

Observations

| Sampling Time Point | Condition | Bottle Type | pH | Appearance | Assay (%) | Impurities (%) | | | |
|---|---|---|---|---|---|---|---|---|---|
| | | | | | | A | C | UD | Total |
| Batch Type/Size Batch # NB538-031 (100 mg/mL) | | | | | | | | | |
| 0 Hour | NA | Glass | 3.6 | Light Yellow, Clear | 96.9 | 0.11 | 0.07 | ND | 0.18 |
| 7 Days | 60° C. | Glass | NA | NA | 98.6 | 0.14 | 0.07 | ND | 0.21 |
| 15 Days | 60° C. | Glass | NA | NA | 96.4 | 0.12 | 0.07 | ND | 0.19 |
| 1 Month | 25° C./60% RH | Glass | 3.2 | Light Yellow, Clear | 97.3 | 0.10 | 0.07 | ND | 0.17 |
| 1 Month | 40° C./75% RH | Glass | 3.1 | Light Yellow, Clear | 96.8 | 0.10 | 0.07 | ND | 0.17 |
| Batch Type/Size Batch # NB538-034 (100 mg/mL) | | | | | | | | | |
| 0 Hour | NA | Glass | 2.6 | Light Yellow, Clear | 97.0 | ND | 0.07 | ND | 0.07 |
| 7 Days | 60° C. | Glass | 2.6 | Yellow, Clear | 98.1 | 0.09 | 0.07 | ND | 0.16 |
| 15 Days | 60° C. | Glass | 2.5 | Yellow, Clear | 97.4 | 0.92 | 0.07 | ND | 0.99 |
| 1 Month | 25° C./60% RH | Glass | NA | NA | 98.5 | 0.09 | 0.07 | 0.03 | 0.19 |
| 1 Month | 40° C./75% RH | Glass | NA | NA | 98.1 | ND | 0.07 | ND | 0.07 |
| Packaging Bottle headspace purged with nitrogen prior to induction sealing | | | | | | | | | |
| Acceptance Criteria Target) | | pH | ≤5.0 | | | | | | |
| | | Assay | 90.0%-110.0% | | | | | | |
| | | Impurities | Impurity A: NMT 5.0%, Any Unidetuified Impurity: NMT 0.10%; Total Impurities: NMT 7.0% | | | | | | |

UD—Unidentified,
ND—Not Detected,
NMT—Not More Than,
NA—Not Available

The active and inactive ingredients dissolved rapidly. Therefore, modifications to the manufacturing process were not deemed necessary. The assay values met the intended specification and did not decrease upon storage under accelerated stability conditions. Although impurity A (chlorpromazine sulfoxide) was found to be under the specification limit at time zero and after storage under accelerated stability conditions, it was still relatively high in spite of the presence of EDTA, sodium metabisulfite, or ascorbic acid. The preliminary target was to control the level of impurity A at the ICH limits for individual impurities, i.e., at 0.20%. Since impurity C, phenothiazine, was a process impurity and it did not increase during storage it was not evaluated further.

Example 3

In order to improve stability and ease handling, packaging in non-glass containers, e.g., HDPE containers, was considered. A study was performed to evaluate the impact of individual excipients on the stability of a composition according to the present disclosure comprising 100 mg/ml chlorpromazine hydrochloride. Since addition of antioxidants and packaging in glass containers in presence of nitrogen did not result in acceptable impurity levels, the study was designed to determine the impact of individual excipients on the stability of the product packaged in HDPE bottles. Table 10 provides the formulations for several tested compositions. Batch number NB538-035 was prepared with EDTA and sodium metabisulfite. Batch NB538-037 was prepared without antioxidant or a chelating agent. Batch NB538-038 was prepared with sodium metabisulfite as an antioxidant. Batch NB538-039 was prepared with EDTA. Batch NB538-040 was prepared without an antioxidant, chelating agent, or flavor.

TABLE 10

Test compositions
Formulation Composition (Strength: 100 mg/mL)
Quantity in mg/mL (Batch Size: 200 mL)

| | NB538-(Batch no mentioned below) | | | | |
|---|---|---|---|---|---|
| Ingredients | 35 | 37 | 38 | 39 | 40 |
| Chlorpromazine Hydrochloride | 100.000 | 100.000 | 100.000 | 100.000 | 100.000 |
| Sucralose, USP | 1.500 | 1.500 | 1.500 | 1.500 | 1.500 |
| Sodium Benzoate, NF | 1.000 | 1.000 | 1.000 | 1.000 | 1.000 |
| Sodium Citrate, Dihydrate, USP | 5.220 | 5.220 | 5.220 | 5.220 | 5.220 |
| Citric Acid Anhydrous, USP | 3.393 | 3.393 | 3.393 | 3.393 | 3.393 |
| Citrus Flavor | 3.000 | 3.000 | 3.000 | 3.000 | |
| Sodium Metabisulfite | 0.395 | | 0.395 | | |
| EDTA | 0.420 | | | 0.420 | |
| Purified Water, USP | q.s to 1 mL | | | | |

To prepare batches NB538-035, NB538-037, NB538-038, NB538-039, and NB538-040, sucralose was dissolved in purified water using an overhead stirrer. Citric acid and sodium citrate were added to this solution and mixed till a clear solution was obtained. Sodium benzoate, EDTA (if applicable), and sodium metabisulfite (if applicable) were then added to this solution and mixed until a clear solution was obtained. Chlorpromazine hydrochloride was added and mixed until a clear solution was obtained. Citrus flavor (if applicable), which is available in liquid form, was added and mixed for 5 minutes to allow uniform mixing of the flavor in the solution. The solution was then transferred to a volumetric flask and purified water was added q.s. to 200 mL. Portions of the resulting batches were packaged in various manners, stored under selected storage conditions, and monitored over time to determine the stability of chlorpromazine hydrochloride in the solutions. The packaging details, storage conditions, and results are shown in Tables 11-15 below.

TABLE 11

Observations for NB538-035
Batch Type/Size Batch # NB538-035(100 mg/mL)

| Sampling Time Point | Storage Condition | Bottle Type | pH | Appearance | Assay (%) | Impurities (%)* A | C | UD | Total |
|---|---|---|---|---|---|---|---|---|---|
| Packaging Size (120 cc); Bottle headspace was not purged with nitrogen or induction sealed ||||||||||
| 0 Hour | NA | HDPE | 3.8 | Light Yellow, Clear | 98.1 | 0.49 | 0.07 | ND | 0.56 |
| 7 Days | 60° C. | HDPE | 3.8 | Light Yellow, Clear | 96.5 | 0.73 | 0.07 | ND | 0.80 |
| 32 Days | 60° C. | HDPE | NA | Light Yellow, Clear | NA | 1.00 | 0.07 | 0.07 | 122 |
| 1 Month | 25° C./60% RH | HDPE | NA | NA | NA | 0.57 | 0.07 | 0.07 | 0.74 |
| 1 Month | 40° C./75% RH | HDPE | NA | NA | NA | 0.70 | 0.07 | 0.07 | 0.87 |
| Packaging Size (120 cc); Bottle headspace was not purged with nitrogen or induction sealed ||||||||||
| 0 Hour | NA | HDPE | 3.7 | Light Yellow, Clear | 98.3 | 0.38 | 0.07 | ND | 0.45 |
| 7 Days | 60° C. | HDPE | 3.8 | Light Yellow, Clear | 97.6 | 0.52 | 0.07 | ND | 0.59 |
| 1 Month | 25° C./60% RH | HDPE | NA | NA | NA | 0.40 | 0.07 | 0.07 | 0.57 |
| 1 Month | 40° C./75% RH | HDPE | NA | NA | NA | 0.50 | 0.117 | 0.117 | 0.67 |
| Acceptance Criteria (Preliminary Target) | | pH Assay Impurities | ≤5.0% 90.0%-110.0% Impurity A NMT 5.0%, Any Unidentified Impurity: NMT 0.10%; Total Impurities: NMT 7.0% |||||||

UD—Unidentified,
ND—Not Detected,
NMT—Not More Than;
NA—Not Available
*Other process or UD impurities were also detected at insignificant levels. They have not been reported in the table.

TABLE 12

Observations for NB538-037
Batch Type/Size Batch # NB538-037 (100 mg/mL)

| Sampling Time Point | Storage Condition | Bottle Type | pH | Appearance | Assay (%) | Impurities (%) A | C | UD | Total |
|---|---|---|---|---|---|---|---|---|---|
| Packaging Bottle Capacity: 120 cc; Bottle headspace was not purged with nitrogen or induction sealed ||||||||||
| 0 Hour | NA | HDPE | 3.9 | Light Yellow, Clear | 96.9 | ND | 0.07 | ND | 0.07 |
| 7 Days | 60° C. | HDPE | 3.9 | Light Yellow, Clear | 98.3 | 0.06 | 0.08 | <0.05 | 0.14 |
| 15 Days | 60° C. | HDPE | 3.9 | Light Yellow, Clear | 101.1 | 0.23 | 0.07 | ND | 0.39 |
| 1 Month | 25° C./60% RH | HDPE | 3.9 | Light Yellow, Clear | 99.2 | 0.04 | 0.07 | 0.07 | 0.21 |
| 1 Month | 40° C./75% RH | HDPE | 3.9 | Light Yellow, Clear | 99.8 | 0.09 | 0.07 | 0.07 | 0.27 |
| Packaging Bottle Capacity: 120 cc; Bottle headspace was purged with nitrogen and induction sealed ||||||||||
| 0 Hour | NA | HDPE | 3.9 | Light Yellow, Clear | 98.0 | ND | 0.07 | ND | 0.07 |
| 7 Days | 60° C. | HDPE | 3.7 | Light Yellow, Clear | 98.3 | 0.13 | 0.07 | <0.05 | 0.20 |
| 15 Days | 60° C. | HDPE | 3.9 | Light Yellow, Clear | 100.6 | 0.13 | 0.07 | ND | 0.26 |
| 1 Month | 25° C./60% RH | HDPE | 3.9 | Light Yellow, Clear | 99.9 | 0.03 | 0.07 | 0.07 | 0.21 |
| 1 Month | 40° C./75% RH | HDPE | 3.9 | Light Yellow, Clear | 99.8 | 0.06 | 0.07 | 0.07 | 0.24 |
| Packaging Bottles were not purged with nitrogen nor induction sealed ||||||||||
| Acceptance Criteria (Preliminary Target) | | pH Assay Impurities | ≤5.0% 90.0%-110.0% Impurity A NMT 5.0%, Any Unidentified Impurity: NMT 0.10%; Total Impurities: NMT 7.0% |||||||

UD—Unidentified,
ND—Not Detected,
NMT—Not More Than,
NA—Not Available
*Other process or UD impurities were also detected at insignificant levels. They have not been reported in the table.

TABLE 13

Observations for NB538-038
Batch Type/Size Batch # NB538-038 (100 mg/mL)

| Sampling Time Point | Storage Condition | Bottle Type | pH | Appearance | Assay (%) | Impurities (%) A | C | UD | Total |
|---|---|---|---|---|---|---|---|---|---|
| Packaging Bottle Capacity: 120 cc; Bottles were purged with nitrogen but not sealed | | | | | | | | | |
| 0 Hour | NA | HDPE | 3.6 | NA | 97.1 | 0.43 | 0.07 | <0.05 | 0.51 |
| 7 Days | 60° C. | HDPE | 3.7 | Light Yellow, Clear | 97.2 | 0.52 | 0.07 | ND | 0.63 |
| Packaging Bottle Capacity: 120 cc; Bottles were not purged with nitrogen or sealed | | | | | | | | | |
| 0 Hour | NA | HDPE | 3.8 | NA | 95.3 | 0.44 | 0.07 | <0.05 | 0.51 |
| 7 Days | 60° C. | HDPE | 3.7 | Light Yellow, Clear | 96.3 | 0.62 | 0.07 | ND | 0.73 |
| Acceptance Criteria (Preliminary Target) | | pH Assay Impurities | | ≤5.0 90.0%-110.0% Impurity A NMT 5.0%, Any Unidentified Impurity: NMT 0.10%; Total Impurities: NMT 7.0% | | | | | |

UD—Unidentified,
ND—Not Detected,
NMT—Not More Than,
NA—Not Available

TABLE 14

Observations for NB538-039
Batch Type/Size Batch # NB538-039 (100 mg/mL)

| Sampling Time Point | Condition | Bottle Type | pH | Appearance | Assay (%) | Impurities (%) A | C | UD | Total |
|---|---|---|---|---|---|---|---|---|---|
| Packaging Bottle Capacity: 120 cc; Bottles were purged with nitrogen but not sealed | | | | | | | | | |
| 0 Hour | NA | HDPE | 3.8 | NA | 98.5 | <0.05 | 0.07 | <0.05 | 0.07 |
| 10 Days | 60° C. | HDPE | 3.9 | Light Yellow, Clear | 97.3 | 0.20 | 0.07 | ND | 0.31 |
| Packaging Bottle Capacity: 120 cc; Bottles were not purged with nitrogen or sealed | | | | | | | | | |
| 0 Hour | NA | HDPE | 3.7 | NA | 97.3 | <0.05 | 0.07 | <0.05 | 0.07 |
| 10 Days | 60° C. | HDPE | 3.8 | Light Yellow, Clear | 97.3 | 0.22 | 0.07 | ND | 0.33 |
| Reference ARD-18-504; ARD-18-579; ARD-18-505 ARD-118-580 | | | | | | | | | |
| Acceptance Criteria (Preliminary Target) | | pH Assay Impurities | | ≤5.0 90%-110.0% Impurity A NMT 5.0%, Any Unidentified Impurity: NMT 0.10%; Total Impurities: NMT 7.0% | | | | | |

UD—Unidentified,
ND—Not Detected,
NMT—Not More Than,
NA—Not Available

TABLE 15

Observations for NB538-040
Batch Type/Size Batch # NB538-040 (100 mg/mL)

| Sampling Time Point | Condition | Bottle Type | pH | Appearance | Assay (%) | Impurities (%) A | C | UD | Total |
|---|---|---|---|---|---|---|---|---|---|
| Packaging Bottle Capacity: 120 cc; Bottles were not purged with nitrogen nor sealed | | | | | | | | | |
| 0 Hour | NA | HDPE | 3.8 | Light yellow, clear | 95.8 | ND | 0.07 | ND | 0.07 |
| 19 Days | 60° C. | HDPE | NA | NA | NA | 0.27 | 0.07 | 0.07 | 0.51 |
| 1 Month | 40° C./75% RH | HDPE | NA | NA | 100.8 | 0.090 | 0.071 | ND | 0.16 |
| 1 Month | 25° C./60% RH | | NA | NA | 99.3 | ND | 0.070 | ND | 0.07 |
| Acceptance Criteria (Preliminary Target) | | pH Assay Impurities | | ≤5.0 90.0%-110.0% Impurity A: NMT 5.0%, Any Unidentified Impurity: NMT 0.10%; Total Impurities: NMT 7.0% | | | | | |

TABLE 15-continued

Observations for NB538-040
Batch Type/Size Batch # NB538-040 (100 mg/mL)

| Sampling | | Bottle | | | | | Impurities (%) | | |
|---|---|---|---|---|---|---|---|---|---|
| Time Point | Condition | Type | pH | Appearance | Assay (%) | A | C | UD | Total |

UD—Unidentified,
ND—Not Detected,
NMT—Not More Than,
NA—Not Available

Among the tested formulations, the level of impurity A was the highest for batch NB538-035 which contained EDTA as well as sodium metabisulfite. For batch NB538-037, the bottles purged with nitrogen were not sealed since corresponding caps were not available for induction sealing. In spite of being unsealed, the bottles purged with nitrogen showed lower levels of impurity A in comparison to those without nitrogen purging. However, such a trend was not observed for batches NB538-038 and NB538-039 as the difference between the levels of impurity A was minimal between bottles that were or were not purged with nitrogen.

Presence of impurity A at time zero in batches NB538-035 and NB538-038 indicated that sodium metabisulfite, rather than preventing oxidation, was responsible for generation of the oxidative degradant, impurity A, as impurity A was not detected at correspondingly high levels in batches NB538-037, NB538-039, and NB538-040. Given that the formulation without sodium metabisulfite and EDTA (NB538-037) exhibited the lowest level of impurity A among the tested formulations, EDTA, and sodium metabisulfite were excluded from future experiments. Ascorbic acid was evaluated an as an alternative antioxidant in the following experiment. Since impurity C (phenothiazine) was a process impurity and it did not increase during storage, it was not evaluated in further.

Example 4

To evaluate the impact of the presence of ascorbic acid and pH of the formulation on the stability of an oral liquid composition according to the present disclosure including 100 mg/ml chlorpromazine hydrochloride, the following study was performed. Although, it was tested in an earlier experiment (Batch NB538-034), it was of interest to see if it shows enhanced effectiveness at lower pH since its known to exhibit pH dependent antioxidant activity.

The composition for batch NB538-043 was kept identical to batch NB538-038, except that sodium metabisulfite was replaced by ascorbic acid. In order to decrease the pH of the formulation, batch NB538-044 was prepared without sodium citrate. FD&C Yellow #6 was included in batches NB538-045 and NB538-046, which were otherwise, identical to batches NB538-043 and NB538-044, respectively. The products were evaluated by packaging in HDPE as well as in glass bottles. The compositions for batches NB538-043, NB538-044, NB538-045, and NB538-046 are shown in Table 16 below.

TABLE 16

Formulation Compositions
Formulation Composition (Strength: 100 mg/mL)
Quantity in mg/mL (Batch Size: 200 mL)

| | NB538-Batch no. below | | | |
|---|---|---|---|---|
| Ingredients | 43 | 44 | 45 | 46 |
| Chlorpromazine Hydrochloride | 100.000 | 100.000 | 100.000 | 100.000 |
| Sucralose, USP | 1.500 | 1.500 | 1.500 | 1.500 |
| Sodium Benzoate, NF | 1.000 | 1.000 | 1.000 | 1.000 |
| Sodium Citrate, Dihydrate, USP | 5.220 | | 5.220 | |
| Citric Acid Anhydrous, USP | 3.393 | 3.393 | 3.393 | 3.393 |
| Ascorbic Acid | 0.500 | 0.500 | 0.500 | 0.500 |
| FD&C Yellow #6 | | | 0.062 | 0.062 |
| Purified Water, USP | q.s to 1 mL | | | |

To prepare batches NB538-043, NB538-044, NB538-045, and NB538-046, sucralose was dissolved in purified water using an overhead stirrer. Citric acid and sodium citrate (if applicable) were added to this solution and mixed until a clear solution was obtained. Sodium benzoate and ascorbic acid were then added to this solution and mixed until a clear solution was obtained. Chlorpromazine hydrochloride was added and mixed until a clear solution was obtained. FD&C Yellow #6 (if applicable) was added and mixed until it completely dissolved. The solution was then transferred to a volumetric flask and purified water was added q.s. to 200 mL. The resulting batches were then stored under certain conditions and monitored over time to determine the stability of the solutions. Table 17 provides the packaging details, storage conditions, and results of the study.

TABLE 17

Observations for batches NB538-043, NB538-044, NB538-045, and NB538-046

| Sampling | | Bottle | | | | Impurities (%) | | | |
|---|---|---|---|---|---|---|---|---|---|
| Time Point | Condition | Type | pH | Appearance | Assay (%) | A | D | UD | Total |

Batch Type/Size Batch # NB538-043 (100 mg/mL); Batch Size: 200 mL
Packaging Bottle Capacity: 120 cc HDPE; 30 cc Amber Glass; Bottles were purged with nitrogen;
HDPE bottles not sealed; Amber glass bottles were induction sealed

| 0 Hour | NA | HDPE | 3.8 | NA | 99.3 | ND | 0.057 | ND | 0.06 |
| 7 Days | 60° C. | HDPE | 3.8 | Brown, clear | 99.6 | 0.76 | 0.053 | ND | 0.82 |
| 15 Days | 60° C. | Glass | NA | Brown, clear | NA | ND | 0.054 | ND | 0.05 |

TABLE 17-continued

Observations for batches NB538-043, NB538-044, NB538-045, and NB538-046

| Sampling Time Point | Bottle Condition | Type | pH | Appearance | Assay (%) | Impurities (%) | | | |
|---|---|---|---|---|---|---|---|---|---|
| | | | | | | A | D | UD | Total |
| Batch Type/Size Batch # NB538-044 (100 mg/mL); Batch Size: 200 mL Packaging Bottle Capacity: 120 cc HDPE, 30 cc Amber Glass; Bottles were purged with nitrogen; HDPE bottles not sealed; Amber glass bottles were induction sealed | | | | | | | | | |
| 0 Hour | NA | HDPE | 2.5 | Light yellow, clear | 100.0 | ND | 0.057 | ND | 0.06 |
| 7 Days | 60° C. | HDPE | 2.5 | Light brown, clear | 99.5 | 0.43 | 0.052 | ND | 0.48 |
| 15 Days | 60° C. | Glass | NA | NA | NA | 0.17 | 0.05 | ND | 0.22 |
| Batch Type/Size Batch # NB538-045 (100 mg/mL); Batch Size: 200 mL Packaging Bottle Capacity: 120 cc HDPE; 30 cc Amber Glass; Bottles were purged with nitrogen; HDPE bottles not sealed | | | | | | | | | |
| 0 Hour | NA | HDPE | 3.8 | Orange, clear | 99.7 | ND | 0.05 | ND | 0.05 |
| 15 Days | 60° C. | HDPE | NA | NA | NA | 0.08 | 0.05 | ND | 0.19 |
| Batch Type/Size Batch # NB538-046 (100 mg/mL); Batch Size: 200 mL Packaging Bottle Capacity: 120 cc HDPE 30 cc Amber Glass; Bottles were purged with nitrogen; HDPE bottles not sealed; Amber glass bottles were induction sealed | | | | | | | | | |
| 0 Hour | NA | HDPE | 2.5 | Orange, clear | 99.5 | ND | 0.05 | ND | 0.05 |
| 15 Days | 60° C. | Glass | NA | NA | NA | 0.25 | 0.05 | ND | 0.34 |
| Acceptance Criteria (Preliminary Target) | | pH Assay Impurities | | ≤5.0 90.0%-110.0% Impurity A NMT 5.0%, Any Unidentified Impurity: NMT 0.10%, Total Impurities: NMT 7.0% | | | | | |

UD—Unidentified,
ND—Not Detected,
NMT—Not More Than,
NA—Not Available,
HDPE—High Density Polyethylene Upon comparison of the results of generation of impurity A after storage for 15 days at 60° C., it was observed that batches NB538-044 and NB538-046, with relatively low pH, exhibited considerably higher levels of impurity A in comparison to batches NB538-043 and NB538-045. As seen earlier, formulations packaged in amber glass bottles showed relatively lower levels of impurity A, indicating that degradation of chlorpromazine hydrochloride to impurity A can be inhibited by purging with nitrogen and use of glass containers, possibly due to the lower oxygen permeability of glass in comparison to high density polyethylene (HDPE) containers.

Lowering the pH or addition of ascorbic acid did not result in an improvement in the stability of the product. On the contrary, lowering pH led to an increase in the level of impurity A. Nitrogen purging and use of glass containers led to a considerable improvement in the stability of the product. It was observed that the level of impurity A was lowest with formulations containing the least number of excipients, i.e., batches NB543-37 and NB543-043. Therefore, it was of interest to study the impact of pH on formulations without antioxidants, chelating agent, or coloring agent. Since impurity D (N-dimethyl chlorpromazine) was a process impurity and it did not increase during storage, it was not evaluated further.

In this study it was also observed that the formulation had an extremely bitter taste and, therefore, it was concluded that preparing formulations without increasing the level of sweetener or incorporation of a flavor might lead to poor patient compliance. Therefore, formulations prepared at various pH levels, with and without flavor, and with different levels of sweeteners, were evaluated.

Example 5

To evaluate the impact of pH on the stability and to improve palatability the following study was performed on oral liquid compositions according to the present disclosure comprising about 100 mg/mL chlorpromazine hydrochloride. In order to prevent excipient-induced degradation, formulations without antioxidant, chelating agent, or color were prepared. In order to improve the palatability of the product, orange flavor was included in the formulation for batch NB538-048, and the amount of sucralose was doubled in the formulations for batches NB538-049 and NB538-050. The pH of the respective formulations was controlled by varying the amount of sodium citrate in the composition. The compositions for batches NB538-047, NB538-048, NB538-049, and NB538-050 are shown in Table 18 below.

TABLE 18

Formulation compositions
Formulation Composition (Strength: 100 mg/mL)
Quantity in mg/mL (Batch Size: 200 mL)

| Ingredients | NB538-(Batch no mentioned below) | | | |
|---|---|---|---|---|
| | 47 | 48 | 49 | 50 |
| Chlotpromazine Hydrochloride | 100.000 | 100.000 | 100.000 | 100.000 |
| Sueralose, USP | 1.500 | 1.500 | 3.000 | 3.000 |
| Sodium Benzoate, NF | 1.000 | 1.000 | 1.000 | 1.000 |
| Sodium Citrate, Dihydrate, USP | | | | 2.610 |
| Citric Acid Anhydrous, USP | 3.393 | 3.393 | 3.393 | 3.393 |
| Natural and Artificial Orange Flavor | | 3.000 | 0.500 | 0.500 |
| Purified Water, USP | q.s to 1 mL | | | |

To prepare batches NB538-047, NB538-048, NB538-049, and NB538-050, sucralose was dissolved in purified water using an overhead stirrer. Citric acid and sodium citrate (if applicable) were added to this solution and mixed until a clear solution was obtained. Sodium benzoate was then added to this solution and mixed until a clear solution was obtained. Chlorpromazine hydrochloride was added and mixed until a clear solution was obtained. Natural and artificial orange flavor (if applicable), which is available in liquid form, was added and mixed for 5 minutes to allow uniform mixing of the flavor in the solution. The solution was then transferred to a volumetric flask and purified water was added q.s. to 200 mL. The resulting batches were then stored under certain conditions and monitored over time to determine the stability of the solutions. Table 19 provides the packaging details, storage conditions, and results of the study.

There was a negligible difference between the impurity A levels for batches NB538-047, NB538-048, NB538-049 and NB538-050. Thus, pH did not appear to have a significant impact on the stability of the formulation nor did the presence of flavor or the increase in the level of sucralose. Product discoloration was observed for the formulations packaged in HDPE bottles. The discoloration was primarily attributed to oxidation of the product.

As seen earlier, the level of impurity A was lowest in amber glass bottles purged with nitrogen prior to sealing. Although the formulation was relatively stable in glass bottles, HDPE bottles were further explored given that glass bottles are relatively difficult to handle and potentially could

TABLE 19

Observations for batches NB538-047, NB538-048, NB538-049, and NB538-050

| Sampling Time Point | Condition | Bottle Type | pH | Appearance | Assay (%) | Impurities (%) A | D | UD | Total |
|---|---|---|---|---|---|---|---|---|---|
| Batch Type/Size Batch # NB538-047 (100 mg/mL); Batch Size: 200 mL Packaging Bottle Capacity: 120 cc HDPE; bottles not sealed ||||||||||
| 0 Hour | NA | HDPE | 2.6 | Clear, Light Yellow | 99.4 | ND | 0.06 | ND | 0.06 |
| 7 Days | 60° C. | HDPE | NA | NA | 99.5 | 0.10 | 0.06 | ND | 0.16 |
| 15 Days | 60° C. | HDPE | 2.5 | Dark blue and grey, clear | 99.2 | 0.23 | 0.06 | ND | 0.29 |
| Batch Type/Size Batch # NB538-048 (100 mg/mL); Batch Size: 200 mL Packaging Bottle Capacity: 120 cc HDPE; bottles not sealed ||||||||||
| 0 Hour | NA | HDPE | 2.5 | Clear, Light Yellow | 99.4 | ND | 0.05 | ND | 0.05 |
| 7 Days | 60° C. | HDPE | NA | NA | 99.8 | 0.09 | 0.06 | ND | 0.15 |
| 15 Days | 60° C. | HDPE | 2.5 | Blue and grey, clear | 99.9 | 0.19 | 0.06 | ND | 0.25 |
| Batch Type/Size Batch # NB538-049 (100 mg/mL); Batch Size: 200 mL Packaging Bottle Capacity: 120 cc HDPE; 30 cc Amber Glass; Bottles were purged with nitrogen; HDPE bottles not sealed; Amber glass bottles were induction sealed ||||||||||
| 0 Hour | NA | HDPE | 2.6 | Clear liquid | 100.5 | ND | 0.05 | ND | 0.05 |
| 7 Days | 60° C. | HDPE | 2.5 | Light blue and grey, clear | 99.4 | 0.08 | 0.06 | ND | 0.13 |
| 15 Days | 60° C. | HDPE | NA | NA | 100.3 | 0.14 | 0.06 | ND | 0.20 |
| 15 Days | 60° C. | Glass | NA | NA | 99.3 | 0.13 | 0.06 | ND | 0.19 |
| Batch Type/Size Batch # NB538-050 (100 mg/mL); Batch Size: 200 mL Packaging Bottle Capacity: 120 cc HDPE; 30 cc Amber Glass; Bottles were purged with nitrogen; HDPE bottles not sealed; Amber glass bottles were induction sealed ||||||||||
| 0 Hour | NA | HDPE | 3.3 | NA | 98.7 | ND | 0.06 | ND | 0.06 |
| 7 Days | 60° C. | HDPE | NA | NA | NA | 0.07 | 0.07 | ND | 0.14 |
| 15 Days | 60° C. | HDPE | NA | NA | NA | 0.18 | 0.08 | ND | 0.29 |
| 15 Days | 60° C. | Glass | NA | NA | NA | 0.12 | 0.07 | ND | 0.21 |
| Acceptance Criteria (Preliminary Target) | | | pH Assay Impurities | | ≤5.0 90.0%-110.0% Impurity A NMT 5.0%, Any Unidentified Impurity: NMT 0.10%; Total Impurities: NMT 7.0% | | | | |

UD—Unidentified,
ND—Not Detected,
NMT—Not More Than,
NA—Not Available,
HDPE—High Density Polyethylene As postulated, the impurities levels for batches NB538-047, NB538-048, NB538-049 and NB538-050 were found to be relatively lower in comparison to the batches prepared earlier containing ascorbic acid, sodium metabisulfite, or EDTA. The level of impurity A did not exceed the levels observed with the batches prepared earlier even in the absence of an antioxidant or a chelating agent in the formulation.

affect patient compliance. Further efforts were directed towards obtaining a stable formulation packaged in non-glass containers.

The pH, presence of flavor, or increase in the level of sucralose did not impact the level of impurity A in the product. Formulations packaged in HDPE bottles without headspace nitrogen purging showed discoloration under accelerated storage conditions. Samples from the containers with headspace purged with nitrogen prior to sealing showed the lowest level of impurity A. Since excessive headspace in the bottles could potentiate oxidative degradation, it was postulated that it would be advantageous to package the with the least possible headspace. Additionally, it was postulated that different primary packaging configurations, i.e., bottles with low permeability to oxygen, should be evaluated.

Citric acid and sodium citrate had an impact on the pH and consequently the level of impurities. It was seen that the stability of the formulations was affected by pH. Absence or low levels of citric acid or sodium citrate did not result in improvement of stability. Acceptable stability and consistent pH values upon short term storage were achieved at the finalized levels of citric acid and sodium citrate.

Example 6

To further evaluate the stability of oral liquid compositions according to the present disclosure, a study was performed on the compositions packaged in PET bottles with minimal headspace. Polyethylene terephthalate (PET) containers exhibit relatively low oxygen permeability in comparison to HDPE bottles. Since the generation of impurity A was a result of oxidative degradation, it was of interest to evaluate the stability of the product in PET bottles.

Results of the previous examples showed that the level of impurity A was lowest for formulations without antioxidants or chelating agents. Therefore, those were excluded from the formulations. Results also showed that the product exhibited relatively lower levels of impurity A when the container headspace was purged with nitrogen during packaging. Therefore, the bottle headspace was purged with nitrogen and induction sealed prior to storage for evaluation of stability. Since the headspace in the bottles could also potentiate oxidative degradation, it was minimized as much as possible by filling 120 ml product in 120 cc PET bottles. The formulation composition for batch NB538-057 is shown in Table 20 below.

TABLE 20

Formulation composition
Formulation Composition: NB538-057 (Strength: 100 mg/mL)
Batch Size: 1 Liter

| Ingredients | mg/mL |
| --- | --- |
| Chlorpromazine Hydrochloride | 100.000 |
| Sucralose, USP | 3.000 |
| Sodium Benzoate, NF | 1.000 |
| Sodium Citrate Dihydrate, USP | 5.220 |
| Citric Acid Anhydrous, USP | 3.393 |
| Purified Water, USP | q.s to 1 mL |

To prepare batch NB538-057, sucralose was dissolved in purified water using an overhead stirrer. Citric acid and sodium citrate were added to this solution and mixed until a clear solution was obtained. Sodium benzoate was then added to this solution and mixed until a clear solution was obtained. Chlorpromazine hydrochloride was added and mixed until a clear solution was obtained. The solution was then transferred to a volumetric flask and purified water was added q.s. to 200 mL. The resulting batch was then monitored over time to determine the stability of the solutions. Table 21 provides the packaging details, storage conditions, and results of the study.

TABLE 21

Observations for batch NB538-057

Batch # NB538-057 (100 mg/mL)

| Sampling Time Point | Condition | Bottle Type | pH | Appearance | Assay (%) | Impurities (%) | | | |
| --- | --- | --- | --- | --- | --- | --- | --- | --- | --- |
| | | | | | | A | D | UD | Total |
| Packaging Bottle Capacity: 120 cc; Bottles were purged with nitrogen and induction sealed | | | | | | | | | |
| 0 Hour | NA | PET | 3.9 | Light Yellow, Clear | 100.8 | ND | 0.06 | ND | 0.06 |
| 7 Days | 60° C. | PET | NA | NA | NA | 0.06 | 0.07 | ND | 0.13 |
| 15 Days | 60° C. | PET | NA | NA | 100.9 | 0.08 | 0.08 | ND | 0.16 |

| Acceptance Criteria (Preliminary Target) | | |
| --- | --- | --- |
| pH | ≤5.0 | |
| Assay | 90.0%-110.0% | |
| Impurities | Impurity A NMT 5.0%, Any Unidentified Impurity: NMT 0.10%; Total Impurities: NMT 7.0% | |

UD—Unidentified,
ND—Not Detected,
NMT—Not More Than,
NA—Not Available

After storage for 15 days at 60° C., the level of impurity A in this study was found to be the least among the tested formulations and packaging configurations until now. This indicated that packaging in PET bottles with minimal headspace was effective in controlling the impurity levels.

Although, the impurity A content was within the desired limit of no more than 0.20% after 15 days of storage at 60° C., it was anticipated that it may exceed that limit during the intended shelf life of the product. Given that the limit of impurity A for chlorpromazine hydrochloride oral concentrate was 5% (as per USP 42), however, further experiments to control impurity A were not conducted.

Minimizing the headspace and packaging in PET bottles with nitrogen purging had a considerable impact on the level of impurity A. Further experimentation to control the limit of impurity A was not deemed necessary. In spite of increasing the level of sucralose, the product was found bitter and therefore sucralose was increased further to improve the palatability of the product in the following experiments.

Example 7

To improve palatability, increasing the level of sucralose was evaluated. Additionally, to evaluate the stability of compositions according to the present disclosure including 100 mg/mL and 30 mg/mL chlorpromazine hydrochloride, the composition was tested in PET bottles.

Previous examples indicated that the level of impurity A can be controlled by minimizing the headspace and packaging in PET bottles with headspace nitrogen purging. In order to improve palatability, batch NB538-060 was prepared with a higher concentration of sucralose than the formulations prepared earlier. Formulation compositions for batches NB538-060 and NB538-061 are shown in Table 22 below.

TABLE 22

Formulation compositions
Formulation Composition
Quantity in mg/mL (Batch Size: 2 Liters

| Ingredients | NB538-060 (100 mg/ml) | NB538-061 (30 mg/ml) |
|---|---|---|
| Chlorpromazine Hydrochloride | 100.000 | 30.000 |
| Sucralose, USP | 30.000 | 9.000 |
| Sodium Benzoate, NF | 1.000 | 0.300 |
| Sodium Citrate, Dihydrate, USP | 5.220 | 1.566 |
| Citric Acid Arihydrous, USP | 3.393 | 1.018 |
| Purified Water, USP | q.s to 1 mL | q.s to 1 mL |

To prepare batches NB538-060 and NB538-061, sucralose was dissolved in purified water using an overhead stirrer. Citric acid, sodium citrate and ascorbic acid (if applicable) were added to this solution and mixed until a clear solution was obtained. Sodium benzoate was then added to this solution and mixed until a clear solution was obtained. Chlorpromazine hydrochloride was added and mixed until a clear solution was obtained. FD&C Yellow #6 (if applicable) was added and mixed until it completely dissolved. The solution was then transferred to a volumetric flask and purified water was added q.s. to 2000 mL. The resulting batches were then monitored over time to determine the stability of the solutions. Table 23 provides the packaging details, storage conditions, and results of the study.

TABLE 23

Observations for batches NB538-060 and NB538-061

| Sampling Time Point | Condition | Bottle Type | pH | Appearance | Assay (%) | Impurities (%) A | D | UD | Total |
|---|---|---|---|---|---|---|---|---|---|
| Batch # NB538-060 (100 mg/mL) Packaging Bottle Capacity: 240 cc; Bottles were purged with nitrogen and induction sealed ||||||||||
| 0 Hour | NA | PET | 3.9 | No Color, Clear | 98.9 | <0.05 | 0.06 | <0.05 | 0.06 |
| 7 Days | 60° C. | PET | NA | NA | 100.0 | <0.05 | 0.06 | <0.05 | 0.06 |
| 25 Days | 60° C. | PET | NA | NA | 99.8 | 0.16 | 0.06 | <0.05 | 0.22 |
| 2 Months | 40° C./75% RH | PET | 3.9 | NA | 99.3 | 0.06 | NA | <0.05 | 0.06 |
| 3 Months | 40° C./75% RH | PET | 3.9 | Clear liquid | 99.3 | <0.05 | NA | <0.05 | <0.05 |
| 3 Months | 25° C./60% RH | PET | 3.8 | Clear liquid | 99.2 | <0.05 | NA | <0.05 | <0.05 |
| Batch # NB538-061 (30 mg/mL) Packaging Bottle Capacity: 120 cc; Bottles were purged with nitrogen and induction sealed ||||||||||
| 0 Hour | NA | PET | 3.9 | Clear liquid | 99.4 | <0.05 | 0.06 | <0.05 | 0.06 |
| 17 Days | 60° C. | PET | NA | NA | 99.7 | 0.31 | 0.10 | <0.05 | 0.41 |
| 2 Months | 40° C./75% RH | PET | 3.9 | NA | 99.0 | 0.11 | <0.05 | <0.05 | 0.11 |
| 3 Months | 40° C./75% RH | PET | 4.0 | Clear liquid | 99.6 | 0.17 | NA | <0.05 | 0.17 |
| 3 Months | 25° C./60% RH | PET | 4.0 | Clear liquid | 99.6 | <0.05 | NA | <0.05 | <0.05 |

| Acceptance Criteria (Preliminary Target) | pH | 2.0-5.0 |
|---|---|---|
| | Assay | 90.0%-110.0% |
| | Impurities | Impurity A NMT 5.0% Any Unidentified Impurity: NMT 0.10%; Total Impurities: NMT 7.0% |

UD—Unidentified,
ND—Not Detected,
NMT—Not More Than,
NA—Not Available

Considering the nominal analytical variation, there was nearly no decrease in the drug assay after storage for 25 days or 15 days at 60° C., and there was little or no change in pH and appearance after 3 months of storage at 25° C./60/a RH or 40° C./75% RH for either of the strengths. The level of impurity A and total impurities were well below their respective limits. Therefore, the formulation and packaging configuration were deemed suitable for scale-up and process development studies.

Example 8

The following examples was performed to determine the effectiveness of sodium benzoate as a preservative at its respective concentration in oral liquid compositions according to the present disclosure comprising 100 mg/mL and 30 mg/mL chlorpromazine hydrochloride. Batches with varying concentrations of sodium benzoate were prepared for antimicrobial effectiveness test (AET) evaluation as per USP (United States Pharmacopoeia) Version 42. The concentrations of the preservatives in the drug product were selected empirically. The compositions of the evaluated formulations are provided in Table 24 below.

TABLE 24

Formulation composition
Formulation Composition for AET Studies
Quantity in mg/mL (Batch Size: 1 Liter)

| (Strength: 100 mg/mL) | Batch Number | | | | |
| --- | --- | --- | --- | --- | --- |
| | NB538-062 | NB538-063 | NB538-064 | NB538-065 | NB538-066 |
| Chlorpromazine Hydrochloride | 100.000 | 100.000 | 100.000 | 100.000 | 100.000 |
| Sucralose, USP | 30.000 | 30.000 | 30.000 | 30.000 | 30.000 |
| Sodium Benzoate, NF | | 0.500 | 1.000 | 1.500 | 2.000 |
| Sodium Citrate, Dihydrate, USP | 5.220 | 5.220 | 5.220 | 5.220 | 5.220 |
| Citric Acid Anhydrous, USP | 3.393 | 3.393 | 3.393 | 3.393 | 3.393 |
| Purified Water, USP | q.s. to 1 mL | q.s. to 1 mL | q.s. to 1 mL | q.s. to 1 mL | q.s. to 1 mL |

| (Strength: 30 mg/mL) | Batch Number | | | | |
| --- | --- | --- | --- | --- | --- |
| | NB538-067 | NB538-074 | NB538-069 | NB538-070 | NB538-071 |
| Chlorpromazine Hydrochloride | 30.000 | 30.000 | 30.000 | 30.000 | 30.000 |
| Sucralose, USP | 9.000 | 9.000 | 9.000 | 9.000 | 9.000 |
| Sodium Benzoate, NF | | 0.150 | 0.300 | 0.450 | 0.600 |
| Sodium Citrate, Dihydrate, USP | 1.566 | 1.566 | 1.566 | 1.566 | 1.566 |
| Citric Acid Anhydrous, USP | 1.018 | 1.018 | 1.018 | 1.018 | 1.018 |
| Purified Water, USP | q.s. to 1 mL | q.s. to 1 mL | q.s. to 1 mL | q.s. to 1 mL | q.s. to 1 mL |

To prepare batches NB538-062, NB538-063, NB538-064, NB538-065, NB538-066, NB538-067, NB538-074, NB538-069, NB538-070, and NB538-071, sucralose was dissolved in purified water using an overhead stirrer. Citric acid, sodium citrate and sodium benzoate (if applicable) were added to this solution and mixed until a clear solution was obtained. Chlorpromazine hydrochloride was added and mixed until a clear solution was obtained. The solution was then transferred to a volumetric flask and purified water was added q.s. to 1000 mL. Each batch was then assayed to determine the starting concentration of chlorpromazine hydrochloride as shown in Table 25 below, and the efficacy results of sodium benzoate as a preservative are shown for the batches in Tables 26-35 below.

TABLE 25

Assay of Chlorpromazine Hydrochloride and Sodium Benzoate at Time Zero

| Batch Number | Sodium Benzoate Content (% w/v) | Chlorpromazine Hydrochloride Assay (% Label Claim) |
| --- | --- | --- |
| NB538-062 | 0.000 | 100.1 |
| NB538-063 | 0.048 | 99.0 |
| NB538-064 | 0.970 | 100.3 |
| NB538-065 | 0.149 | 100.0 |
| NB538-066 | 0.198 | 99.4 |
| NB538-067 | 0.0 | 99.3 |
| NB538-074 | 0.015 | 100.1 |
| NB538-069 | 0.030 | 99.5 |
| NB538-070 | 0.045 | 99.9 |
| NB538-071 | 0.059 | 99.4 |

TABLE 26

AET-Efficacy Results for Batch NB538-062 (100 mg/ml); Sodium Benzoate Concentration: 0.00% w/v Lot # NB538-062  Description: Chlorpromazine HCl Oral Concentrate 100 mg/mL; Batch #1

| GBL# 548678/1 | | S. aureus | | E. coli | | P. aeruginosa | | B. cepacia | |
|---|---|---|---|---|---|---|---|---|---|
| | | Survivors | $Log_{10}$ reduction | Survivors | $Log_{10}$ reduction | Survivors | $Log_{10}$ reduction | Survivors | $Log_{10}$ reduction |
| Time-0 | cfu/mL $log_{10}$ | $4.3 \times 10^6$ 5.6 | N/A | $5.5 \times 10^5$ 5.7 | N/A | $3.8 \times 10^5$ 5.6 | N/A | $4.4 \times 10^5$ 5.6 | N/A |
| | Specifications | | | | $1 \times 10^5 - 1 \times 10^6$ cfu/mL | | | | |
| Day-14 | cfu/mL $log_{10}$ | <100 <2 | ≥3.6 | <100 <2 | ≥3.7 | <100 <2 | ≥3.6 | <100 <2 | ≥3.6 |
| | Specifications | | | | ≥1.0 $log_{10}$ from Time-0 | | | | |
| Day-28 | cfu/mL $log_{10}$ | <100 <2 | ≥3.6 | <100 <2 | ≥3.7 | <100 <2 | ≥3.6 | <100 <2 | ≥3.6 |
| | Specifications | | | | No increase from Day-14 | | | | |

| GBL# 548678/1 | | C. albicans | | A. brasiliensis | |
|---|---|---|---|---|---|
| | | Survivors | $Log_{10}$ reduction | Survivors | $Log_{10}$ reduction |
| Time-0 | cfu/mL $log_{10}$ | $1.3 \times 10^5$ 5.1 | N/A | $1.7 \times 10^5$ 5.2 | N/A |
| | Specifications | | $1 \times 10^5 - 1 \times 10^6$ cfu/mL | | |
| Day-14 | cfu/mL $log_{10}$ | <100 <2 | ≥3.1 | $2.6 \times 10^4$ 4.4 | 0.8 |
| | Specifications | | No increase from Time-0 | | |
| Day-28 | cfu/mL $log_{10}$ | <100 <2 | ≥3.1 | $2.0 \times 10^3$ 3.3 | 1.9 |
| | Specifications | | No increase from Time-0 | | |

Legend:
cfu = colony forming units,
N/A = Not Applicable,
Time-0 = Inoculum Recovery,
No increase = in counts is defined as not more than 0.5 $log_{10}$ unit more than the value to which it is compared.

TABLE 27

AET-Efficacy Results for Batch NB538-063 (100 mg/ml); Sodium Benzoate Concentration: 0.50% w/v Lot # NB538-063  Description: Chlorpromazine HCl Oral Concentrate 100 mg/mL; Batch #2

| GBL# 548678/2 | | S. aureus | | E. coli | | P. aeruginosa | | B. cepacia | |
|---|---|---|---|---|---|---|---|---|---|
| | | Survivors | $Log_{10}$ reduction | Survivors | $Log_{10}$ reduction | Survivors | $Log_{10}$ reduction | Survivors | $Log_{10}$ reduction |
| Time-0 | cfu/mL $log_{10}$ | $4.3 \times 10^5$ 5.6 | N/A | $5.5 \times 10^5$ 5.7 | N/A | $3.8 \times 10^5$ 5.6 | N/A | $4.4 \times 10^5$ 5.6 | N/A |
| | Specifications | | | | $1 \times 10^5 - 1 \times 10^6$ cfu/mL | | | | |
| Day-14 | cfu/mL $log_{10}$ | <100 <2 | ≥3.6 | <100 <2 | ≥3.7 | <100 <2 | ≥3.6 | <100 <2 | ≥3.6 |
| | Specifications | | | | ≥1.0 $log_{10}$ from Time-0 | | | | |
| Day-28 | cfu/mL $log_{10}$ | <100 <2 | ≥3.6 | <100 <2 | ≥3.7 | <100 <2 | ≥3.6 | <100 <2 | ≥3.6 |
| | Specifications | | | | No increase from Day-14 | | | | |

| GBL# 548678/2 | | C. albicans | | A. brasiliensis | |
|---|---|---|---|---|---|
| | | Survivors | $Log_{10}$ reduction | Survivors | $Log_{10}$ reduction |
| Time-0 | cfu/mL $log_{10}$ | $1.3 \times 10^5$ 5.1 | N/A | $1.7 \times 10^5$ 5.2 | N/A |
| | Specifications | | $1 \times 10^5 - 1 \times 10^6$ cfu/mL | | |
| Day-14 | cfu/mL $log_{10}$ | <100 <2 | ≥3.1 | $2.2 \times 10^3$ 3.3 | 1.9 |
| | Specifications | | No increase from Time-0 | | |

TABLE 27-continued

AET-Efficacy Results for Batch NB538-063 (100 mg/ml); Sodium Benzoate Concentration: 0.50% w/v Lot # NB538-063     Description: Chlorpromazine HCl Oral Concentrate 100 mg/mL; Batch #2

| | | | | | | |
|---|---|---|---|---|---|---|
| Day-28 | cfu/mL<br>$\log_{10}$ | <100<br><2 | | ≥3.1 | $1.1 \times 10^3$<br>3.0 | 2.2 |
| Specifications | | | | No increase from Time-0 | | |

Legend:
cfu = colony forming units,
N/A = Not Applicable,
Time-0 = Inoculum Recovery,
No increase = in counts is defined as not more than 0.5 $\log_{10}$ unit more than the value to which it is compared.

TABLE 28

AET-Efficacy Results for Batch NB538-064 (100 mg/ml); Sodium Benzoate Concentration: 0.100% w/v Lot # NB538-063     Description: Chlorpromazine HCl Oral Concentrate 100 mg/mL; Batch #3

| | *S. aureus* | | *E. coli* | | *P. aeruginosa* | | *B. cepacia* | |
|---|---|---|---|---|---|---|---|---|
| GBL# 548678/3 | Survivors | $\text{Log}_{10}$ reduction | Survivors | $\text{Log}_{10}$ reduction | Survivors | $\text{Log}_{10}$ reduction | Survivors | $\text{Log}_{10}$ reduction |
| Time-0   cfu/mL<br>$\log_{10}$ | $4.3 \times 10^5$<br>5.6 | N/A | $5.5 \times 10^5$<br>5.7 | N/A | $3.8 \times 10^5$<br>5.6 | N/A | $4.4 \times 10^5$<br>5.6 | N/A |
| Specifications | | | | $1 \times 10^5 - 1 \times 10^6$ cfu/mL | | | | |
| Day-14   cfu/mL<br>$\log_{10}$ | <100<br><2 | ≥3.6 | <100<br><2 | ≥3.7 | <100<br><2 | ≥3.6 | <100<br><2 | ≥3.6 |
| Specifications | | | | ≥1.0 $\log_{10}$ from Time-0 | | | | |
| Day-28   cfu/mL<br>$\log_{10}$ | <100<br><2 | ≥3.6 | <100<br><2 | ≥3.7 | <100<br><2 | ≥3.6 | <100<br><2 | ≥3.6 |
| Specifications | | | | No increase from Day-14 | | | | |

| | | *C. albicans* | | *A. brasiliensis* | |
|---|---|---|---|---|---|
| | GBL# 548678/3 | Survivors | $\text{Log}_{10}$ reduction | Survivors | $\text{Log}_{10}$ reduction |
| | Time-0   cfu/mL<br>$\log_{10}$ | $1.3 \times 10^5$<br>5.1 | N/A | $1.7 \times 10^5$<br>5.2 | N/A |
| | Specifications | | $1 \times 10^5 - 1 \times 10^6$ cfu/mL | | |
| | Day-14   cfu/mL<br>$\log_{10}$ | <100<br><2 | ≥3.1 | $2.3 \times 10^3$<br>3.4 | 1.8 |
| | Specifications | | | No increase from Time-0 | |
| | Day-28   cfu/mL<br>$\log_{10}$ | <100<br><2 | ≥3.1 | $1.2 \times 10^3$<br>3.1 | 2.1 |
| | Specifications | | | No increase from Time-0 | |

Legend:
cfu = colony forming units,
N/A = Not Applicable,
Time-0 = Inoculum Recovery,
No increase = in counts is defined as not more than 0.5 $\log_{10}$ unit more than the value to which it is compared.

TABLE 29

AET-Efficacy Results for Batch NB538-065 (100 mg/ml); Sodium Benzoate Concentration: 0.150% w/v Lot # NB538-065     Description: Chlorpromazine HCl Oral Concentrate 100 mg/mL; Batch #4

| | *S. aureus* | | *E. coli* | | *P. aeruginosa* | | *B. cepacia* | |
|---|---|---|---|---|---|---|---|---|
| GBL# 548678/4 | Survivors | $\text{Log}_{10}$ reduction | Survivors | $\text{Log}_{10}$ reduction | Survivors | $\text{Log}_{10}$ reduction | Survivors | $\text{Log}_{10}$ reduction |
| Time-0   cfu/mL<br>$\log_{10}$ | $4.3 \times 10^5$<br>5.6 | N/A | $5.5 \times 10^5$<br>5.7 | N/A | $3.8 \times 10^5$<br>5.6 | N/A | $4.4 \times 10^5$<br>5.6 | N/A |
| Specifications | | | | $1 \times 10^5 - 1 \times 10^6$ cfu/mL | | | | |
| Day-14   cfu/mL<br>$\log_{10}$ | <100<br><2 | ≥3.6 | <100<br><2 | ≥3.7 | <100<br><2 | ≥3.6 | <100<br><2 | ≥3.6 |
| Specifications | | | | ≥1.0 $\log_{10}$ from Time-0 | | | | |

TABLE 29-continued

AET-Efficacy Results for Batch NB538-065 (100 mg/ml); Sodium Benzoate Concentration: 0.150% w/v Lot # NB538-065  Description: Chlorpromazine HCl Oral Concentrate 100 mg/mL; Batch #4

| | | | | | | | | |
|---|---|---|---|---|---|---|---|---|
| Day-28 | cfu/mL $\log_{10}$ | <100 <2 | ≥3.6 | <100 <2 | ≥3.7 | <100 <2 | ≥3.6 | <100 <2 | ≥3.6 |
| Specifications | | | | | No increase from Day-14 | | | | |

| | | | C. albicans | | A. brasiliensis | |
|---|---|---|---|---|---|---|
| | GBL# 548678/4 | | Survivors | $\mathrm{Log}_{10}$ reduction | Survivors | $\mathrm{Log}_{10}$ reduction |
| Time-0 | | cfu/mL $\log_{10}$ | $1.3 \times 10^5$ 5.1 | N/A | $1.7 \times 10^5$ 5.2 | N/A |
| Specifications | | | | $1 \times 10^5 - 1 \times 10^6$ cfu/mL | | |
| Day-14 | | cfu/mL $\log_{10}$ | <100 <2 | ≥3.1 | $2.6 \times 10^3$ 3.4 | 1.8 |
| Specifications | | | | No increase from Time-0 | | |
| Day-28 | | cfu/mL $\log_{10}$ | <100 <2 | ≥3.1 | $1.4 \times 10^3$ 3.1 | 2.1 |
| Specifications | | | | No increase from Time-0 | | |

Legend:
cfu = colony forming units,
N/A = Not Applicable,
Time-0 = Inoculum Recovery,
No increase = in counts is defined as not more than 0.5 $\log_{10}$ unit more than the value to which it is compared.

TABLE 30

AET-Efficacy Results for Batch NB538-065 (100 mg/ml); Sodium Benzoate Concentration: 0.200% w/v Lot # NB538-066  Description: Chlorpromazine HCl Oral Concentrate 100 mg/mL; Batch #5

| | S. aureus | | E. coli | | P. aeruginosa | | B. cepacia | |
|---|---|---|---|---|---|---|---|---|
| GBL# 548678/5 | Survivors | $\mathrm{Log}_{10}$ reduction | Survivors | $\mathrm{Log}_{10}$ reduction | Survivors | $\mathrm{Log}_{10}$ reduction | Survivors | $\mathrm{Log}_{10}$ reduction |
| Time-0 cfu/mL $\log_{10}$ | $4.3 \times 10^5$ 5.6 | N/A | $5.5 \times 10^5$ 5.7 | N/A | $3.8 \times 10^5$ 5.6 | N/A | $4.4 \times 10^5$ 5.6 | N/A |
| Specifications | | | | $1 \times 10^5 - 1 \times 10^6$ cfu/mL | | | | |
| Day-14 cfu/mL $\log_{10}$ | <100 <2 | ≥3.6 | <100 <2 | ≥3.7 | <100 <2 | ≥3.6 | <100 <2 | ≥3.6 |
| Specifications | | | | ≥1.0 $\log_{10}$ from Time-0 | | | | |
| Day-28 cfu/mL $\log_{10}$ | <100 <2 | ≥3.6 | <100 <2 | ≥3.7 | <100 <2 | ≥3.6 | <100 <2 | ≥3.6 |
| Specifications | | | | No increase from Day-14 | | | | |

| | | | C. albicans | | A. brasiliensis | |
|---|---|---|---|---|---|---|
| | GBL# 548678/5 | | Survivors | $\mathrm{Log}_{10}$ reduction | Survivors | $\mathrm{Log}_{10}$ reduction |
| Time-0 | | cfu/mL $\log_{10}$ | $1.3 \times 10^5$ 5.1 | N/A | $1.7 \times 10^5$ 5.2 | N/A |
| Specifications | | | | $1 \times 10^5 - 1 \times 10^6$ cfu/mL | | |
| Day-14 | | cfu/mL $\log_{10}$ | <100 <1 | ≥3.1 | $1.9 \times 10^3$ 3.3 | 1.9 |
| Specifications | | | | No increase from Time-0 | | |
| Day-28 | | cfu/mL $\log_{10}$ | <100 <2 | ≥3.1 | $1.0 \times 10^3$ 3.0 | 2.2 |
| Specifications | | | | No increase from Time-0 | | |

Legend:
cfu = colony forming units,
N/A = Not Applicable,
Time-0 = Inoculum Recovery,
No increase = in counts is defined as not more than 0.5 $\log_{10}$ unit more than the value to which it is compared.

TABLE 31

AET-Efficacy Results for Batch NB538-067 (30 mg/ml); Sodium Benzoate Concentration: 0.00% w/v Lot # NB538-067 — Description: Chlorpromazine HCl Oral Concentrate 30 mg/mL; Sodium Benzoate Concentration 0%

| GBL# 552776/1 | | *S. aureus* Survivors | $Log_{10}$ reduction | *E. coli* Survivors | $Log_{10}$ reduction | *P. aeruginosa* Survivors | $Log_{10}$ reduction | *B. cepacia* Survivors | $Log_{10}$ reduction |
|---|---|---|---|---|---|---|---|---|---|
| Time-0 | cfu/mL $log_{10}$ | $1.1 \times 10^6$ 6.0 | N/A | $5.9 \times 10^5$ 5.8 | N/A | $5.4 \times 10^5$ 5.7 | N/A | $5.1 \times 10^5$ 5.7 | N/A |
| Specifications | | | | $1 \times 10^5 - 1 \times 10^6$ cfu/mL | | | | | |
| Day-14 | cfu/mL $log_{10}$ | <10 <1 | ≥5.0 | <10 <1 | ≥4.8 | <10 <1 | ≥4.7 | <10 <1 | ≥4.7 |
| Specifications | | | | ≥1.0 $log_{10}$ from Time-0 | | | | | |
| Day-28 | cfu/mL $log_{10}$ | <10 <1 | ≥5.0 | <10 <1 | ≥4.8 | <10 <1 | ≥4.7 | <10 <1 | ≥4.7 |
| Specifications | | | | No increase from Day-14 | | | | | |

| GBL# 552776/1 | | *C. albicans* Survivors | $Log_{10}$ reduction | *A. brasiliensis* Survivors | $Log_{10}$ reduction |
|---|---|---|---|---|---|
| Time-0 | cfu/mL $log_{10}$ | $1.4 \times 10^5$ 5.1 | N/A | $1.9 \times 10^5$ 5.3 | N/A |
| Specifications | | | $1 \times 10^5 - 1 \times 10^6$ cfu/mL | | |
| Day-14 | cfu/mL $log_{10}$ | <10 <1 | ≥4.1 | $3.3 \times 10^4$ 4.5 | 0.8 |
| Specifications | | | No increase from Time-0 | | |
| Day-28 | cfu/mL $log_{10}$ | <10 <1 | ≥4.1 | <10 <1 | ≥4.3 |
| Specifications | | | No increase from Time-0 | | |

Legend:
cfu = colony forming units,
N/A = Not Applicable,
Time-0 = Inoculum Recovery,
No increase = in counts is defined as not more than 0.5 $log_{10}$ unit more than the value to which it is compared.

TABLE 32

AET-Efficacy Results for Batch NB538-074 (30 mg/ml); Sodium Benzoate Concentration: 0.015% w/v Lot # NB538-074 — Description: Chlorpromazine HCl Oral Concentrate 30 mg/mL; Sodium Benzoate Concentration 0.015%

| GBL# 552776/2 | | *S. aureus* Survivors | $Log_{10}$ reduction | *E. coli* Survivors | $Log_{10}$ reduction | *P. aeruginosa* Survivors | $Log_{10}$ reduction | *B. cepacia* Survivors | $Log_{10}$ reduction |
|---|---|---|---|---|---|---|---|---|---|
| Time-0 | cfu/mL $log_{10}$ | $1.1 \times 10^6$ 6.0 | N/A | $5.9 \times 10^5$ 5.8 | N/A | $5.4 \times 10^5$ 5.7 | N/A | $5.1 \times 10^5$ 5.7 | N/A |
| Specifications | | | | $1 \times 10^5 - 1 \times 10^6$ cfu/mL | | | | | |
| Day-14 | cfu/mL $log_{10}$ | <10 <1 | ≥5.0 | <10 <1 | ≥4.8 | <10 <1 | ≥4.7 | <10 <1 | ≥4.7 |
| Specifications | | | | ≥1.0 $log_{10}$ from Time-0 | | | | | |
| Day-28 | cfu/mL $log_{10}$ | <10 <1 | ≥5.0 | <10 <1 | ≥4.8 | <10 <1 | ≥4.7 | <10 <1 | ≥4.7 |
| Specifications | | | | No increase from Day-14 | | | | | |

| GBL# 552776/2 | | *C. albicans* Survivors | $Log_{10}$ reduction | *A. brasiliensis* Survivors | $Log_{10}$ reduction |
|---|---|---|---|---|---|
| Time-0 | cfu/mL $log_{10}$ | $1.4 \times 10^5$ 5.1 | N/A | $1.9 \times 10^5$ 5.3 | N/A |
| Specifications | | | $1 \times 10^5 - 1 \times 10^6$ cfu/mL | | |
| Day-14 | cfu/mL $log_{10}$ | <10 <1 | ≥4.1 | $2.5 \times 10^4$ 4.4 | 0.9 |
| Specifications | | | No increase from Time-0 | | |

TABLE 32-continued

AET-Efficacy Results for Batch NB538-074 (30 mg/ml); Sodium Benzoate Concentration: 0.015% w/v

| Lot # NB538-074 | | Description: Chlorpromazine HCl Oral Concentrate 30 mg/mL; Sodium Benzoate Concentration 0.015% | | | |
|---|---|---|---|---|---|
| Day-28 | cfu/mL | <10 | ≥4.1 | <10 | ≥4.3 |
| | $\log_{10}$ | <1 | | <1 | |
| Specifications | | | No increase from Time-0 | | |

Legend:
cfu = colony forming units,
N/A = Not Applicable,
Time-0 = Inoculum Recovery,
No increase = in counts is defined as not more than 0.5 $\log_{10}$ unit more than the value to which it is compared.

TABLE 33

AET-Efficacy Results for Batch NB538-069 (30 mg/ml); Sodium Benzoate Concentration: 0.030% w/v

| Lot # NB538-069 | | | | Description: Chlorpromazine HCl Oral Concentrate 30 mg/mL; Sodium Benzoate Concentration 0.030% | | | | |
|---|---|---|---|---|---|---|---|---|
| | | *S. aureus* | | *E. coli* | | *P. aeruginosa* | | *B. cepacia* | |
| GBL# 552776/3 | | Survivors | $\log_{10}$ reduction | Survivors | $\log_{10}$ reduction | Survivors | $\log_{10}$ reduction | Survivors | $\log_{10}$ reduction |
| Time-0 | cfu/mL | $1.1 \times 10^6$ | N/A | $5.9 \times 10^5$ | N/A | $5.4 \times 10^5$ | N/A | $5.1 \times 10^5$ | N/A |
| | $\log_{10}$ | 6.0 | | 5.8 | | 5.7 | | 5.7 | |
| Specifications | | | | $1 \times 10^5 - 1 \times 10^6$ cfu/mL | | | | | |
| Day-14 | cfu/mL | <10 | ≥5.0 | <10 | ≥4.8 | <10 | ≥4.7 | <10 | ≥4.7 |
| | $\log_{10}$ | <1 | | <1 | | <1 | | <1 | |
| Specifications | | | | ≥1.0 $\log_{10}$ from Time-0 | | | | | |
| Day-28 | cfu/mL | <10 | ≥5.0 | <10 | ≥4.8 | <10 | ≥4.7 | <10 | ≥4.7 |
| | $\log_{10}$ | <1 | | <1 | | <1 | | <1 | |
| Specifications | | | | No increase from Day-14 | | | | | |

| | | *C. albicans* | | *A. brasiliensis* | |
|---|---|---|---|---|---|
| GBL# 552776/3 | | Survivors | $\log_{10}$ reduction | Survivors | $\log_{10}$ reduction |
| Time-0 | cfu/mL | $1.4 \times 10^5$ | N/A | $1.9 \times 10^5$ | N/A |
| | $\log_{10}$ | 5.1 | | 5.3 | |
| Specifications | | | $1 \times 10^5 - 1 \times 10^6$ cfu/mL | | |
| Day-14 | cfu/mL | <10 | ≥4.1 | $2.5 \times 10^4$ | 0.7 |
| | $\log_{10}$ | <1 | | 4.6 | |
| Specifications | | | No increase from Time-0 | | |
| Day-28 | cfu/mL | <10 | ≥4.1 | <10 | ≥4.3 |
| | $\log_{10}$ | <1 | | <1 | |
| Specifications | | | No increase from Time-0 | | |

Legend:
cfu = colony forming units,
N/A = Not Applicable,
Time-0 = Inoculum Recovery,
No increase = in counts is defined as not more than 0.5 $\log_{10}$ unit more than the value to which it is compared.

TABLE 34

AET-Efficacy Results for Batch NB538-070 (30 mg/ml); Sodium Benzoate Concentration: 0.045% w/v

| Lot # NB538-070 | | | | Description: Chlorpromazine HCl Oral Concentrate 30 mg/mL; Sodium Benzoate Concentration 0.045% | | | | |
|---|---|---|---|---|---|---|---|---|
| | | *S. aureus* | | *E. coli* | | *P. aeruginosa* | | *B. cepacia* | |
| GBL# 552776/4 | | Survivors | $\log_{10}$ reduction | Survivors | $\log_{10}$ reduction | Survivors | $\log_{10}$ reduction | Survivors | $\log_{10}$ reduction |
| Time-0 | cfu/mL | $1.1 \times 10^6$ | N/A | $5.9 \times 10^5$ | N/A | $5.4 \times 10^5$ | N/A | $5.1 \times 10^5$ | N/A |
| | $\log_{10}$ | 6.0 | | 5.8 | | 5.7 | | 5.7 | |
| Specifications | | | | $1 \times 10^5 - 1 \times 10^6$ cfu/mL | | | | | |

TABLE 34-continued

AET-Efficacy Results for Batch NB538-070 (30 mg/ml); Sodium Benzoate Concentration: 0.045% w/v Lot # NB538-070 — Description: Chlorpromazine HCl Oral Concentrate 30 mg/mL; Sodium Benzoate Concentration 0.045%

| | | S. aureus | | E. coli | | P. aeruginosa | | B. cepacia | |
|---|---|---|---|---|---|---|---|---|---|
| Day-14 | cfu/mL log$_{10}$ | <10 <1 | ≥5.0 | <10 <1 | ≥4.8 | <10 <1 | ≥4.7 | <10 <1 | ≥4.7 |
| Specifications | | | | ≥1.0 log$_{10}$ from Time-0 | | | | | |
| Day-28 | cfu/mL log$_{10}$ | <10 <1 | ≥5.0 | <10 <1 | ≥4.8 | <10 <1 | ≥4.7 | <10 <1 | ≥4.7 |
| Specifications | | | | No increase from Day-14 | | | | | |

| | | C. albicans | | A. brasiliensis | |
|---|---|---|---|---|---|
| GBL# 552776/4 | | Survivors | Log$_{10}$ reduction | Survivors | Log$_{10}$ reduction |
| Time-0 | cfu/mL log$_{10}$ | 1.4 × 10$^5$ 5.1 | N/A | 1.9 × 10$^5$ 5.3 | N/A |
| Specifications | | | 1 × 10$^5$ – 1 × 10$^6$ cfu/mL | | |
| Day-14 | cfu/mL log$_{10}$ | <10 <1 | ≥4.1 | 5.2 × 10$^4$ 4.7 | 0.6 |
| Specifications | | | No increase from Time-0 | | |
| Day-28 | cfu/mL log$_{10}$ | <10 <1 | ≥4.1 | <10 <1 | ≥4.3 |
| Specifications | | | No increase from Time-0 | | |

Legend:
cfu = colony forming units,
N/A = Not Applicable,
Time-0 = Inoculum Recovery,
No increase = in counts is defined as not more than 0.5 log$_{10}$ unit more than the value to which it is compared.

TABLE 35

AET-Efficacy Results for Batch NB538-071 (30 mg/ml); Sodium Benzoate Concentration: 0.060% w/v Lot # NB538-071 — Description: Chlorpromazine HCl Oral Concentrate 30 mg/mL; Sodium Benzoate Concentration 0.060%

| | | S. aureus | | E. coli | | P. aeruginosa | | B. cepacia | |
|---|---|---|---|---|---|---|---|---|---|
| GBL# 552776/5 | | Survivors | Log$_{10}$ reduction | Survivors | Log$_{10}$ reduction | Survivors | Log$_{10}$ reduction | Survivors | Log$_{10}$ reduction |
| Time-0 | cfu/mL log$_{10}$ | 1.1 × 10$^6$ 6.0 | N/A | 5.9 × 10$^5$ 5.8 | N/A | 5.4 × 10$^5$ 5.7 | N/A | 5.1 × 10$^5$ 5.7 | N/A |
| Specifications | | | | 1 × 10$^5$ – 1 × 10$^6$ cfu/mL | | | | | |
| Day-14 | cfu/mL log$_{10}$ | <10 <1 | ≥5.0 | <10 <1 | ≥4.8 | <10 <1 | ≥4.7 | <10 <1 | ≥4.7 |
| Specifications | | | | ≥1.0 log$_{10}$ from Time-0 | | | | | |
| Day-28 | cfu/mL log$_{10}$ | <10 <1 | ≥5.0 | <10 <1 | ≥4.8 | <10 <1 | ≥4.7 | <10 <1 | ≥4.7 |
| Specifications | | | | No increase from Day-14 | | | | | |

| | | C. albicans | | A. brasiliensis | |
|---|---|---|---|---|---|
| GBL# 552776/5 | | Survivors | Log$_{10}$ reduction | Survivors | Log$_{10}$ reduction |
| Time-0 | cfu/mL log$_{10}$ | 1.4 × 10$^5$ 5.1 | N/A | 1.9 × 10$^5$ 5.3 | N/A |
| Specifications | | | 1 × 10$^5$ – 1 × 10$^6$ cfu/mL | | |
| Day-14 | cfu/mL log$_{10}$ | <10 <1 | ≥4.1 | 4.0 × 10$^4$ 4.6 | 0.7 |
| Specifications | | | No increase from Time-0 | | |
| Day-28 | cfu/mL log$_{10}$ | <10 <1 | ≥4.1 | <10 <1 | ≥4.3 |
| Specifications | | | No increase from Time-0 | | |

Legend:
cfu = colony forming units,
N/A = Not Applicable,
Time-0 = Inoculum Recovery,
No increase = in counts is defined as not more than 0.5 log$_{10}$ unit more than the value to which it is compared.

AET results showed that all the formulations tested in this study for both 100 mg/ml and 30 mg/ml chlorpromazine hydrochloride strengths met the acceptance criteria for category 3 products. The inherent antimicrobial effectiveness of the product, which may be due to the active ingredient in the tested compositions, chlorpromazine hydrochloride, is demonstrated by formulations NB538-062 and NB538-067, which passed the AET even in the absence of sodium benzoate. The concentration of sodium benzoate in the final formulation was kept at 0.030% and 0.100% w/v for the formulations for 30 mg/ml and 100 mg/ml chlorpromazine hydrochloride strengths, respectively. These concentrations were conservatively set to ensure the finished product stability upon multiple withdrawals since the product is packaged in a multi-use container.

Example 9

The following study was performed to evaluate the stability of oral liquid compositions according to the present disclosure upon subjecting them to freeze-thaw cycles. Exposure to extreme temperatures potentially can impact the solubility of the ingredients, accelerate degradation, and affect the physical and chemical stability of the product. For these studies, batches NB538-072 (30 mg/mL chlorpromazine hydrochloride) and NB538-073 (100 mg/mL) were prepared and packaged in 240 cc and 120 cc polyethylene terephthalate (PET) bottles, respectively. The bottles were nitrogen purged to minimize oxygen content in the headspace prior to sealing. Individual bottles were stored between −10 to −20° C. or 2-8° C. for 2 days per cycle and then thawed at 25° C./60/o RH or 40° C./75% RH for 2 days per cycle. The bottles were inspected visually for phase separation and appearance and analyzed for assay, impurities, pH, and appearance after 3 freeze cycles and thaw cycles each. The formulation compositions for batches NB538-072 and NB538-073 are shown in Table 36 below.

TABLE 36

Formulation compositions
Formulation Composition
Quantity in mg/mL (Batch Size: 4 Liters

| Ingredients | NB538-072 (30 mg/ml) | NB538-073 (100 mg/ml) |
|---|---|---|
| Chlorpromazine Hydrochloride | 30.000 | 100.000 |
| Sucralose, USP | 9.000 | 30.000 |
| Sodium Benzoate, NF | 0.300 | 1.000 |
| Sodium Citrate, Dihydrate, USP | 1.566 | 5.220 |
| Citric Acid Anhydrous, USP | 1.018 | 3.393 |
| Purified Water, USP | 968.116 | 898.387 |
| Density | 1.010 g/mL | 1.038 g/mL |

To prepare batches NB538-072 and NB538-073, sucralose was dissolved in purified water using an overhead stirrer. Citric acid and sodium citrate were added to this solution and mixed until a clear solution was obtained. Sodium benzoate was then added to this solution and mixed until a clear solution was obtained. Chlorpromazine hydrochloride was added and mixed until a clear solution was obtained. The resulting batches were packaged and then tested in freeze-thaw cycles. Table 37 provides the packaging details, storage conditions, and results of the study.

TABLE 37

Test Results

| Sampling Time Point | Condition | PH | Appearance | Assay (%) | Impurities (%) A | UD | Total |
|---|---|---|---|---|---|---|---|
| Batch # NB538-072 (30 mg/mL) Packaging Bottle Capacity: 120 cc PET; Bottles were purged with nitrogen and induction sealed | | | | | | | |
| 0 Hour | NA | 3.9 | clear liquid | 100.0 | NA | NA | NA |
| After 3 Cycles | Freeze: −10 to −20° C., Thaw: 40° C./75% RH | 3.9 | clear liquid, light pink | 96.9 | ≤0.05 | ≤0.05 | ≤0.05 |
| | Freeze: −10 to −20° C., Thaw: 25° C./60% RH | 3.9 | clear liquid, light pink | 96.6 | ≤0.05 | ≤0.05 | ≤0.05 |
| | Freeze: 2 to 8° C., Thaw: 40° C./75% RH | 3.9 | clear liquid, light pink | 96.5 | ≤0.05 | ≤0.05 | ≤0.05 |
| | Freeze: 2 to 8° C., Thaw: 25° C./60% RH | 3.9 | clear liquid, light pink | 93.9 | ≤0.05 | ≤0.05 | ≤0.05 |
| Batch # NB538-073 (100 mg/mL) Packaging Bottle Capacity: 240 cc PET; Bottles were purged with nitrogen and induction sealed | | | | | | | |
| 0 Hour | NA | 3.9 | clear liquid, light yellow | 99.7 | NA | NA | NA |
| After 3 Cycles | Freeze: −10 to −20° C., Thaw: 40° C./75% RH | 3.9 | clear liquid, light yellow | 97.5 | ≤0.05 | ≤0.05 | ≤0.05 |
| | Freeze: −10 to −20° C., Thaw: 25° C./60% RH | 3.9 | clear liquid, light yellow | 96.1 | ≤0.05 | ≤0.05 | ≤0.05 |
| | Freeze: 2 to 8° C., Thaw: 40° C./75% RH | 3.9 | clear liquid, light yellow | 97.0 | ≤0.05 | ≤0.05 | ≤0.05 |
| | Freeze: 2 to 8° C., Thaw: 2 to 5° C./60% RH | 3.9 | clear liquid, light yellow | 96.4 | ≤0.05 | ≤0.05 | ≤0.05 |

TABLE 37-continued

| | | | | Test Results | | | |
|---|---|---|---|---|---|---|---|
| Sampling | | | | | Impurities (%) | | |
| Time Point | Condition | PH | Appearance | Assay (%) | A | UD | Total |
| Acceptance Criteria (Preliminary Target) | | | Appearance pH Assay Impurities | Clear liquid (no discoloration or precipitation) 2.0-5.0 90.0%-110.0% Impurity A NMT 5.0%, Any Unidentified Impurity: NMT 0.10%; Total Impurities: NMT 7.0% | | | |

UD—Unidentified,
ND—Not Detected,
NMT—Not More Than,
NA—Not Available

The samples were found to be physically stable as precipitation was not observed throughout the duration of the study. The decrease in the assay values seen upon storage indicated that the active ingredient was susceptible to degradation when subjected to freeze-thaw cycles. However, all the results, irrespective of the freeze-thaw condition, met the specifications.

Samples from batch NB538-072 showed a slight discoloration, i.e., a pink shade was observed during the second freeze thaw cycle of the sample stored at 2-8° C. and during the third freeze thaw cycle of the sample stored at −10 to −20° C. Primarily, the discoloration was attributed to oxidative degradation. It was postulated that since the sample bottles were opened and transferred to a glass container for visual evaluation after every cycle, the loss of nitrogen and exposure to atmospheric oxygen led to oxidation, and thus discoloration. During routine storage and usage the chances of such discoloration would be minimal since the sample is not expected to be handled in such fashion.

Although, a decrease in assay was seen upon subjecting the samples to freeze thaw studies, the samples met the intended product specifications. Therefore, the product was deemed suitable for scale-up and process development studies.

Example 10

The following study was performed to evaluate the stability of oral liquid compositions according to the present disclosure including 100 mg/mL and 30 mg/mL chlorpromazine hydrochloride in presence of EDTA (ethylenedinitrilotetraacetic acid disodium salt dihydrate). During the manufacturing of the process optimization batches NB538-079, NB538-080, NB538-082 and NB538-083 (discussed below), discoloration (change in color) of the product was observed during bulk storage and stability studies. The color change was similar to that observed during the freeze-thaw studies. Literature review suggested that such discoloration is a result of the oxidation of chlorpromazine by metal ions. Phenothazine derivatives such as chlorpromazine HCl, perphenazine, and fluphenazine HCl are oxidized by metal ions to form colored products. It was postulated that the metal ion induced oxidation can be prevented by addition of EDTA to the formulation. Batches NB538-084 (100 mg/ml chlorpromazine hydrochloride) and NB538-085 (30 mg/ml) were prepared with the incorporation of EDTA into the respective formulation. Batches NB538-088 (100 mg/ml) and NB538-089 (30 mg/ml) were prepared for additional stability studies. The formulation compositions for Batches NB538-084, NB538-085, NB538-088, and NB538-089 are shown in Table 38 below.

TABLE 38

Formulation compositions
Formulation Composition
Quantity in mg/mL (Batch Size: 2 Liters

| Ingredients | NB538-084 (100 mg/ml) | NB538-085 (30 mg/ml) | NB538-088 (100 mg/ml) | NB538-089 (30 mg/ml) |
|---|---|---|---|---|
| Chlorpromazine Hydrochloride | 100.000 | 30.000 | 100.000 | 30.000 |
| Sucralose, USP | 30.000 | 9.000 | 30.000 | 9.000 |
| Sodium Benzoate, NF | 1.000 | 0.300 | 1.000 | 0.300 |
| Sodium Citrate, Dihydrate, USP | 5.220 | 1.566 | 5.220 | 1.566 |
| Citric Acid Anhydrous, USP | 3.393 | 1.018 | 3.393 | 1.018 |
| Disodium Edetate (EDTA) | 1.000 | 1.000 | 1.000 | 1.000 |
| Purified Water, USP | q.s. to 1 mL | q.s. to 1 mL | q.s. to 1 mL | q.s. to 1 mL |

To prepare batches NB538-084, NB538-085, NB538-088 and NB538-089, EDTA was dissolved in purified water using an overhead stirrer (for NB538-084 and NB538-085). Sucralose, citric acid, and sodium citrate were added to this solution and mixed until a clear solution was obtained (EDTA was added at this step for batches NB538-088 and NB538-089). Sodium benzoate was then added to this solution and mixed until a clear solution was obtained. Chlorpromazine hydrochloride was added and mixed until a clear solution was obtained. The solution was then transferred to a volumetric flask and purified water was added q.s. to 2000 mL. The resulting batches were then packaged, maintained under certain conditions, and monitored over time to determine the stability of the solutions. Table 39 and 40 provide the packaging details, storage conditions, and results of the study.

TABLE 39

Observations for batches NB538-084 and NB538-085

| Sampling Time Point | Condition | Appearance | pH | Assay (%) | EDTA Content (% w/v) | Impurities (%) A | UD | Total |
|---|---|---|---|---|---|---|---|---|
| Batch # NB538-085 (30 mg/mL) Packaging Bottle Configuration: 120 cc PET; Bottles were purged with nitrogen and induction sealed | | | | | | | | |
| 0 Hour | NA | clear liquid, light yellow | 3.9 | 100.0 | 0.107 | ≤0.05 | ≤0.05 | ≤0.05 |
| 7 Days | 60° C. | clear liquid, light yellow | 4.0 | 99.8 | 0.067 | 0.48 | ≤0.05 | 0.48 |
| 15 Days | 60° C. | clear liquid, light yellow | 4.1 | 99.8 | 0.056 | 0.57 | ≤0.05 | 0.57 |
| 1 Month | 40° C./75% RH | clear liquid, light yellow | 4.0 | 99.8 | 0.083 | 0.36 | ≤0.05 | 0.36 |
| 2 Months | 40° C./75% RH | clear liquid, light yellow | 4.1 | 99.4 | 0.065 | 0.49 | ≤0.05 | 0.49 |
| 3 Months | 40° C./75% RH | clear liquid, light yellow | 4.1 | 100.2 | 0.057 | 0.47 | ≤0.05 | 0.47 |
| 3 Months | 25° C./60% RH | clear liquid, light yellow | 3.9 | 99.3 | 0.091 | 0.17 | ≤0.05 | 0.17 |
| 6 Months | 25° C./60% RH | clear liquid, light yellow | 4.0 | 98.7 | 0.045 | 0.27 | ≤0.05 | 0.27 |
| Batch # NB538-084 (100 mg/mL) Packaging Bottle Configuration: 240 cc PET; Bottles were purged with nitrogen and induction sealed | | | | | | | | |
| 0 Hour | NA | clear liquid, light yellow | 3.9 | 100.2 | 0.102 | ≤0.05 | ≤0.05 | ≤0.05 |
| 7 Days | 60° C. | clear liquid, light yellow | 3.9 | 100.0 | 0.079 | 0.12 | ≤0.05 | 0.12 |
| 15 Days | 60° C. | clear liquid, light yellow | 3.9 | 100.6 | 0.077 | 0.14 | ≤0.05 | 0.14 |
| 1 Month | 40° C./75% RH | clear liquid, light yellow | 4.0 | 101.1 | 0.087 | 0.11 | ≤0.05 | 0.11 |
| 2 Months | 40° C./75% RH | clear liquid, light yellow | 3.9 | 99.0 | 0.071 | 0.14 | ≤0.05 | 0.14 |
| 3 Months | 40° C./75% RH | clear liquid, light yellow | 3.9 | 99.4 | 0.068 | 0.14 | ≤0.05 | 0.14 |
| 3 Months | 25° C./60% RH | clear liquid, light yellow | 3.9 | 99.8 | 0.091 | 0.06 | ≤0.05 | 0.06 |
| 6 Months | 25° C./60% RH | clear liquid, light yellow | 4.0 | 99.3 | 0.082 | 0.10 | ≤0.05 | 0.10 |

Acceptance Criteria:
pH 2.0-5.0
Assay 90.0%-110.0%
impurities Impurity A NMT 5.0%, Any Unidentified impurity: NMT 0.10%; Total Impurities: NMT 7.0%
EDTA Content 0.010 to 0.150% w/v UD—Unidentified,
ND—Not Detected,
NMT—Not More Than,
NA—Not Available

TABLE 40

Observations for batches NB538-088 and NB538-089

| Sampling Point Time | Condition | Appearance | pH | Assay (%) | EDTA Content (% w/v) | Sodium Benzoate (% w/v) | Impurities (%) A | UD | Total |
|---|---|---|---|---|---|---|---|---|---|
| Batch # NB538-089 (30 mg/mL) Packaging Bottle Configuration: 120 cc PET; Bottles were purged with nitrogen and induction sealed | | | | | | | | | |
| 0 Hour | NA | clear liquid, light yellow | 3.9 | 99.6 | N/A | 0.027 | ≤0.05 | ≤0.05 | ≤0.05 |
| 6 Months | 40° C./75% RH | clear liquid, light yellow | 4.1 | 98.4 | 0.045 | 0.027 | 0.58 | ≤0.05 | 0.58 |
| Batch # NB538-088 (100 mg/mL) Packaging Bottle Configuration: 240 cc PET; Bottles were purged with nitrogen and induction sealed | | | | | | | | | |
| 0 Hour | NA | clear liquid, light yellow | 3.9 | 98.9 | N/A | 0.099 | ≤0.05 | ≤0.05 | ≤0.05 |
| 6 Months | 40° C./75% RH | clear liquid, light yellow | 4.0 | 98.2 | 0.067 | 0.100 | 0.16 | ≤0.05 | 0.16 |

Acceptance Criteria:
Appearance Clear liquid (no discoloration)
H 2-5
Assay 90%-110%
Impurities Impurity A NMT 5.0%, Any Unidentified Impurity: NMT 0.10%; Total Impurities: NMT 7.0%
EDTA Content 0.010 to 0.150% w/v
Sodium benzoate 0.015-0.045% w/v (30 mg/ml); 0.050 to 0.150% w/v (100 mg/ml)

UD—Unidentified,
ND—Not Detected,
NMT—Not More Than,
NA—Not Available

All results for samples stored at controlled room temperature and humidity as well as accelerated conditions met the intended specifications after 6 months of storage at 40° C./75% RH. The samples did not exhibit discoloration during storage even under accelerated stability conditions for 6 months. It could be concluded that EDTA could successfully prevent discoloration of the product during storage.

Example 11

The following study was performed to evaluate water loss under various temperature and humidity conditions from oral liquid compositions according to the present disclosure comprising 100 mg/mL and 30 mg/mL chlorpromazine hydrochloride. Water loss from the finished product was evaluated by weighing and storing bottles at various conditions of temperature and humidity. Batches NB538-060 (100 mg/ml chlorpromazine hydrochloride) and NB538-072 (30 mg/ml), manufactured earlier without EDTA, were periodically weighed after storage at 40° C.±2° C./NMT 25% RH or 25° C.±2° C./40±5% RH. Batches NB538-086 (30 mg/ml) and NB538-087 (100 mg/ml) were manufactured with EDTA and periodically weighed after storage at 25° C.±2° C./60±5% RH or 40° C.±2° C./75±5% RH. Since presence of EDTA was not expected to have a significant impact on water loss from the formulations, water loss studies for formulations containing EDTA at 40° C.±2° C./NMT 25% RH or 25° C.±2° C./40±5% RH were directly performed on the stability batches. Batches NB538-060 and NB538-087 (100 mg/ml chlorpromazine hydrochloride) were packed in 240 cc PET bottles with nitrogen purging and induction seal. Batches NB538-072 and NB538-086 (30 mg/ml strength) were packed in 120 cc PET bottles with nitrogen purging and induction seal. The formulation compositions for batches NB538-086 (30 mg/ml) and NB538-087 are provided in Table 41 below.

TABLE 41

Formulation compositions
Formulation Composition
Quantity in mg/mL Batch Size: 750 ml (30 mg/ml), 1500 ml (100 mg/ml)

| Ingredients | NB538-086 (100 mg/ml) | NB538-087 (30 mg/ml) |
|---|---|---|
| Chlorpromazine Hydrochloride | 100.000 | 30.000 |
| Sucralose, USP | 30.000 | 9.000 |
| Sodium Benzoate, NF | 1.000 | 0.300 |
| Sodium Citrate, Dihydrate, USP | 5.220 | 1.566 |
| Citric Acid Anhydrous, USP | 3.393 | 1.018 |
| Disodium Edetate (EDTA) | 1.000 | 1.000 |
| Purified Water, USP | q.s. 1 mL | q.s. 1 mL |

To prepare batches NB538-086 and NB538-087, EDTA was dissolved in purified water using an overhead stirrer. Sucralose, citric acid, and sodium citrate were added to this solution and mixed until a clear solution was obtained. Sodium benzoate was then added to this solution and mixed until a clear solution was obtained. Chlorpromazine hydrochloride was added and mixed until a clear solution was obtained. The solution was then transferred to a volumetric flask and purified water was added q.s. The resulting batches, NB538-086 and NB538-087, and previous batches NB538-060 and NB538-072 were stored under specified conditions and monitored over time to evaluate any decreases in weight, and the results are shown in Table 42 below.

TABLE 42

Decreases in weight of NB538-060, NB538-072, NB538-086 and NB538-087
Decrease in Weight (%)

| Condition | Time Point | | | |
|---|---|---|---|---|
| | 0 Hour | 1 Month | 2 Months | 3 Months |
| Batch NB538-060 (100 mg/ml) | | | | |
| 25° C. ± 2° C./40 ± 5% RH | NA | 0.1 | 0.2 | 0.3 |
| 40° C. ± 2° C./NMT 25% RH | NA | 0.3 | 0.6 | 0.8 |
| Batch NB538-072 (30 mg/ml) | | | | |
| 25° C. ± 2° C./40 ± 5% RH | NA | 0.3 | 0.5 | 0.9 |
| 40° C. ± 2° C./NMT 25% RH | NA | 0.5 | 1.0 | 1.3 |
| Batch NB538-087 (100 mg/ml) | | | | |
| 25° C. ± 2° C./40 ± 5% RH | NA | 0.1 | 0.1 | 0.2 |
| 40° C. ± 2° C./75 ± 5% RH | NA | 0.1 | 0.2 | 0.3 |
| Batch NB538-086 (30 mg/ml) | | | | |
| 25° C. ± 2° C./60 ± 5% RH | NA | 0.1 | 0.2 | 0.3 |
| 40° C. ± 2° C./75 ± 5% RH | NA | 0.2 | 0.4 | 0.5 |
| Acceptance Criteria | NMT 5% | | | |

NMT—Not More Than,
NA—Not Applicable

A relatively higher decrease in weight was seen at 40° C. in comparison to 25° C., irrespective of the storage humidity or product strength. Similarly, relatively higher weight loss was also seen at lower humidity levels for the products of the same batches. Weight loss from all the tested samples was considerably under the limit of 5% after 3 months of storage. The highest decrease in weight (1.3%) among the tested compositions was seen for samples of batch NB538-072 (30 mg/ml) after 3 months of storage at 40° C.±2° C./NMT 25% RH. Under those conditions a weight loss of 2.6% can be expected after 6 months of storage assuming a linear extrapolation of decrease in weight. Since that is well under the limit of 5%, it is unlikely that the product would exhibit water loss above its acceptance criteria over its intended shelf life of 2 years.

The proposed packaging configuration of 120 ml and 240 ml PET bottles for 30 mg/ml and 100 mg/ml chlorpromazine hydrochloride strengths, respectively, with induction seal resulted in a product with weight loss within acceptable limits after 3 months of storage under accelerated conditions. Assuming linear extrapolation it is also expected that it would meet the acceptance criteria after 6 months of storage under accelerated conditions or 24 months of storage under controlled room temperature and humidity conditions.

Example 12

The following study was performed to determine the effectiveness of sodium benzoate as a preservative at its respective concentration in the formulations containing EDTA for oral liquid compositions according to the present disclosure including 100 mg/mL and 30 mg/mL chlorpromazine hydrochloride. Batches with varying concentrations of sodium benzoate were prepared for antimicrobial effectiveness test (AET) evaluation as per USP (United States Pharmacopoeia) Version 42. Although AET was conducted earlier, in order to determine the impact of the presence of EDTA on the microbiological stability of the product, the formulations with EDTA were also evaluated for antimicrobial effectiveness. The concentrations of the preservatives in the drug product were kept identical to those used previously. The compositions of the corresponding formulations are provided below in Table 43.

TABLE 43

Formulation compositions
Formulation Composition for AET Studies

Quantity in mg/mL (Batch Size: 1 Liter)

| | Batch Number | | | | |
|---|---|---|---|---|---|
| (Strength: 100 mg/mL) | NB538-096 | NB538-097 | NB538-098 | NB538-099 | NB538-100 |
| Chlorpromazine Hydrochloride | 100.000 | 100.000 | 100.000 | 100.000 | 100.000 |
| Sucralose, USP | 30.000 | 30.000 | 30.000 | 30.000 | 30.000 |
| Sodium Benzoate, NF | | 0.500 | 1000 | 1.500 | 2.000 |
| Sodium Citrate, Dihydrate, USP | 5.220 | 5.220 | 5.220 | 5.220 | 5.220 |
| Citric Acid Anhydrous, USP | 3.393 | 3.393 | 3.393 | 3.393 | 3.393 |
| Disodium Edetate (EDTA) | 1.000 | 1.000 | 1.000 | 1.000 | 1.000 |
| Purified Water, USP | q.s. to 1 mL | q.s. to 1 mL | q.s. to 1 mL | q.s. to 1 | q.s. to 1 mL |

| | Batch Number | | | | |
|---|---|---|---|---|---|
| (Strength: 30 mg/mL) | NB538-101 | NB538-102 | NB538-103 | NB538-104 | NB538-105 |
| Chlorpromazine Hydrochloride | 30.000 | 30.000 | 30.000 | 30.000 | 30.000 |
| Sucralose, USP | 9.000 | 9.000 | 9.000 | 9.000 | 9.000 |
| Sodium Benzoate, NE | | 0.150 | 0.300 | 0.450 | 0.600 |
| Sodium Citrate, Dihydrate, USP | 1.566 | 1.566 | 1.566 | 1.566 | 1.566 |
| Citric Acid Anhydrous, USP | 1.018 | 1.018 | 1.018 | 1.018 | 1.018 |
| Disodium Edetate (EDTA) | 1.000 | 1.000 | 1.000 | 1.000 | 1.000 |
| Purified Water, USP | q.s. to 1 mL | q.s. to 1 mL | q.s. to 1 mL | q.s. to 1 mL | q.s. to 1 mL |

To prepare batches NB538-096, NB538-097, NB538-098, NB538-099, NB538-100, NB538-101, NB538-102, NB538-103, NB538-104, and NB538-105, sucralose was dissolved in purified water using an overhead stirrer. Citric acid, sodium citrate and sodium benzoate (if applicable) were added to this solution and mixed until a clear solution was obtained. Chlorpromazine hydrochloride was added and mixed until a clear solution was obtained. The solution was then transferred to a volumetric flask and purified water was added q.s. to 1000 mL. Each batch was then assayed to determine the starting concentration of chlorpromazine hydrochloride as shown in Table 44 below, and the efficacy results of the preservative are shown for the batches in Tables 45-54 below.

TABLE 44

Assay of Chlorpromazine Hydrochloride and Sodium Benzoate at Time Zero

| Batch Number | Sodium Benzoate Content (% w/v) | Chlorpromazine Hydrochloride Assay (% Label Claim) |
|---|---|---|
| NB538-096 | 0.000 | 99.9 |
| NB538-097 | 0.049 | 100.5 |
| NB538-098 | 0.096 | 100.4 |
| NB538-099 | 0.146 | 100.6 |
| NB538-100 | 0.199 | 100.4 |
| NB538-101 | 0.000 | 100.7 |
| NB538-102 | 0.017 | 101.0 |
| NB538-103 | 0.032 | 101.0 |
| NB538-104 | 0.043 | 101.6 |
| NB538-105 | 0.059 | 101.6 |

TABLE 45

AET-Efficacy Results for Batch NB538-101 (30 mg/ml); Sodium Benzoate Concentration: 0.00% w/v Description: Chlorpromazine HCl Oral Concentrate 30 mg/mL; AET Batch 1

| Lot # NB538-101 | | S. aureus | | E. coli | | P. aeruginosa | | B. cepacia | |
|---|---|---|---|---|---|---|---|---|---|
| | GBL# 565407/1 | Survivors | $Log_{10}$ reduction | Survivors | $Log_{10}$ reduction | Survivors | $Log_{10}$ reduction | Survivors | $Log_{10}$ reduction |
| Time-0 | cfu/mL $log_{10}$ | $1.1 \times 10^6$ 6.0 | N/A | $4.1 \times 10^5$ 5.6 | N/A | $4.4 \times 10^5$ 5.6 | N/A | $3.9 \times 10^5$ 5.6 | N/A |

TABLE 45-continued

AET-Efficacy Results for Batch NB538-101 (30 mg/ml); Sodium Benzoate Concentration: 0.00% w/v

| | Lot # NB538-101 | | | Description: Chlorpromazine HCl Oral Concentrate 30 mg/mL; AET Batch 1 | | | | | |
|---|---|---|---|---|---|---|---|---|---|
| Specifications | | | | $1 \times 10^5 - 1 \times 10^6$ cfu/mL | | | | | |
| Day-14 | cfu/mL $\log_{10}$ | <100 <2 | ≥4.0 | <100 <2 | ≥3.6 | <100 <2 | ≥3.6 | <100 <2 | ≥3.6 |
| Specifications | | | | ≥1.0 $\log_{10}$ from Time-0 | | | | | |
| Day-28 | cfu/mL $\log_{10}$ | <100 <2 | ≥4.0 | <100 <2 | ≥3.6 | <100 <2 | ≥3.6 | <100 <2 | ≥3.6 |
| Specifications | | | | No increase from Day-14 | | | | | |

| | | | | *C. albicans* | | *A. brasiliensis* | |
|---|---|---|---|---|---|---|---|
| | | GBL# 565407/1 | | Survivors | $\log_{10}$ reduction | Survivors | $\log_{10}$ reduction |
| Time-0 | | cfu/mL $\log_{10}$ | | $1.1 \times 10^5$ 5.0 | N/A | $1.2 \times 10^5$ 5.1 | N/A |
| Specifications | | | | $1 \times 10^5 - 1 \times 10^6$ cfu/mL | | | |
| Day-14 | | cfu/mL $\log_{10}$ | | <100 <2 | ≥3.0 | $2.1 \times 10^4$ 4.3 | 0.8 |
| Specifications | | | | No increase from Time-0 | | | |
| Day-28 | | cfu/mL $\log_{10}$ | | <100 <2 | ≥3.0 | $1.2 \times 10^4$ 4.1 | 1.0 |
| Specifications | | | | No increase from Time-0 | | | |

Legend:
cfu = colony forming units,
N/A = Not Applicable,
Time-0 = Inoculum Recovery,
No increase = in counts is defined as not more than 0.5 $\log_{10}$ unit more than the value to which it is compared.

TABLE 46

AET—Efficacy Results for Batch NB538-102 (30 mg/ml); Sodium Benzoate Concentration: 0.015% w/v Lot # NB538-102 Description: Chlorpromazine HCl Oral Concentrate, 30 mg/mL; AET Batch 2

| | | *S. aureus* | | *E. coli* | | *P. aeruginosa* | | *B. cepacia* | | *C. albicans* | | *A. brasiliensis* | |
|---|---|---|---|---|---|---|---|---|---|---|---|---|---|
| GBL# 565407/2 | | Survivors | $\log_{10}$ reduction | Survivors | $\log_{10}$ reduction | Survivors | $\log_{10}$ reduction | Survivors | $\log_{10}$ reduction | Survivors | $\log_{10}$ reduction | Survivors | $\log_{10}$ reduction |
| Time-0 | cfu/mL $\log_{10}$ | $1.1 \times 10^6$ 6.0 | N/A | $4.1 \times 10^5$ 5.6 | N/A | $4.4 \times 10^5$ 5.6 | N/A | $3.9 \times 10^5$ 5.6 | N/A | $1.1 \times 10^5$ 5.1 | N/A | $1.2 \times 10^5$ 5.1 | N/A |
| Specifications | | | | | | $1 \times 10^5 - 1 \times 10^6$ cfu/mL | | | | | | | |
| Day-14 | cfu/mL $\log_{10}$ | <100 <2 | ≥4.0 | <100 <2 | ≥3.6 | <100 <2 | ≥3.6 | <100 <2 | ≥3.6 | <100 <2 | ≥4.1 | $1.1 \times 10^4$ 4.0 | 0.9 |
| Specifications | | | | ≥1.0 $\log_{10}$ from Time-0 | | | | | | | | No increase from Time-0 | |
| Day-28 | cfu/mL $\log_{10}$ | <100 <2 | ≥4.0 | <100 <2 | ≥3.6 | <100 <2 | ≥3.6 | <100 <2 | ≥3.6 | <100 <2 | ≥4.1 | $9 \times 10^3$ 4.0 | 0.9 |
| Specifications | | | | No increase from Day-14 | | | | | | | | No increase from Time-0 | |

Legend: cfu = colony forming units,
N/A = Not Applicable,
Time-0 = Inoculum Recovery,
No increase = in counts is defined as not more than 0.5$\log_{10}$ unit more than the value to which it is compared.

TABLE 47

AET—Efficacy Results for Batch NB538-103 (30 mg/ml); Sodium Benzoate Concentration: 0.030% w/v Lot # NB538-103 Description: Chlorpromazine HCl Oral Concentrate, 30 mg/mL

| | | *S. aureus* | | *E. coli* | | *P. aeruginosa* | | *B. cepacia* | | *C. albicans* | | *A. brasiliensis* | |
|---|---|---|---|---|---|---|---|---|---|---|---|---|---|
| GBL# 565407/3 | | Survivors | $\log_{10}$ reduction | Survivors | $\log_{10}$ reduction | Survivors | $\log_{10}$ reduction | Survivors | $\log_{10}$ reduction | Survivors | $\log_{10}$ reduction | Survivors | $\log_{10}$ reduction |
| Time-0 | cfu/mL $\log_{10}$ | $1.1 \times 10^6$ 6.0 | N/A | $4.1 \times 10^5$ 5.6 | N/A | $4.4 \times 10^5$ 5.6 | N/A | $3.9 \times 10^5$ 5.6 | N/A | $1.1 \times 10^5$ 5.0 | N/A | $1.2 \times 10^5$ 5.1 | N/A |
| Specifications | | | | | | $1 \times 10^5 - 1 \times 10^6$ cfu/mL | | | | | | | |

TABLE 47-continued

AET—Efficacy Results for Batch NB538-103 (30 mg/ml); Sodium Benzoate Concentration: 0.030% w/v Lot # NB538-103 Description: Chlorpromazine HCl Oral Concentrate, 30 mg/mL

| GBL# 565407/3 | | S. aureus | | E. coli | | P. aeruginosa | | B. cepacia | | C. albicans | | A. brasiliensis | |
|---|---|---|---|---|---|---|---|---|---|---|---|---|---|
| | | Survivors | $\text{Log}_{10}$ reduction | Survivors | $\text{Log}_{10}$ reduction | Survivors | $\text{Log}_{10}$ reduction | Survivors | $\text{Log}_{10}$ reduction | Survivors | $\text{Log}_{10}$ reduction | Survivors | $\text{Log}_{10}$ reduction |
| Day-14 | cfu/mL | <100 | ≥4.0 | <100 | ≥3.6 | <100 | ≥3.6 | <100 | ≥3.6 | <100 | ≥3.0 | $1.2 \times 10^4$ | 0.9 |
| | $\log_{10}$ | <2 | | <2 | | <2 | | <2 | | <2 | | 4.1 | |
| | Specifications | | | ≥1.0 $\log_{10}$ from Time-0 | | | | | | No increase from Time-0 | | | |
| Day-28 | cfu/mL | <100 | ≥4.0 | <100 | ≥3.6 | <100 | ≥3.6 | <100 | ≥3.6 | <100 | ≥3.0 | $1.9 \times 10^3$ | 1.8 |
| | $\log_{10}$ | <2 | | <2 | | <2 | | <2 | | <2 | | 3.3 | |
| | Specifications | | | No increase from Day-14 | | | | | | No increase from Time-0 | | | |

Legend: cfu = colony forming units,
N/A = Not Applicable,
Time-0 = Inoculum Recovery,
No increase = in counts is defined as not more than 0.5$\log_{10}$ unit more than the value to which it is compared.

TABLE 48

AET—Efficacy Results for Batch NB538-104 (30 mg/ml); Sodium Benzoate Concentration: 0.045% w/v Lot # NB538-104 Description: Chlorpromazine HCl Oral Concentrate, 30 mg/mL

| GBL# 565407/4 | | S. aureus | | E. coli | | P. aeruginosa | | B. cepacia | | C. albicans | | A. brasiliensis | |
|---|---|---|---|---|---|---|---|---|---|---|---|---|---|
| | | Survivors | $\text{Log}_{10}$ reduction | Survivors | $\text{Log}_{10}$ reduction | Survivors | $\text{Log}_{10}$ reduction | Survivors | $\text{Log}_{10}$ reduction | Survivors | $\text{Log}_{10}$ reduction | Survivors | $\text{Log}_{10}$ reduction |
| Time-0 | cfu/mL | $1.1 \times 10^6$ | N/A | $4.1 \times 10^5$ | N/A | $4.4 \times 10^5$ | N/A | $3.9 \times 10^5$ | N/A | $1.1 \times 10^5$ | N/A | $1.2 \times 10^5$ | N/A |
| | $\log_{10}$ | 6.0 | | 5.6 | | 5.6 | | 5.6 | | 5.0 | | 5.1 | |
| | Specifications | | | | | $1 \times 10^5$-$1 \times 10^6$ cfu/mL | | | | | | | |
| Day-14 | cfu/mL | <100 | ≥4.0 | <100 | ≥3.6 | <100 | ≥3.6 | <100 | ≥3.6 | <100 | ≥3.0 | $1.3 \times 10^4$ | 1.0 |
| | $\log_{10}$ | <2 | | <2 | | <2 | | <2 | | <2 | | 4.1 | |
| | Specifications | | | ≥1.0 $\log_{10}$ from Time-0 | | | | | | No increase from Time-0 | | | |
| Day-28 | cfu/mL | <100 | ≥4.0 | <100 | ≥3.6 | <100 | ≥3.6 | <100 | ≥3.6 | <100 | ≥3.0 | $2.8 \times 10^3$ | 1.7 |
| | $\log_{10}$ | <2 | | <2 | | <2 | | <2 | | <2 | | 3.4 | |
| | Specifications | | | No increase from Day-14 | | | | | | No increase from Time-0 | | | |

Legend: cfu = colony forming units,
N/A = Not Applicable,
Time-0 = Inoculum Recovery,
No increase = in counts is defined as not more than 0.5$\log_{10}$ unit more than the value to which it is compared.

TABLE 49

AET—Efficacy Results for Batch NB538-105 (30 mg/ml); Sodium Benzoate Concentration: 0.060% w/v Lot # NB538-105 Description: Chlorpromazine HCl Oral Concentrate, 30 mg/mL

| GBL# 565407/5 | | S. aureus | | E. coli | | P. aeruginosa | | B. cepacia | | C. albicans | | A. brasiliensis | |
|---|---|---|---|---|---|---|---|---|---|---|---|---|---|
| | | Survivors | $\text{Log}_{10}$ reduction | Survivors | $\text{Log}_{10}$ reduction | Survivors | $\text{Log}_{10}$ reduction | Survivors | $\text{Log}_{10}$ reduction | Survivors | $\text{Log}_{10}$ reduction | Survivors | $\text{Log}_{10}$ reduction |
| Time-0 | cfu/mL | $1.1 \times 10^6$ | N/A | $4.1 \times 10^5$ | N/A | $4.4 \times 10^5$ | N/A | $5.1 \times 10^5$ | N/A | $1.1 \times 10^5$ | N/A | $1.2 \times 10^5$ | N/A |
| | $\log_{10}$ | 6.0 | | 5.6 | | 5.6 | | 5.7 | | 5.0 | | 5.1 | |
| | Specifications | | | | | $1 \times 10^5$-$1 \times 10^6$ cfu/mL | | | | | | | |
| Day-14 | cfu/mL | <100 | ≥4.0 | <100 | ≥3.6 | <100 | ≥3.6 | <100 | ≥4.7 | <100 | ≥3.0 | $1.2 \times 10^4$ | 1.9 |
| | $\log_{10}$ | <2 | | <2 | | <2 | | <2 | | <2 | | 4.1 | |
| | Specifications | | | ≥1.0 $\log_{10}$ from Time-0 | | | | | | No increase from Time-0 | | | |
| Day-28 | cfu/mL | <100 | ≥4.0 | <100 | ≥3.6 | <100 | ≥3.6 | <100 | ≥4.7 | <100 | ≥3.0 | $1.5 \times 10^3$ | ≥1.9 |
| | $\log_{10}$ | <2 | | <2 | | <2 | | <2 | | <2 | | 3.2 | |
| | Specifications | | | No increase from Day-14 | | | | | | No increase from Time-0 | | | |

Legend: cfu = colony forming units,
N/A = Not Applicable,
Time-0 = Inoculum Recovery,
No increase = in counts is defined as not more than 0.5$\log_{10}$ unit more than the value to which it is compared.

TABLE 50

AET—Efficacy Results for Batch NB538-096 (100 mg/ml); Sodium Benzoate Concentration: 0.00% w/v Lot # NB538-096 Description: Chlorpromazine HCl Oral Concentrate, 100 mg/mL

| GBL# 565408/1 | | S. aureus | | E. coli | | P. aeruginosa | | B. cepacia | | C. albicans | | A. brasiliensis | |
|---|---|---|---|---|---|---|---|---|---|---|---|---|---|
| | | Survivors | Log$_{10}$ reduction | Survivors | Log$_{10}$ reduction | Survivors | Log$_{10}$ reduction | Survivors | Log$_{10}$ reduction | Survivors | Log$_{10}$ reduction | Survivors | Log$_{10}$ reduction |
| Time-0 | cfu/mL | $1.1 \times 10^6$ | N/A | $4.1 \times 10^5$ | N/A | $4.4 \times 10^5$ | N/A | $3.9 \times 10^5$ | N/A | $1.1 \times 10^5$ | N/A | $1.2 \times 10^5$ | N/A |
| | log$_{10}$ | 6.0 | | 5.6 | | 5.6 | | 5.6 | | 5.0 | | 5.1 | |
| | Specifications | | | | | $1 \times 10^5$-$1 \times 10^6$ cfu/mL | | | | | | | | |
| Day-14 | cfu/mL | <100 | ≥4.0 | <100 | ≥3.6 | <100 | ≥3.6 | <100 | ≥3.6 | <100 | ≥3.0 | $1.1 \times 10^4$ | 1.1 |
| | log$_{10}$ | <2 | | <2 | | <2 | | <2 | | <2 | | 4.0 | |
| | Specifications | | | ≥1.0 log$_{10}$ from Time-0 | | | | | | No increase from Time-0 | | | | |
| Day-28 | cfu/mL | <100 | ≥4.0 | <100 | ≥3.6 | <100 | ≥3.6 | <100 | ≥3.6 | <100 | ≥3.0 | $2.5 \times 10^3$ | 1.7 |
| | log$_{10}$ | <2 | | <2 | | <2 | | <2 | | <2 | | 3.4 | |
| | Specifications | | | No increase from Day-14 | | | | | | No increase from Time-0 | | | | |

Legend: cfu = colony forming units,
N/A = Not Applicable,
Time-0 = Inoculum Recovery,
No increase = in counts is defined as not more than 0.5log$_{10}$ unit more than the value to which it is compared.

TABLE 51

AET—Efficacy Results for Batch NB538-097 (100 mg/ml); Sodium Benzoate Concentration: 0.050% w/v Lot # NB538-097 Description: Chlorpromazine HCl Oral Concentrate, 100 mg/mL

| GBL# 565408/2 | | S. aureus | | E. coli | | P. aeruginosa | | B. cepacia | | C. albicans | | A. brasiliensis | |
|---|---|---|---|---|---|---|---|---|---|---|---|---|---|
| | | Survivors | Log$_{10}$ reduction | Survivors | Log$_{10}$ reduction | Survivors | Log$_{10}$ reduction | Survivors | Log$_{10}$ reduction | Survivors | Log$_{10}$ reduction | Survivors | Log$_{10}$ reduction |
| Time-0 | cfu/mL | $1.1 \times 10^6$ | N/A | $4.1 \times 10^5$ | N/A | $4.4 \times 10^5$ | N/A | $3.9 \times 10^5$ | N/A | $1.1 \times 10^5$ | N/A | $1.2 \times 10^5$ | N/A |
| | log$_{10}$ | 6.0 | | 5.6 | | 5.6 | | 5.6 | | 5.1 | | 5.1 | |
| | Specifications | | | | | $1 \times 10^5$-$1 \times 10^6$ cfu/mL | | | | | | | | |
| Day-14 | cfu/mL | <100 | ≥4.0 | <100 | ≥3.6 | <100 | ≥3.6 | <100 | ≥3.6 | <100 | ≥4.1 | $2.1 \times 10^4$ | 0.8 |
| | log$_{10}$ | <2 | | <2 | | <2 | | <2 | | <2 | | 4.3 | |
| | Specifications | | | ≥1.0 log$_{10}$ from Time-0 | | | | | | No increase from Time-0 | | | | |
| Day-28 | cfu/mL | <100 | ≥4.0 | <100 | ≥3.6 | <100 | ≥3.6 | <100 | ≥3.6 | <100 | ≥4.1 | $2.0 \times 10^3$ | 1.8 |
| | log$_{10}$ | <2 | | <2 | | <2 | | <2 | | <2 | | 3.3 | |
| | Specifications | | | No increase from Day-14 | | | | | | No increase from Time-0 | | | | |

Legend: cfu = colony forming units,
N/A = Not Applicable,
Time-0 = Inoculum Recovery,
No increase = in counts is defined as not more than 0.5log$_{10}$ unit more than the value to which it is compared.

TABLE 52

AET—Efficacy Results for Batch NB538-098 (100 mg/ml); Sodium Benzoate Concentration: 0.100% w/v Lot # NB538-098 Description: Chlorpromazine HCl Oral Concentrate, 100 mg/mL

| GBL# 565408/3 | | S. aureus | | E. coli | | P. aeruginosa | | B. cepacia | | C. albicans | | A. brasiliensis | |
|---|---|---|---|---|---|---|---|---|---|---|---|---|---|
| | | Survivors | Log$_{10}$ reduction | Survivors | Log$_{10}$ reduction | Survivors | Log$_{10}$ reduction | Survivors | Log$_{10}$ reduction | Survivors | Log$_{10}$ reduction | Survivors | Log$_{10}$ reduction |
| Time-0 | cfu/mL | $1.1 \times 10^6$ | N/A | $4.1 \times 10^5$ | N/A | $4.4 \times 10^5$ | N/A | $3.9 \times 10^5$ | N/A | $1.1 \times 10^5$ | N/A | $1.2 \times 10^5$ | N/A |
| | log$_{10}$ | 6.0 | | 5.6 | | 5.6 | | 5.6 | | 5.0 | | 5.1 | |
| | Specifications | | | | | $1 \times 10^5$-$1 \times 10^6$ cfu/mL | | | | | | | | |
| Day-14 | cfu/mL | <100 | ≥4.0 | <100 | ≥3.6 | <100 | ≥3.6 | <100 | ≥3.6 | <100 | ≥3.0 | $1.9 \times 10^4$ | 0.8 |
| | log$_{10}$ | <2 | | <2 | | <2 | | <2 | | <2 | | 4.3 | |
| | Specifications | | | ≥1.0 log$_{10}$ from Time-0 | | | | | | No increase from Time-0 | | | | |

TABLE 52-continued

AET—Efficacy Results for Batch NB538-098 (100 mg/ml); Sodium Benzoate Concentration: 0.100% w/v Lot # NB538-098 Description: Chlorpromazine HCl Oral Concentrate, 100 mg/mL

| GBL# 565408/3 | | S. aureus | | E. coli | | P. aeruginosa | | B. cepacia | | C. albicans | | A. brasiliensis | |
|---|---|---|---|---|---|---|---|---|---|---|---|---|---|
| | | Survivors | Log$_{10}$ reduction | Survivors | Log$_{10}$ reduction | Survivors | Log$_{10}$ reduction | Survivors | Log$_{10}$ reduction | Survivors | Log$_{10}$ reduction | Survivors | Log$_{10}$ reduction |
| Day-28 | cfu/mL | <100 | ≥4.0 | <100 | ≥3.6 | <100 | ≥3.6 | <100 | ≥3.6 | <100 | ≥3.0 | 1.8 × 10$^3$ | 1.8 |
| | log$_{10}$ | <2 | | <2 | | <2 | | <2 | | <2 | | 3.3 | |
| Specifications | | | | No increase from Day-14 | | | | | | No increase from Time-0 | | | |

Legend: cfu = colony forming units,
N/A = Not Applicable,
Time-0 = Inoculum Recovery,
No increase = in counts is defined as not more than 0.5log$_{10}$ unit more than the value to which it is compared.

TABLE 53

AET—Efficacy Results for Batch NB538-099 (100 mg/ml); Sodium Benzoate Concentration: 0.150% w/v Lot # NB538-099 Description: Chlorpromazine HCl Oral Concentrate, 100 mg/mL

| GBL# 565408/4 | | S. aureus | | E. coli | | P. aeruginosa | | B. cepacia | | C. albicans | | A. brasiliensis | |
|---|---|---|---|---|---|---|---|---|---|---|---|---|---|
| | | Survivors | Log$_{10}$ reduction | Survivors | Log$_{10}$ reduction | Survivors | Log$_{10}$ reduction | Survivors | Log$_{10}$ reduction | Survivors | Log$_{10}$ reduction | Survivors | Log$_{10}$ reduction |
| Time-0 | cfu/mL | 1.1 × 10$^6$ | N/A | 4.1 × 10$^5$ | N/A | 4.4 × 10$^5$ | N/A | 3.9 × 10$^5$ | N/A | 1.1 × 10$^5$ | N/A | 1.2 × 10$^5$ | N/A |
| | log$_{10}$ | 6.0 | | 5.6 | | 5.6 | | 5.6 | | 5.0 | | 5.1 | |
| Specifications | | | | | | 1 × 10$^5$-1 × 10$^6$ cfu/mL | | | | | | | | |
| Day-14 | cfu/mL | <100 | ≥4.0 | <100 | ≥3.6 | <100 | ≥3.6 | <100 | ≥3.6 | <100 | ≥3.0 | 1.1 × 10$^4$ | 1.1 |
| | log$_{10}$ | <2 | | <2 | | <2 | | <2 | | <2 | | 4.0 | |
| Specifications | | | | ≥1.0 log$_{10}$ from Time-0 | | | | | | No increase from Time-0 | | | |
| Day-28 | cfu/mL | <100 | ≥4.0 | <100 | ≥3.6 | <100 | ≥3.6 | <100 | ≥3.6 | <100 | ≥3.0 | 2.0 × 10$^3$ | 1.8 |
| | log$_{10}$ | <2 | | <2 | | <2 | | <2 | | <2 | | 3.3 | |
| Specifications | | | | No increase from Day-14 | | | | | | No increase from Time-0 | | | |

Legend: cfu = colony forming units,
N/A = Not Applicable,
Time-0 = Inoculum Recovery,
No increase = in counts is defined as not more than 0.5log$_{10}$ unit more than the value to which it is compared.

TABLE 54

AET—Efficacy Results for Batch NB538-100 (100 mg/ml); Sodium Benzoate Concentration: 0.200% w/v Lot # NB538-100 Description: Chlorpromazine HCl Oral Concentrate, 100 mg/mL

| GBL# 565408/5 | | S. aureus | | E. coli | | P. aeruginosa | | B. cepacia | | C. albicans | | A. brasiliensis | |
|---|---|---|---|---|---|---|---|---|---|---|---|---|---|
| | | Survivors | Log$_{10}$ reduction | Survivors | Log$_{10}$ reduction | Survivors | Log$_{10}$ reduction | Survivors | Log$_{10}$ reduction | Survivors | Log$_{10}$ reduction | Survivors | Log$_{10}$ reduction |
| Time-0 | cfu/mL | 1.1 × 10$^6$ | N/A | 4.1 × 10$^5$ | N/A | 4.4 × 10$^5$ | N/A | 5.1 × 10$^5$ | N/A | 1.1 × 10$^5$ | N/A | 1.2 × 10$^5$ | N/A |
| | log$_{10}$ | 6.0 | | 5.6 | | 5.6 | | 5.7 | | 5.0 | | 5.1 | |
| Specifications | | | | | | 1 × 10$^5$-1 × 10$^6$ cfu/mL | | | | | | | | |
| Day-14 | cfu/mL | <100 | ≥4.0 | <100 | ≥3.6 | <100 | ≥3.6 | <100 | ≥4.7 | <100 | ≥3.0 | 1.4 × 10$^4$ | 1.0 |
| | log$_{10}$ | <2 | | <2 | | <2 | | <2 | | <2 | | 4.1 | |
| Specifications | | | | ≥1.0 log$_{10}$ from Time-0 | | | | | | No increase from Time-0 | | | |
| Day-28 | cfu/mL | <100 | ≥4.0 | <100 | ≥3.6 | <100 | ≥3.6 | <100 | ≥4.7 | <100 | ≥3.0 | 1.1 × 10$^3$ | 2.1 |
| | log$_{10}$ | <2 | | <2 | | <2 | | <2 | | <2 | | 3.0 | |
| Specifications | | | | No increase from Day-14 | | | | | | No increase from Time-14 | | | |

Legend: cfu = colony forming units,
N/A = Not Applicable,
Time-0 = Inoculum Recovery,
No increase = in counts is defined as not more than 0.5log$_{10}$ unit more than the value to which it is compared.

As seen in earlier examples in formulations without EDTA, AET results with EDTA in the formulation showed that all the compositions tested in this study for both 100 mg/ml and 30 mg/ml chlorpromazine hydrochloride met the acceptance criteria for category 3 products. The inherent antimicrobial effectiveness of the product, which may be due to the chlorpromazine hydrochloride, is demonstrated by formulations NB538-096 and NB538-101, which passed the AET even in the absence of sodium benzoate.

The concentration of sodium benzoate in the final formulation was kept at 0.030% and 0.100% w/v for the compositions including 30 mg/ml and 100 mg/ml chlorpromazine hydrochloride, respectively. These concentrations were conservatively set to ensure the finished product stability as it was packaged in a multi-use container.

Example 13

The following study was performed to determine the impact of headspace nitrogen purging (dissolved oxygen level) and freeze-thaw cycles on the stability of oral liquid compositions according to the present disclosure comprising 100 mg/mL and 30 mg/mL chlorpromazine hydrochloride.

In part A) of the study the impact of nitrogen purging the headspace of the filled primary packaging containers prior to sealing was evaluated throughout the development process. Batches NB538-106 and NB538-107 were manufactured to include 100 mg/ml and 30 mg/ml chlorpromazine hydrochloride, respectively. During packaging, the headspace of the filled bottles was purged with nitrogen to achieve the desired level of dissolved oxygen content and evaluate impact on stability. Nitrogen purging allows diffusion of the oxygen dissolved in the product towards the headspace as well as further displacement of oxygen from the headspace to minimize its fraction in the headspace prior to sealing. Dissolved oxygen levels in the bottles that were not purged with nitrogen were used as baseline levels, and arbitrary levels of <4.5 mg/L and <2 mg/L were selected for further study. These levels were achieved by adjusting the duration of nitrogen purging. The dissolved oxygen content was measured by a galvanic dissolved oxygen probe. The filled bottles were kept under accelerated stability conditions and analyzed to determine the impact of dissolved oxygen on the stability of the product.

In part B) of this study, freeze-thaw studies were conducted to evaluate the impact of the presence of EDTA on the physical and chemical stability of the product upon being thawed after it is subject to low temperature/freezing conditions. Formulations NB538-107 (30 mg/mL chlorpromazine hydrochloride) and NB538-106 (100 mg/mL) were manufactured and evaluated. The formulations for strengths 30 mg/mL and 100 mg/ml were packaged in 240 cc and 120 cc PET bottles, respectively. The headspace of each bottle was purged with nitrogen prior to sealing. The bottles were stored between −10 to −20° C. or 2-8° C. for 2 days per cycle and then thawed at 25° C./60% RH or 40° C./75% RH for 2 days per cycle. The bottles were inspected visually for phase separation and appearance and analyzed for assay, sodium benzoate content, pH, EDTA content, impurities, and appearance after 3 freeze cycles and thaw cycles each. The formulation compositions of batches NB538-106 and ND538-107 are shown in Table 55 below.

TABLE 55

Formulation compositions
Formulation Composition
Quantity in mg/mL; Batch Size: 5 L (30 mg/ml), 10 L (100 mg/ml)

| Ingredients | NB538-106 (100 mg/ml) | NB538-107 (30 mg/ml) |
|---|---|---|
| Chlorpromazine Hydrochloride | 100.000 | 30.000 |
| Sucralose, USP | 30.000 | 9.000 |
| Sodium Benzoate, NF | 1.000 | 0.300 |
| Sodium Citrate, Dihydrate, USP | 5.220 | 1.566 |
| Citric Acid Anhydrous, USP | 3.393 | 1.018 |
| Disodium Edetate (EDTA) | 1.000 | 1.000 |
| Purified Water, USP | 898.387 | 968.116 |
| Density | 1.039 g/mL | 1.011 g/mL |

To prepare batches NB538-106 and NB538-107, sucralose, EDTA, sodium benzoate, citric acid, and sodium citrate were added to purified water and mixed using an overhead stirrer until a clear solution was obtained. Chlorpromazine hydrochloride was added and mixed until a clear solution was obtained. The resulting batches were then packaged and monitored over time under certain conditions to determine the stability of the solutions. The packaging particulars, storage conditions, and results are shown in Table 56 below.

TABLE 56

A) Impact of dissolved oxygen level on stability

| Sampling Time Point | Condition | Dissolved Oxygen Level* | Appearance | pH | Assay (%) | EDTA Content (% w/v) | Sodium Benzoate (% w/v) | Impurities (%) A | UD | Total |
|---|---|---|---|---|---|---|---|---|---|---|
| Batch # NB538-106 (100 mg/mL) | | | | | | | | | | |
| Packaging | | Bottle Configuration: 240 cc PET; All bottles were induction sealed | | | | | | | | |
| 0 Hour | NA | 9.49 | Clear liquid | 3.8 | 100.7 | 0.098 | 0.101 | ≤0.05 | ≤0.05 | ≤0.05 |
| 7 Days | 60° C. | Not purged with nitrogen | Clear liquid | 3.8 | 101.2 | 0.071 | 0.105 | 0.15 | ≤0.05 | 0.15 |
| 15 Days | 60° C. | | Clear liquid | 3.9 | 101.5 | 0.057 | 0.101 | 0.21 | ≤0.05 | 0.21 |
| 7 Days | 60° C. | <2 mg/L | Clear liquid | 3.8 | 101.1 | 0.088 | 0.101 | 0.07 | ≤0.05 | 0.07 |
| 15 Days | 60° C. | | Clear liquid | 3.8 | 102.9 | 0.088 | 0.098 | 0.08 | ≤0.05 | 0.08 |
| 7 Days | 60° C. | <4.5 mg/L | Clear liquid | 3.8 | 101.2 | 0.090 | 0.102 | 0.07 | ≤0.05 | 0.07 |
| 15 Days | 60° C. | | Clear liquid | 3.8 | 101.2 | 0.089 | 0.102 | 0.08 | ≤0.05 | 0.08 |

TABLE 56-continued

A) Impact of dissolved oxygen level on stability

| Sampling Time Point | Condition | Dissolved Oxygen Level* | Appearance | pH | Assay (%) | EDTA Content (% w/v) | Sodium Benzoate (% w/v) | Impurities (%) A | UD | Total |
|---|---|---|---|---|---|---|---|---|---|---|
| Batch # NB538-107 (30 mg/mL) | | | | | | | | | | |
| Packaging | | Bottle Configuration: 120 cc PET; All bottles were induction sealed | | | | | | | | |
| 0 Hour | NA | 8.22 | Clear liquid | 3.8 | 101.2 | 0.098 | 0.030 | ≤0.05 | ≤0.05 | ≤0.05 |
| 7 Days | 60° C. | Not purged with nitrogen | Clear liquid | 4.0 | 101.5 | 0.063 | 0.030 | 0.52 | ≤0.05 | 0.52 |
| 15 Days | 60° C. | | Clear liquid | 4.1 | 102.1 | 0.040 | 0.031 | 0.71 | ≤0.05 | 0.71 |
| 7 Days | 60° C. | <2 mg/L | Clear liquid | 3.9 | 101.9 | 0.087 | 0.030 | 0.23 | ≤0.05 | 0.23 |
| 15 Days | 60° C. | | Clear liquid | 3.9 | 103.2 | 0.079 | 0.030 | 0.32 | ≤0.05 | 0.32 |
| 7 Days | 60° C. | <4.5 mg/L | Clear liquid | 4.0 | 102.2 | 0.066 | 0.030 | 0.46 | ≤0.05 | 0.46 |
| 15 Days | 60° C. | | Clear liquid | 3.9 | 102.3 | 0.076 | 0.030 | 0.36 | ≤0.05 | 0.36 |
| Acceptance Criteria | Appearance | Clear liquid (no discoloration) | | | | | | | | |
| | pH | 2.0-5.0 | | | | | | | | |
| | Assay | 90.0%-110.0% | | | | | | | | |
| | Impurities | Impurity A NMT 5.0%, Any Unidentified Impurity: NMT 0.10%; Total Impurities: NMT 7.0% | | | | | | | | |
| | EDTA Content | 0.050 to 0.150% w/v at Time Zero; 0.010 to 0.150% w/v for stability samples | | | | | | | | |
| | Sodium benzoate | 0.015-0.045% w/v (30 mg/ml); 0.050 to 0.150% w/v (100 mg/ml) | | | | | | | | |

UD—Unidentified,
ND—Not Detected,
NMT—Not More Than,
NA—Not Available
*Dissolved oxygen level measured only at time zero The studies showed that the pH, assay, and sodium benzoate content of the product remained unaffected by nitrogen purging, irrespective of the chlorpromazine hydrochloride strength or dissolved oxygen level. Also, the appearance of the product did not change as precipitation or discoloration of the product was not seen after storage. However, the impurities and the EDTA content were considerably affected by nitrogen purging. The level of dissolved oxygen, i.e., less than 2.5 mg/L or less than 4 mg/L, did not seem to have an impact on the impurities or the EDTA content; however, the samples from the containers that were not purged with nitrogen showed considerably lower levels of EDTA and higher levels of impurities. After 15 days of storage at 60° C. the container that was not purged with nitrogen retained 0.057% w/v (approx. 57% of label claim ("LC")) EDTA and exhibited 0.21% impurity A, while the container with less than 4.5 mg/L dissolved oxygen retained 0.089% w/v (approx. 89% LC) EDTA and exhibited 0.08% impurity A, respectively, for the 100 mg/ml strength. Similarly, for the 30 mg/ml strength, after 15 days of storage at 60° C. the container that was not purged with nitrogen exhibited 0.040% w/v (approx. 40% LC) EDTA and 0.71% impurity A, while the container with less than 4.5 mg/L dissolved oxygen retained 0.076% w/v (approx. 76% LC) EDTA and exhibited 0.36% impurity A, respectively. In general, the impurity levels for the product including 30 mg/mL chlorpromazine hydrochloride were relatively higher than the product with 100 mg/ml strength. Since the concentration of EDTA in composition of both strengths is identical, i.e., 1 mg/ml, lower EDTA levels upon storage under accelerated conditions for the 30 mg/ml strength composition demonstrate the functionality of EDTA as a chelating agent and its effectiveness in minimizing oxidation, since the drug substance assay values remained unaffected during storage.

Batches NB538-106 and NB538-107 were also evaluated under freeze-thaw cycling, and the packaging particulars, storage conditions, and results are shown in Table 57 below.

TABLE 57

B) Impact of freeze-thaw cycles on stability

| Sampling Time Point | Condition | pH | Appearance | Assay (%) | EDTA Content (% LC) | Sodium Benzoate Content (% LC) | Impurities (%) A | UD | Total |
|---|---|---|---|---|---|---|---|---|---|
| Batch # NB538-106 (100 mg/mL) | | | | | | | | | |
| Packaging | | Bottle Capacity: 240 cc PET; Bottles were purged with nitrogen and induction sealed | | | | | | | |
| After 3 Cycles | Freeze: −10 to −20° C., Thaw: 40° C./75% RH | 4.0 | Clear liquid, Light yellow | 100.1 | 94.0 | 104.9 | <0.05 | <0.05 | <0.05 |
| | Freeze: −10 to −20° C. Thaw: 25° C./60% RH | 4.0 | Clear liquid, Light yellow | 99.9 | 98.4 | 97.7 | <0.05 | <0.05 | <0.05 |

TABLE 57-continued

B) Impact of freeze-thaw cycles on stability

| Sampling Time Point | Condition | pH | Appearance | Assay (%) | EDTA Content (% LC) | Sodium Benzoate Content (% LC) | Impurities (%) | | |
|---|---|---|---|---|---|---|---|---|---|
| | | | | | | | A | UD | Total |
| | Freeze: 2 to 8° C., Thaw: 40° C./75% RH | 4.0 | Clear liquid, Light yellow | 99.6 | 92.1 | 99.8 | 0.06 | <0.05 | 0.06 |
| | Freeze: 2 to 8° C. Thaw: 25° C./60% RH | 3.9 | Clear liquid, Light yellow | 99.4 | 98.2 | 97.2 | <0.05 | <0.05 | <0.05 |
| | | | Batch # NB538-107 (30 mg/mL) | | | | | | |
| Packaging | | | Bottle Capacity: 120 cc PET; Bottles were purged with nitrogen and induction sealed | | | | | | |
| After 3 Cycles | Freeze: −10 to−20° C., Thaw: 40° C./75% RH | 4.0 | Clear liquid, Light yellow | 98.8 | 93.5 | 99.4 | 0.13 | <0.05 | 0.13 |
| | Freeze: −10 to −20° C. Thaw: 2° C./60% RH | 3.9 | Clear liquid, Light yellow | 100.2 | 98.6 | 95.5 | <0.05 | <0.05 | <0.05 |
| | Freeze: 2 to 8° C. Thaw: 40° C./75% RH | 4.1 | Clear liquid, Light yellow | 99.3 | 92.3 | 100.3 | 0.15 | <0.05 | 0.15 |
| | Freeze: 2 to 8° C., Thaw: 25° C./60% RH | 4.0 | Clear liquid, Light yellow | 97.8 | 96.7 | 98.7 | <0.05 | <0.05 | <0.05 |
| Acceptance Criteria | Appearance | | Clear liquid (no discoloration or precipitation) | | | | | | |
| | pH | | 2.0-5.0 | | | | | | |
| | Assay | | 90.0%-110.0% | | | | | | |
| | impurities | | Impurity A NMT 5.0%, Any Unidentified Impurity: NMT 0.10%; Total Impurities: NMT 7.0% | | | | | | |
| | EDTA Content | | 10 to 150% of LC | | | | | | |
| | Sodium benzoate | | 50 to 150% of LC | | | | | | |

UD—Unidentified,
ND—Not Detected,
NMT—Not More Than,
NA—Not Available;
LC—Label claim The methodology for the freeze-thaw experiment for the current study was identical to the one used in Example 9. However, unlike the assay results seen in Example 9, formulations NB538-106 and NB538-107 showed a negligible decrease in the assay values, as nearly 100% drug was retained irrespective of the strength or the freeze-thaw condition. Moreover, the samples retained their appearance, i.e., color and clarity, as no discoloration or precipitation was observed for either of the strengths. The assay and appearance results demonstrated the effectiveness of EDTA in minimizing oxidative degradation of the product during storage. The results for pH and sodium benzoate levels remained unaffected for the samples subject to the freeze-thaw cycles. The EDTA contents were relatively lower for samples thawed at 40° C./75% RH; however, they were still above 90%, indicating that the products should be able to sustain their stability even upon subjection to multiple freeze-thaw cycles. Since the samples were transferred to a glass container for visual evaluation after every cycle, except if the samples were frozen, they were extensively exposed to atmospheric oxygen and, therefore, represent a worst case scenario for the freeze-thaw studies on the product. Under normal circumstances, i.e., in sealed bottles, the EDTA content or impurity may remain unaffected even after multiple freeze-thaw cycles.

The dissolved oxygen studies demonstrated that the level of impurities is higher and EDTA content is considerably lower for samples taken from the containers in which the headspace was not purged with nitrogen prior to sealing. Since EDTA is important for prevention of oxidation and potential discoloration, the product should be purged with nitrogen to minimize its degradation during storage. The freeze-thaw studies demonstrate that the compositions exhibit acceptable physical as well as chemical stability upon exposure to extreme temperatures.

Example 14

The following study was performed to determine the impact of multiple dose withdrawals over a period of 3 months (in-use studies) on the stability of oral liquid compositions according to the present disclosure comprising 100 mg/mL and 30 mg/mL chlorpromazine hydrochloride. In order to determine the impact of multiple withdrawals of doses over a period of 3 months on the stability of the product, i.e., to mimic product handling by the consumer, 0.1 ml doses of solution were withdrawn from the finished product containers of batches NB538-110 and NB538-111 q.i.d. for up to 3 months. The studies were initiated by opening a sealed container and periodically withdrawing from the unsealed container, without additional nitrogen purging, while being stored at room temperature and humidity. The product was analyzed after consistent sample withdrawals for 3 months for the 100 mg/ml chlorpromazine hydrochloride strength and for 2 months for the 30 mg/ml chlorpromazine hydrochloride strength. Sealed samples stored under identical temperature and humidity conditions were used as controls for the unsealed containers subject to in-use studies. The formulation compositions of batches NB538-110 and NB538-111 are shown in Table 58 below.

TABLE 58

Formulation Compositions
Formulation Composition
Quantity in mg/mL; Batch Size: 5 L (30 mg/ml), 10 L (100 mg/ml)

| Ingredients | NB538-110 (30 mg/ml) | NB538-111 (100 mg/ml) |
|---|---|---|
| Chlorpromazine Hydrochloride | 30.000 | 100.000 |
| Sucralose, USP | 9.000 | 30.000 |
| Sodium Benzoate, NF | 0.300 | 1.000 |
| Sodium Citrate, Dihydrate, USP | 1.566 | 5.220 |
| Citric Acid Anhydrous, USP | 1.018 | 3.393 |
| Disodium Edetate (EDTA) | 1.000 | 1.000 |
| Purified Water, USP | 968.116 | 898.387 |
| Density | 1.011 g/mL | 1.039 g/mL |

To prepare batches NB538-110 and NB538-111, sucralose, EDTA, sodium benzoate, citric acid and sodium citrate were added to purified water and mixed using an overhead stirrer until a clear solution was obtained. Chlorpromazine hydrochloride was added and mixed until a clear solution was obtained. The resulting batches were monitored over time to evaluate solution stability. The packaging particulars, storage conditions, and results are shown in Table 59 below.

TABLE 59

Observations for batches NB538-110 and N8538-111

| Sampling Time Point | Sample Type | Storage Condition | Appearance | pH | Assay (%) | EDTA Content (% w/v) | Sodium Benzoate (% w/v) | Impurities (%) A | UD | Total |
|---|---|---|---|---|---|---|---|---|---|---|
| \multicolumn{11}{c}{Batch # NB538-110 (30 mg/mL)} |
| \multicolumn{11}{c}{Packaging: Bottle Configuration: 120 cc PET; All bottles were induction sealed} |
| 0 Hour | NA | NA | Clear liquid | 3.9 | 98.4 | 0.097 | 0.029 | ≤0.05 | ≤0.05 | ≤0.05 |
| 1 Month | Control | Room | Clear liquid | 4.0 | 99.1 | 0.098 | 0.030 | ≤0.05 | ≤0.05 | ≤0.05 |
| 1 Month | Sample | Temperature | Clear liquid | 4.0 | 99.3 | 0.098 | 0.030 | 0.06 | ≤0.05 | 0.06 |
| 2 Months | Control | and | Clear liquid | 4.0 | 99.9 | 0.096 | 0.030 | 0.10 | ≤0.05 | 0.10 |
| 2 Months | Sample | Humidity | Clear liquid | 4.0 | 99.2 | 0.096 | 0.030 | 0.08 | ≤0.05 | 0.08 |
| \multicolumn{11}{c}{Batch # N95384 11 (100 mg/mL)} |
| \multicolumn{11}{c}{Packaging: Bottle Configuration: 240 cc PET; All bottles were induction sealed} |
| 0 Hour | NA | NA | Clear liquid | 4.0 | 98.9 | 0.097 | 0.099 | ≤0.05 | ≤0.05 | ≤0.05 |
| 1 Month | Control | Room | Clear liquid | 4.0 | 99.5 | 0.098 | 0.099 | ≤0.05 | ≤0.05 | ≤0.05 |
| 1 Month | Sample | Temperature | Clear liquid | 4.0 | 99.2 | 0.098 | 0.100 | ≤0.05 | ≤0.05 | ≤0.05 |
| 2 Months | Control | and | Clear liquid | 4.0 | 99.2 | 0.095 | 0.101 | ≤0.05 | ≤0.05 | ≤0.05 |
| 2 Months | Sample | Humidity | Clear liquid | 4.0 | 99.1 | 0.097 | 0.101 | ≤0.05 | ≤0.05 | ≤0.05 |
| 3 Months | Control | | Clear liquid | 4.0 | 100.1 | 0.104 | 0.103 | ≤0.05 | ≤0.05 | ≤0.05 |
| 3 Months | Sample | | Clear liquid | 3.9 | 100.3 | 0.103 | 0.100 | ≤0.05 | ≤0.05 | ≤0.05 |

| Acceptance Criteria | | |
|---|---|---|
| | Appearance | Clear liquid (no discoloration) |
| | pH | 2.0 -5.0 |
| | Assay | 90.0%-110.0% |
| | Impurities | Impurity A NMT 5.0%, Any Unidentified Impurity: NMT 0.10%, Total Impurities: NMT 7.0% |
| | EDTA Content | 0.050 to 0.150% w/v at time zero; 0.010 to 0.150% w/v for stability samples |
| | Sodium benzoate | 0.015-0.045% w/v (30 mg/ml); 0.050 to 0.150% w/v (100 mg/ml) |

UD—Unidentified,
ND—Not Detected,
NMT—Not More Than,
NA—Not Available

All the tested product characteristics, i.e., appearance, assay, pH, EDTA content, and sodium benzoate content remained unaffected after 3 months of in-use studies for 100 mg/mL strength and for 2 months of in-use studies for 30 mg/mL strength. There was a slight increase in the impurity A level for the 30 mg/mL strength after 2 months of testing. However, since a similar level of impurity A was observed in the control sample, due to the anticipated, minor oxidative degradation upon storage, it was concluded that the rise in impurity level was not a result of the in-use sampling.

This study was conducted concurrently with scale-up and process optimization studies. It could be seen that the tested compositions exhibit acceptable stability during in use-studies, for up to 3 months, for the 100 mg/ml chlorpromazine hydrochloride strength, and for 2 months for the 30 mg/ml strength. Thus, the compositions were deemed suitable for process validation studies.

Example 15

FIG. 3 is a process flow diagram for the formulation of embodiments of oral liquid compositions according to the present disclosure comprising 100 mg/mL and 30 mg/mL chlorpromazine hydrochloride. All the unit operations in the manufacturing process are listed in the sequence of occurrence. Material attributes and manufacturing process parameters that have the potential to impact intermediate and finished product quality attributes are also presented. The material attributes of the input materials and the process parameters used at the first process step determine the quality attributes of the output material (intermediate) produced at that step. Attributes of the intermediate from that step and process parameters of the subsequent unit operations in the manufacturing scheme will determine quality attributes of the next intermediate and, eventually, those of the finished product. This cycle is repeated until the final process step in which the finished drug product is manufactured, and the finished product quality attributes are evaluated. For the current product the CQAs were identical for each step. Therefore, nearly all the CQAs were evaluated after each manufacturing step to determine their impact on the following process steps.

During the manufacturing of these process optimization batches and evaluation of the product development stability samples a slight discoloration of the product was observed at different stages. Therefore, as described herein, edetate disodium (EDTA) was added as a chelating agent to the formulation to prevent discoloration as it was attributed to oxidation of chlorpromazine hydrochloride due to the presence of trace metal ion impurities in the excipients. Since process optimization was already performed with the formulations without EDTA, a verification batch, for each strength, was manufactured at the low end of the established process parameter ranges (low mixing speed and time). During formulation development it was observed that EDTA readily dissolves in the formulation and a separate mixing step for EDTA is not necessary. Therefore, it was determined that additional batches at the low end of the process parameter ranges would be sufficient to verify the complete dissolution of the ingredient. The lower end of the process parameter range was selected since it would represent the worst case scenario for the dissolution of the ingredients. The composition of the batches used for process optimization and verification are given below in Tables 60-63.

TABLE 60

Formulation composition for the process optimization batch of composition comprising 30 mg per mL chlorpromazine hydrochloride

| Weight/Volume (mg/mL) | Component | Percent (w/v) | Theoretic Weight |
|---|---|---|---|
| Active Ingredients | | | |
| 30.000 | Chlorpromazine Hydrochloride | 3.000 | 6.75 kg |
| Excipients | | | |
| 9.000 | Sucralose, NF | 0.900 | 2.025 kg |
| 0.300 | Sodium Benzoate, NF | 0.030 | 67.50 g |
| 1.566 | Sodium Citrate Dihydrate, USP | 0.157 | 352.35 g |
| 1.018 | Citric Acid Anhydrous, USP | 0.102 | 229.05 g |
| 968.116 | Purified Water, USP | 96.812 | 217.83 kg |
| | Total | 101.000 | 227.25 kg |

TABLE 61

Formulation composon for the process optimization batch of composition comprising 100 mg per mL chlorpromazine hydrochloride

| Weight/Volume (mg/mL) | Component | Percent (w/v) | Theoretical Weight |
|---|---|---|---|
| Active Ingredients | | | |
| 100.000 | Chlorpromazine Hydrochloride | 10.000 | 22.50 kg |
| Excipients | | | |
| 30.000 | Sucralose, NF | 3.000 | 6.75 kg |
| 1.000 | Sodium Benzoate, NF | 0.100 | 225.00 g |
| 5.220 | Sodium Citrate Dihydrate, USP | 0.522 | 1.175 kg |
| 3.393 | Citric Acid Anhydrous, USP | 0.339 | 763.50 g |
| 898.387 | Purified Water, USP | 89.839 | 202.14 kg |
| | Total | 103.800 | 233.55 kg |

TABLE 62

Formulation composition for verification batch of composition comprising 30 mg/mL chlorpromazine hydrochloride

| Weight/Volume (mg/mL) | Component | Percent (w/v) | Theoretical Weight |
|---|---|---|---|
| Active Ingredients | | | |
| 30.000 | Chlorproniazine Hydrochloride | 3.000 | 6.75 kg |
| Excipients | | | |
| 9.000 | Sucralose, NF | 0.900 | 2.025 kg |
| 0.300 | Sodium Benzoate, NF | 0.030 | 67.50 g |
| 1.566 | Sodium Citrate Dihydrate, USP | 0.157 | 352.35 g |
| 1.018 | Citric Acid Anhydrous, USP | 0.102 | 229.05 g |
| 1.000 | Edetate Disodium, USP | 0.100 | 225.00 g |
| 968.116 | Purified Water, USP | 96.812 | 217.83 kg |
| | Total | 101.100 | 227.475 kg |

TABLE 63

Formulation composition for verification batch of composition comprising 100 mg/mL chlorpromazine hydrochloride

| Weight/Volume (mg/mL) | Component | Percent (w/v) | Theoretical Weight |
|---|---|---|---|
| | Active Ingredients | | |
| 100.000 | Chlorpromazine Hydrochloride | 10.000 | 22.50 kg |
| | Excipients | | |
| 30.000 | Sucralose, NF | 3.000 | 6.75 kg |
| 1.000 | Sodium Benzoate, NF | 0.100 | 225.00 g |
| 5.720 | Sodium Citrate Dihydrate, USP | 0.522 | 1.175 kg |
| 3.393 | Citric Acid Anhndrous, USP | 0.339 | 763.50 g |
| 1.000 | Edetate Disodium, USP | 0.100 | 225.00 g |
| 898.387 | Purified Water, USP | 89.839 | 202.14 kg |

The compositions of Tables 60-63 were manufactured by mixing the active and inactive ingredients in a 75 gallon stainless steel mixing tank with a stainless steel stirrer. The tank contains one discharge valve that is located on the bottom of the tank. The discharge valve is a 1½" short shank F.T.P.V. sanitary thread valve made of stainless steel. The tank has a stainless steel stiffer fitted with two 7.0" inch marine blades in a staggered configuration. The mixing process can be adjusted by changing the mixer speed.

After mixing, the bulk drug product solution was filtered through a 5 μm filter cartridge into a stainless steel holding tank. The filter cartridge and the stainless steel filter housing were connected to the process pump, and the solution was filtered through the filter media into the stainless steel holding tank. All connections that required tubing utilized FDA approved platinum cured silicone tubing.

From each batch, samples were obtained from the approximate top, middle and bottom, and left, center and right, respectively, of the unfiltered bulk drug product from the mixing tank to verify complete dissolution of ingredients at the optimized parameters. Samples were also obtained at the beginning, middle and end of the filtration process. A portable sampler fitted with a peristaltic pump was used to obtain the samples from the mixing and holding tanks. In addition, samples from the holding tank were transferred into 0.5 L stainless steel containers for a bulk drug product hold time study.

Additionally, filtered bulk drug product solution from the process optimization batches (one for each strength) and verification batches was held in the 0.5 L stainless steel container, comparable to the holding tank, for a period of 30 days, and samples were withdrawn at 15 days and 30 days for evaluation of the CQAs. The samples from the process optimization batches were stored without a nitrogen blanket. Samples from the verification batches were stored with and without a nitrogen blanket. The containers were purged with nitrogen prior to initiation of the hold time and were purged again after sample withdrawal on day 15.

Based on the observations of the process optimization and verification batches, the mixing speed and mixing time ranges were established for the stability/process performance qualification (PPQ) batches. The evaluated and optimized ranges are shown in Tables 64-67. Results of the samples withdrawn during manufacturing are present in Table 68A-B, Table 69, Table 70A-C, Table 71, Table 72, and Table 73. Results for the bulk drug product hold studies are shown in Tables 74 and 75.

TABLE 64

Mixing Speed: Chlorpromazine Hydrochloride Oral Concentrate, USP, 30 mg/mL

| | Mixing Speed (RPM) | | |
|---|---|---|---|
| Parameter Step | Low Mixing Speed | High Mixing Speed | Proposed Mixing Speed |
| Initial mixer speed set up | 130 | 200 | 135-195 |
| Dissolution of sucralose, sodium benzoate, disodium edetate[a], anhydrous citric acid, sodium citrate dihydrate | 130 | 201 | 135-195 |
| Dissolution of chlorpromazine hydrochloride | 130 | 200 | 135-195 |

[a]Included in verification batch only

TABLE 65

Mixing Time: Chlorpromazine Hydrochloride Oral Concentrate, USP, 30 mg/mL

| | Mixing Time (minutes) | | |
|---|---|---|---|
| Parameter Step | Low Mixing Time | High Mixing Time | Proposed Mixing Time |
| Initial mixer speed set up | NA | NA | NA |
| Dissolution of sucralose, sodium benzoate, disodium edetate[a], anhydrous citric acid, sodium citrate dihydrate | 10 | 30 | 11-29 |
| Dissolution of chlorpromazine hydrochloride | 15 | 35 | 116-34 |

[a]Included in verification batch only

TABLE 66

Mixing Speed: Chlorpromazine Hydrochloride Oral Concentrate, USP, 100 mg/mL

| | Mixing Speed (RPM) | | |
|---|---|---|---|
| Parameter Step | Low Mixing Speed | High Mixing Speed | Proposed Mixing Speed |
| Initial mixer speed set up | 130 | 200 | 135-195 |
| Dissolution of sucralose, sodium benzoate, disodium edetate[a], anhydrous citric acid, sodium citrate dihydrate | 130 | 200 | 135-195 |
| Dissolution of chlorpromazine hydrochloride | 130 | 200 | 135-195 |

[a]Included in verification batch only.

TABLE 67

Mixing Time: Chlorpromazine Hydrochloride Oral Concentrate, USP, 100 mg/mL

| | Mixing Time (minutes) | | |
|---|---|---|---|
| Parameter Step | Low Mixing Time | High Mixing Time | Proposed Mixing Time |
| Initial mixer speed set up | NA | NA | NA |
| Dissolution of sucralose, sodium benzoate, disodium edetate[a], anhydrous citric acid, sodium citrate dihydrate | 15 | 35 | 16-34 |
| Dissolution of chlorpromazine hydrochloride | 70 | 40 | 21-39 |

[a]Included in verification batch only

TABLE 68A

Results of the Bulk Drug Product Testing of Chlorpromazine Hydrochloride Oral Concentrate, USP, 30 mg/mL

| Parameter | Sample Location | Specifications | Optimization Batch (Low Mixing Time & Speed) 30 mg per mL NB 538-079, 227.25 kg | Optimization Batch (High Mixing Time & Speed) 30 mg per mL NB 538-082, 227.25 kg | Verification Batch (Low Mixing Time & Speed) 30 mg per mL NB 538-109, 227.48 kg |
|---|---|---|---|---|---|
| pH | Top Left | 2.0-5.0 | 3.9 | 3.9 | 3.9 |
| | Top Center | | 3.9 | 3.9 | 3.8 |
| | Top Right | | 3.9 | 3.9 | 3.9 |
| | Middle Left | | 3.9 | 3.9 | 3.9 |
| | Middle Center | | 3.9 | 3.9 | 3.9 |
| | Middle Right | | 3.9 | 3.9 | 3.9 |
| | Bottom Left | | 3.9 | 3.9 | 3.9 |
| | Bottom Center | | 3.9 | 3.9 | 3.9 |
| | Bottom Right | | 3.9 | 3.9 | 3.9 |
| | Beginning of Filtration | | 3.9 | 3.9 | 3.9 |
| | Middle of Filtration | | 3.9 | 3.9 | 3.9 |
| | End of Filtration | | 3.9 | 3.9 | 3.9 |
| | Filtered Composite | | 3.9 | 3.9 | 3.9 |
| Assay of Chlorpromazine Hydrochloride | Top Left | 90.0%-110.0% | 99.4 | 100.2 | 101.3 |
| | Top Center | | 99.9 | 99.8 | 101.0 |
| | Top Right | | 100.7 | 99.4 | 100.8 |
| | Middle Left | | 99.4 | 100.0 | 101.0 |
| | Middle Center | | 100.0 | 99.9 | 101.0 |
| | Middle Right | | 99.9 | 100.2 | 100.8 |
| | Bottom Left | | 99.8 | 100.2 | 100.9 |
| | Bottom Center | | 99.6 | 100.1 | 101.1 |
| | Bottom Right | | 100.2 | 99.9 | 100.9 |
| | Beginning of Filtration | | 99.7 | 100.3 | 101.7 |
| | Middle of Filtration | | 99.9 | 100 | 101.2 |
| | End of Filtration | | 100.4 | 100.4 | 100.9 |
| | Filtered Composite | | 99.6 | 99.9 | 101.9 |

TABLE 68B

Results of the Bulk Drug Product Testing of Chlorpromazine Hydrochloride Oral Concentrate, USP, 30 mg/mL (continued)

| Parameter | Sample Location | Specifications | Optimization Batch (Low Mixing Time & Speed) 30 mg per mL NB 538079, 227.25 kg | | Optimization Batch (High Mixing Time & Speed) 30 mg per mL NB 538-082, 227.25 kg | | Verification Batch (Low Mixing Time & Speed) 30 mg per mL NB 538409, 227.48 kg | |
|---|---|---|---|---|---|---|---|---|
| Preservative | | | % w/v | % Label Claim | % w/v | % Label Claim | % w/v | % Label Claim |
| Content (Sodium Benzoate)[1] | Top Left | 0.015%-0.045% w/v (As labeled 50%-150%) | 0.030 | 100.0 | 0.010 | 98.4 | 0.029 | 97.2 |
| | Top Center | | 0.02 | 98.1 | 0.029 | 97.8 | 0.030 | 98.5 |
| | Top Right | | 0.030 | 101.2 | 0.030 | 98.6 | 0.029 | 95.6 |
| | Middle Left | | 0.030 | 100.9 | 0.029 | 97.3 | 0.029 | 95.7 |
| | Middle Center | | 0.030 | 101.6 | 0.010 | 99.0 | 0.029 | 97.9 |
| | Middle Right | | 0.030 | 101.4 | 0.029 | 97.9 | 0.029 | 96.0 |
| | Bottom Left | | 0.031 | 101.9 | 0.029 | 97.4 | 0.030 | 99.4 |
| | Bottom Center | | 0.030 | 101.3 | 0.029 | 97.3 | 0.029 | 96.9 |
| | Bottom Right | | 0.030 | 98.8 | 0.029 | 97.1 | 0.029 | 96.7 |
| | Beginning of Filtration | | 0.030 | 101.0 | 0.030 | 99.0 | 0.030 | 100.0 |
| | Middle of Filtiation | | 0.030 | 100.8 | 0.030 | 100.1 | 0.030 | 100.6 |
| | End of Filtration | | 0.030 | 101.2 | 0.030 | 99.9 | 0.029 | 98.2 |
| | Filtered Composite | | 0.030 | 101.0 | 0.030 | 101.0 | 0.030 | 101.2 |
| Edetate Disodium Content[1] | TopLeft | 0.05- 0.15% w/v (As labeled 50%-150%) | NA | NA | | | 0.10 | 99.0 |
| | Top Center | | | | | | 0.10 | 98.4 |
| | Top Right | | | | | | 0.10 | 98.4 |
| | Middle Left | | | | | | 0.10 | 98.5 |
| | Middle Center | | | | | | 0.10 | 98.6 |
| | Middle Right | | | | | | 0.10 | 98.6 |
| | Bottom Left | | | | | | 0.10 | 98.6 |
| | Bottom Center | | | | | | 0.10 | 98.6 |
| | Bottom Right | | | | | | 0.10 | 98.8 |
| | Beginning of Filtration | | | | | | 0.10 | 98.2 |
| | Middle of Filtration | | | | | | 0.10 | 98.6 |
| | End of Filtration | | | | | | 0.10 | 98.5 |
| | Filtered Composite | | | | | | 0.10 | 98.8 |

[1] Reported results have been rounded off as per respective test specifications

TABLE 69

Results of % RSD (Relative Standard Deviation) for the bulk drug product testing of Chlorpromazine Hydrochloride Oral Concentrate, USP, 30 mg/mL

| | % RSD[1] | | |
|---|---|---|---|
| Parameter | Optimization Batch (Low Mixing Time & Speed) 30 mg per mL NB 538-079, 227.25 kg | Optimization Batch (High Mixing Time & Speed) 30 mg per mL NB 538-081, 227.25 kg | Verification Batch (Low Mixing Time & Speed) 30 mg per mL NB 538-109, 227.475 kg |
| pH | 0.3 | 0.2 | 0.6 |
| Assay of Chlorpromazine Hydrochloride | 0.4 | 0.3 | 0.3 |
| Preservative Content | 1.1 | 1.0 | 1.7 |
| Edetate Disodium Content | NA | NA | 0.2 |
| Specification | Not More Than 2% | | |

[1]Results for the filtered composite sample were not included in the calculations

TABLE 70A

Results of Bulk Drug Product Testing of Chlorpromazine Hydrochloride Oral Concentrate, USP, 100 mg/mL

| Parameter | Sample Location | Specifications | Optimization Batch (Low Mixing Time & Speed) 100 mg per mL | Optimization Batch (High Mixing Time & Speed) 100 mg per mL | Verification Batch (Low Mixing Time & Speed) 100 mg per mL |
|---|---|---|---|---|---|
| pH | Top Left | 2.0-5.0 | 3.9 | 3.9 | 3.9 |
| | Top Center | | 3.9 | 3.9 | 3.9 |
| | Top Right | | 3.9 | 3.9 | 3.9 |
| | Middle Left | | 3.9 | 3.9 | 3.8 |
| | Middle Center | | 3.9 | 3.9 | 3.9 |
| | Middle Right | | 3.9 | 3.9 | 3.8 |
| | Bottom Left | | 3.9 | 3.9 | 3.8 |
| | Bottom Center | | 3.9 | 3.9 | 3.8 |
| | Bottom Right | | 3.9 | 3.9 | 3.9 |
| | Beginning of Filtration | | 3.9 | 3.9 | 3.8 |
| | Middle of Filtration | | 3.9 | 3.9 | 3.9 |
| | End of Filtration | | 3.9 | 3.9 | 3.9 |
| | Filtered Composite | | 3.9 | 3.9 | 3.8 |

TABLE 70B

Results of Bulk Drug Product Testing of Chlorpromazine Hydrochloride Oral Concentrate, USP, 100 mg/mL (continued)

| Parameter | Sample Location | Specifications | Optimization Batch (Low Mixing Time & Speed) 100 mg per mL NB 538-080, 233.55 kg | Optimization Batch (High Mixing Time & Speed) 100 mg per mL NB 538-083, 233.55 kg | Verification Batch (Low Mixing Time & Speed) 100 mg per mL NB 538108, 233.78 kg |
|---|---|---|---|---|---|
| Assay for Chlorpromazine Hydrochloride | Top Left | 90.0%-11.0.0% | 99.3 | 100.4 | 101.7 |
| | Top Center | | 99.4 | 100.2 | 102.1 |
| | Top Right | | 99.1 | 100.6 | 101.9 |
| | Middle Left | | 99.2 | 100.2 | 100.9 |
| | Middle Center | | 99.5 | 99.8 | 101.4 |
| | Middle Right | | 99.5 | 100.2 | 101.4 |
| | Bottom Left | | 99.5 | 101.4 | 101.5 |
| | Bottom Center | | 99.4 | 100.2 | 101.5 |
| | Bottom Right | | 98.9 | 100.6 | 101.5 |
| | Beginning of Filtration | | 99.3 | 100.1 | 101.6 |
| | Middle of Filtration | | 99.4 | 100.2 | 101.3 |
| | End of Filtration | | 99.4 | 100.4 | 101.4 |
| | Filtered Composite | | 99.4 | 100.7 | 101.7 |
| | | | % w/v  % Label Claim | % w/v  % Label Claim | % w/v  % Label Claim |
| Preservative Content (Sodium Benzoate)1 | Top Left | 0.05-0.15% w/v (As labeled 50%-150%) | 0.096  96.2 | 0.099  98.6 | 0.098  97.9 |
| | Top Center | | 0.098  97.8 | 0.099  99.0 | 0.100  99.7 |
| | Top Right | | 0.100  100.0 | 0.098  97.6 | 0.097  97.3 |

TABLE 70B-continued

Results of Bulk Drug Product Testing of Chlorpromazine Hydrochloride Oral Concentrate, USP, 100 mg/mL (continued)

| Parameter | Sample Location | Specifications | Optimization Batch (Low Mixing Time & Speed) 100 mg per mL NB 538-080, | | Optimization Batch (High Mixing Time & Speed) 100 mg per mL NB 538-083, | | Verification Batch (Low Mixing Time & Speed) 100 mg per mL NB 538108, | |
|---|---|---|---|---|---|---|---|---|
| | Middle Left | | 0.096 | 96.0 | 0.098 | 98.3 | 0.098 | 98.1 |
| | Middle Center | | 0.099 | 99.2 | 0.098 | 98.3 | 0.098 | 97.9 |
| | Middle Right | | 0.099 | 98.9 | 0.098 | 98.1 | 0.098 | 97.7 |
| | Bottom Left | | 0.098 | 98.0 | 0.098 | 97.5 | 0.098 | 97.6 |
| | Bottom Center | | 0.101 | 100.5 | 0.097 | 97.2 | 0.098 | 97.8 |
| | Bottom Right | | 0.097 | 96.8 | 0.097 | 97.5 | 0.097 | 97.4 |
| | Beginning of Filtration | | 0.098 | 98.3 | 0.100 | 99.5 | 0.098 | 98.1 |
| | Middle of Filtration | | 0.099 | 99.1 | 0.101 | 100.8 | 0.099 | 99.5 |
| | End of Filtration | | 0.098 | 98.0 | 0.100 | 99.9 | 0.098 | 97.8 |
| | Filtered Composite | | 0.097 | 96.5 | 0.101 | 100.6 | 0.099 | 99.2 |

TABLE 70C

Results of Bulk Drug Product Testing of Chlorpromazine Hydrochloride Oral Concentrate, USP, 100 mg/mL (continued)

| Parameter | Sample Location | Specifications | Optimization Batch (Low Mixing Time & Speed) 100 mg per mL NB 538-080, 233.55 kg | | Optimization Batch (High Mixing Time & Speed) 100 mg per raL NB 538-083, 233.55 kg | | Verification Batch (Low Mixing Time & Speed) 100 mg per mL NB 538-108, 233.78 kg | |
|---|---|---|---|---|---|---|---|---|
| Edetate Disodium Content[1] | Top Left | 0.05-0.15% w/v (As labeled 50%-150%) | NA | | NA | | 0.10 | 98.9 |
| | Top Center | | | | | | 0.10 | 98.8 |
| | Top Right | | | | | | 0.10 | 98.6 |
| | Middle Left | | | | | | 0.10 | 98.8 |
| | Middle Center | | | | | | 0.10 | 98.8 |
| | Middle Right | | | | | | 0.10 | 98.5 |
| | Bottom Left | | | | | | 0.10 | 98.5 |
| | Bottom Center | | | | | | 0.10 | 98.7 |
| | Bottom Right | | | | | | 0.10 | 98.7 |
| | Beginning of Filtration | | | | | | 0.10 | 98.8 |
| | Middle of Filtration | | | | | | 0.10 | 98.7 |
| | End of Filtiation | | | | | | 0.10 | 99.1 |
| | Filtered Composite | | | | | | 0.10 | 98.8 |

[1]Reported results have been rounded off as per respective test specifications

TABLE 71

Results of % RSD (relative standard deviation) for bulk drug product testing of Chlorpromazine Hydrochloride Oral Concentrate, USP, 100 mg/mL

| | % RSD[1] | | |
|---|---|---|---|
| Parameter | Optimization Batch (Low Mixing Time & Speed) 100 mg per mL NB 538-080, 233.55 kg | Optimization Batch (High Mixing Time & Speed) 100 mg per mL NB 538-083, 233.55 kg | Verification Batch (Low Mixing Time & Speed) 100 mg per mL NB 538-108, 233.78 kg |
| pH | 0.2 | 0.3 | 0.9 |
| Assay of Chlorpromazine Hydrochloride | 0.2 | 0.4 | 0.3 |
| Preservative Content | 1.4 | 1.1 | 0.8 |
| Edetate Disodium Content | NA | NA | 0.2 |
| Specifications | | ≤2% | |

[1]Results for the filtered composite sample were not included in the calculations

TABLE 72

Results of Related Substances for the Bulk Drug Product
Testing of Process Optimization Batches

| Batch Type | Batch Number and Size | Location | Impurity A (%) | Any Unidentified Impurity (%) | Total Impurities (%) |
|---|---|---|---|---|---|
| Optimization Batch (Low Mixing Time & Speed) 30 mg per mL | NB 538-079, 227.25 kg | Beginning of Filtration | <0.05 | <0.05 | <0.05 |
| | | Middle of Filtration | <0.05 | <0.05 | <0.05 |
| | | End of filtration | <0.05 | <005 | <0.05 |
| | | Composite Sample | <0.05 | <0.05 | <0.05 |
| Optimization Batch (High Mixing Time & Speed) 30 mg per mL | NB 538-082, 227.25 kg | Beginning of Filtration | <0.05 | <0.05 | <0.05 |
| | | Middle of Filtration | <0.05 | <0.05 | <0.05 |
| | | End of filtration | <0.05 | <0.05 | <0.05 |
| | | Composite Sample | <0.05 | <0.05 | <0.05 |
| Optimization Batch (Low Mixing Time & Speed) 100 mg per mL | NB 538-080, 233.55 kg | Beginning of Filtration | <0.05 | <005 | <0.05 |
| | | Middle of Filtration | <0.05 | <0.05 | <0.05 |
| | | End of filtration | <0.05 | <0.05 | <0.05 |
| | | Composite Sample | <0.05 | <0.05 | <0.05 |
| Optimization Batch (High Mixing Time & Speed) 100 mg per mL | NB 538-083, 233.55 kg | Beginning of Filtration | <0.05 | <0.05 | <0.05 |
| | | Middle of Filtration | <0.05 | <0.05 | <0.05 |
| | | End of filtration | <0.05 | <0.05 | <0.05 |
| | | Composite Sample | <0.05 | <0.05 | <0.05 |

TABLE 73

Results of Related Substances for the Bulk Drug Product Testing of the Verification Batches

| Parameter | Verification Batch (Low Mixing Time & Speed) 30 mg per mL NB 538409, 227.475 kg | | | | Verification Batch (Low Mixing Time & Speed) 100 mg per mL, NB 538408, 233.775 kg | | | |
|---|---|---|---|---|---|---|---|---|
| Location | Beginning of Filtration | Middle of Filtration | End of Filtration | Composite Sample | Beginning of Filtration | Middle of Filtration | End of Filtration | Composite Sample |
| Impurity A (%) | <0.05 | <0.05 | <0.05 | <0.05 | <0.05 | <0.05 | <0.05 | <0.05 |
| Any Unidentified Impurity (%) | <00.5 | <005 | <0.05 | <0.05 | <0.05 | <0.05 | <00.5 | <005 |
| Total Impurities (%) | <0.05 | <0.05 | <0.05 | <0.05 | <0.05 | <0.05 | <0.05 | <0.05 |

TABLE 74

Results of drug product testing of the bulk drug product hold study samples from the process optimization and
verification batches for Chlorpromazine Hydrochloride Oral Concentrate, USP, 30 mg/mL

| Parameter | Sample Location (Days) | Limits | Process Optimization Batch (Low Mixing Time & Speed) 30 mg per mL NB 538-079, 227.25 kg Packed without Nitrogen (N$_2$) Blanket | Verification Batch (Low Mixing Time & Speed) 30 mg per mL NB 538-109, 227.475 kg Low Mixing Time & Speed, Packed with N$_2$ Blanket | Verification Batch (Low Mixing Time & Speed) 30 mg per mL NB 538-109, 227.475 kg Low Mixing Time & Speed, Packed without N$_2$ Blanket |
|---|---|---|---|---|---|
| Description | 15 | Clear Liquid | Clear Liquid | Clear Liquid | Clear Liquid |
| | 30 | | Clear Liquid | Clear Liquid | Clear Liquid |
| pH | 15 | 2.0-5.0 | 3.9 | 3.9 | 3.9 |
| | 30 | | 3.8 | 3.9 | 4.1 |

TABLE 74-continued

Results of drug product testing of the bulk drug product hold study samples from the process optimization and verification batches for Chlorpromazine Hydrochloride Oral Concentrate, USP, 30 mg/mL

| Parameter | Sample Location (Days) | Limits | Process Optimization Batch (Low Mixing Time & Speed) 30 mg per mL NB 538-079, 227.25 kg Packed without Nitrogen (N$_2$) Blanket | | | Verification Batch (Low Mixing Time & Speed) 30 mg per mL NB 538-109, 227.475 kg Low Mixing Time & Speed, Packed with N$_2$ Blanket | | | Verification Batch (Low Mixing Time & Speed) 30 mg per mL NB 538-109, 227.475 kg Low Mixing Time & Speed, Packed without N$_2$ Blanket | | |
|---|---|---|---|---|---|---|---|---|---|---|---|
| Assay for Chlorpromazine Hydrochloride | 15 | 90.0%-110.0% | 100.5 | | | 100.1 | | | 99.3 | | |
| | 30 | | 99.8 | | | 100.8 | | | 100.2 | | |
| Preservative Content (Sodium Benzoate) | 15 | 0.015%-0.045% w/v (As labeled 50%-150%) | 0.030 | | | 0.030 | | | 0.029 | | |
| | 30 | | 0.029 | | | 0.030 | | | 0.030 | | |
| Edetate Disodium | 15 | 0.05%-0.15% w/v (As labeled 50.0%-150%) | N/A | | | 0.098 | | | 0.097 | | |
| | 30 | | | | | 0.097 | | | 0.095 | | |
| | | | Imp. A | UD | Total | Imp. A | UD | Total | Imp. A | UD | Total |
| Related Substances | 15 | Impurity A: NMT 5.0% Any UD: NMT 0.1% Total ≤ 10% | <0.05 | <0.05 | <0.05 | <0.05 | <0.05 | <0.05 | <0.06 | <0.05 | <0.06 |
| | 30 | | <0.05 | <0.05 | <0.05 | <0.05 | <0.05 | <0.05 | <0.09 | <0.05 | <0.09 |

NMT = not more than; UD = unidentified

TABLE 75

Results of drug product testing of the bulk drug product hold study samples from the process optimization and verification batches for Chlorpromazine Hydrochloride Oral Concentrate, USP, 100 mg/mL

| Parameter | Sample Location (Days) | Limits | Process Optimization Batch (Low Mixing Time & Speed) 100 mg per mL NB 538-080, 233.55 kg Packed without N$_2$ Blanket | | | Verification Batch (Low Mixing Time & Speed) 100 mg per mL NB 538-108, 233.78 kg Packed with N$_2$ Blanket | | | Verification Batch (Low Mixing Time & Speed) 100 mg per mL NB 538-108, 233.78 kg Packed without N$_2$ Blanket | | |
|---|---|---|---|---|---|---|---|---|---|---|---|
| Description | 15 | Clear Liquid | Clear Liquid | | | Clear Liquid | | | Clear Liquid | | |
| | 30 | | Clear Liquid | | | Clear Liquid | | | Clear Liquid | | |
| pH | 15 | 2.0-5.0 | 3.9 | | | 3.9 | | | 3.9 | | |
| | 30 | | 3.9 | | | 4.0 | | | 3.9 | | |
| Assay for Chlorpromazine Hydrochloride | 15 | 90.0%-110.0% | 100.1 | | | 100.2 | | | 99.6 | | |
| | 30 | | 99.5 | | | 100.3 | | | 100.4 | | |
| Preservative Content (Sodium Benzoate) | 15 | 0.050%-0.150% w/v (As labeled 50.0%-150%) | 0.099 | | | 0.100 | | | 0.100 | | |
| | 30 | | 0.101 | | | 0.100 | | | 0.101 | | |
| Edetate Disodium Content | 15 | 0.05%-0.15% w/v (As labeled 50.0%-150%) | N/A | | | 0.097 | | | 0.096 | | |
| | 30 | | | | | 0.097 | | | 0.095 | | |
| | | | Imp. A | UD | Total | Imp. A | UD | Total | Imp. A | UD | Total |
| Related Substances | 15 | Impurity A: NMT 5.0% Any UD: NMT 0.1% Total ≤ 10% | <0.05 | <0.05 | <0.05 | <0.05 | <0.05 | <0.05 | 0.05 | <0.05 | 0.05 |
| | 30 | | <0.05 | <0.05 | <0.05 | <0.05 | <0.05 | <0.05 | 0.05 | <0.05 | 0.05 |

NMT = not more than; UD = unidentified

As described above, discoloration of the product during bulk drug product hold and stability studies was mitigated by the addition of EDTA to the formulation and purging the holding tank and the primary packaging containers with nitrogen before and after filling the product. The flow rate and duration of purging for the holding tank was defined by the volume of nitrogen necessary to occupy the empty space in the tank. The amount of nitrogen purged before product transfer was in slight excess of the fill volume of the holding tank. Nitrogen was also purged after product transfer; the volume of nitrogen purged was in slight excess of the tank headspace after product transfer. The bulk drug product was found to be stable and within specifications even in the absence of nitrogen (Table 72 and Table 73).

The samples from all the process optimization and verification batches met the acceptance criteria. Additionally, the results for the CQAs from all the batches were nearly identical. The results of the samples obtained from the beginning, middle and end of the filtration processes, irrespective of the strength and parameter specifications, were nearly identical, thus demonstrating that there is no interaction between the filter and the product.

The bulk hold stability results demonstrated that the product CQAs met the specifications for up to the studied duration of 1 month and are not significantly affected by the absence of a nitrogen blanket in the headspace of the holding tank. The discoloration of the product in the holding tank was mitigated by addition of EDTA. Although the CQAs are not significantly affected by the presence of a nitrogen blanket, it was included in the process as a precautionary measure to inhibit oxidative degradation due to excipient lot-to-lot variation, or variation in the dissolved oxygen levels caused by variation in the environmental conditions.

Example 16

During initial assessment it was determined nitrogen purging flow rate and duration were expected to have a significant impact on the appearance and overall stability of the product. In order to determine the extent of nitrogen purging necessary before and after filling primary packaging containers (PET bottles), to obtain a stable product, the dissolved oxygen (DO) levels before and after purging with nitrogen at a fixed flow rate and various durations were evaluated. This study was performed on oral liquid compositions according to the present disclosure comprising 30 mg/mL chlorpromazine hydrochloride since this strength was determined as the worst case scenario for the potential of oxidation. Batch NB538-112 was manufactured at a batch size of 227.25 kg (225 L) using the target mixing time and mixing speed parameters identified in the process optimization studies. The formulation composition for batch NB538-112 is shown in Table 76 below.

TABLE 76

Formulation composition for Batch NB538-0012

| Weight/Volume (mg/mL) | Component | Percent (w/v) | Theoretical Weight |
|---|---|---|---|
| Active Ingredients | | | |
| 30.000 | Chlorpromazine Hydrochloride | 3.000 | 6.75 kg |
| Excipients | | | |
| 9.000 | Sucralose, NF | 0.900 | 2.025 kg |
| 0.300 | Sodium Benzoate, NF | 0.030 | 67.50 g |
| 1.566 | Sodium Citrate Dihydrate, USP | 0.1566 | 352.35 g |
| 1.018 | Citric Acid Anhydrous, USP | 0.1018 | 229.05 g |
| 1.000 | Edetate Disodium, USP | 0.100 | 225.00 g |
| 968.116 | Purified Water, USP | 96.8116 | 217.83$^a$ kg |
| | Total | 101.10000 | 227.475 kg |

$^a$Amounts have been rounded to accommodate balance/scale tolerances

After manufacturing, the filtered bulk drug product was transferred to a 200 gallon stainless steel holding tank and then blanketed with nitrogen. The oxygen level of the bulk drug product prior to blanketing with nitrogen was determined to be 8.74 mg/L. The holding tank was blanketed with nitrogen by purging for 36 minutes at 30 standard cubic feet per hour (scfh). The dissolved oxygen (DO) level obtained immediately after blanketing was 8.70 mg/L, and after holding overnight was determined to be 8.08 mg/L. The DO levels during manufacturing, after packaging, and after stability studies were measured by using a dissolved oxygen meter (with a galvanic probe).

The product was packaged on the packaging line intended to be used for commercial packaging of the product, in 120 cc PET bottles with 24 mm child resistant (CR) cap. The bottles were manually purged with nitrogen prior to filling the product and blanketed with nitrogen after filling the product. The nitrogen flow rate used for purging and blanketing the bottles was 60 SL/min and 10 L/min, respectively. The induction sealer power was set to 35%. The packaged bottles were stored at 60° C. for 7 days and 15 days. The DO levels immediately after packaging were measured. The results of the DO level measurements are shown in Table 77. The results from analytical testing are shown in Table 78. Based upon observations of this study, nitrogen purge flow rate and duration for each step were established for process performance and qualification batches and are shown in Table 79.

TABLE 77

Dissolved oxygen (DO) levels in mg/L of Chlorpromazine Hydrochloride Oral Concentrate, USP, 30 mg/ml, Batch #NB538-112, immediately after packaging

| Bottle Number | Purge Time: 0 Sec Blanket Time: 0 Sec | Purge Time: 10 Sec Blanket Time: 0 Sec | Purge Time: 0 Sec Blanket Time: 10 Sec | Purge Time: 10 Sec Blanket Time: 10 Sec |
|---|---|---|---|---|
| 1 | 8.12 | 5.90 | 6.80 | 5.38 |
| 2 | 7.31 | 5.38 | 4.90 | 4.92 |
| 3 | 8.11 | 5.34 | 5.86 | 4.78 |
| 4 | 9.05 | 5.44 | 5.90 | 4.97 |
| 5 | 8.29 | 5.77 | 6.91 | 5.30 |
| 6 | 8.11 | 6.53 | 6.79 | 5.34 |
| 7 | 8.34 | 6.43 | 5.66 | 5.10 |
| 8 | 8.08 | 6.68 | 6.71 | 5.62 |
| 9 | 8.31 | 6.04 | 5.59 | 4.90 |
| 10 | 8.21 | 7.30 | 5.80 | 5.19 |
| Average | 8.19 | 6.08 | 6.09 | 5.15 |
| Standard Deviation | 0.40 | 0.61 | 0.64 | 0.25 |

TABLE 78

Analytical testing results of the packaged drug product Chlorpromazine Hydrochloride Oral Concentrate, USP, 30 mg/ml batch NB538412 at time zero and after storage for 7 days and 15 days at 60° C.

| Condition | Comments | Reference | % Assay | Individual Impurity (%) Impurity A | Individual Impurity (%) Any UD | Total Impurities (%) | EDTA (% w/v) | Sodium Benzoate (% w/v) | pH | Description |
|---|---|---|---|---|---|---|---|---|---|---|
| Time Zero | No nitrogen purging No nitrogen blanket | S-190626-00023 | 100.4 | 0.05 | ≤0.05 | 0.05 | 0.099 | 0.030 | 4.0 | Clear liquid |
| 7 days at 60° C. | No nitrogen purging | S-190701-00010 | 100.1 | 0.51 | ≤0.05 | 0.51 | 0.064 | 0.030 | 4.1 | Clear liquid |
| 15 days at 60° C. | No nitrogen blanket | S-190708-00040 | 100.1 | 0.68 | ≤0.05 | 0.68 | 0.045 | 0.030 | 4.2 | Clear liquid |
| 7 days at 60° C. | 10 sec nitrogen purging | S-190701-00011 | 100.5 | 0.41 | ≤0.05 | 0.41 | 0.073 | 0.030 | 4.0 | Clear liquid |
| 15 days at 60° C. | No nitrogen blanket | S-190708-00043 | 100.5 | 0.55 | ≤0.05 | 0.55 | 0.058 | 0.030 | 4.1 | Clear liquid |
| 7 days at 60° C. | No nitrogen purging | S-190701-00012 | 99.9 | 0.39 | ≤0.05 | 0.39 | 0.074 | 0.030 | 4.0 | Clear liquid |
| 15 days at 60° C. | 10 sec nitrogen blanket | S-190708-00041 | 100.9 | 0.44 | ≤0.05 | 0.44 | 0.069 | 0.030 | 4.1 | Clear liquid |
| 7 days at 60° C. | 10 sec nitrogen purging | S-190701-00013 | 100.5 | 0.34 | ≤0.05 | 0.34 | 0.079 | 0.030 | 4.0 | Clear liquid |
| 15 days at 60° C. | 10 sec nitrogen blanket | S-190708-00042 | 100.3 | 0.42 | ≤0.05 | 0.42 | 0.070 | 0.030 | 4.1 | Clear liquid |
| Specifications | Appearance: Clear Liquid; pH:2,0-5.0 Assay: 90.0%-110.0%; Impurities: Impurity A NMT 5.0%, Any Unidentified Impurity: NMT 0.10%; Total Impurities: NMT 7.0 910; Sodium Benzoate Content: 30 mg/ml: 0.015%-0.045% w/v (As labeled 50.0%-150%); 100 mg/ml: 0.050%-0.150% w/v (As labeled 50.0%-150%); EDTA Content: 0.010 to 0.150% w/v | | | | | | | | | |

UD—Undefined

Purging (nitrogen flush prior to product filling) and blanketing (nitrogen flush in the headspace after product filling) the bottles with nitrogen independently or concurrently during packaging of the product led to a reduction in the DO levels. The maximum reduction in DO levels was achieved when both purging and blanketing were used during packaging. The results for analytical testing showed that impurity A and total impurities were the lowest and % EDTA content was the highest for samples that were purged and blanketed in comparison to those that were either purged or blanketed with nitrogen. However, it was also noticed that results for DO levels, impurity A, total impurities, and % EDTA were only slightly lower for the bottles that were only blanketed. These results demonstrated that the DO levels and CQAs of the product were predominantly controlled by blanketing.

Based on the obtained results, nitrogen purging and blanketing for 10 seconds each, at a flow rate of 60 SL/min and 10 L/min, respectively, was found advantageous for packaging of the product at both 30 mg/ml and 100 mg/mL chlorpromazine hydrochloride strengths.

TABLE 79

Proposed packaging process parameters for Chlorpromazine Hydrochloride Oral Concentrate, USP, 30 mg/ml and 100 mg/mL

| Parameter | Description |
|---|---|
| Nitrogen Flow Rate (for purging) | 60 SL/min |
| Purging Time | 10 seconds |
| Nitrogen Flow Rate (for blanketing) | 10 L/min |
| Blanket Time | 10 seconds |
| Induction Sealer Power Setting | 35% |

As shown in Table 77, the average DO level at a purge time and blanket time of 10 seconds each was 5.15 mg/L. The DO levels of product packaged during PPQ batches will be measured by sampling packaged bottles at regular intervals, and the purging and blanketing processes will be verified by ensuring that the DO levels of the product in the packaged bottles is 58 mg/L. A specification of <8 mg/L was set since the DO levels for bottles that were not exposed to nitrogen were consistently above 8 mg/L.

The results of the dissolved oxygen levels of the finished product samples withdrawn during the PPQ batches showed that the nitrogen purging and blanketing (headspace purging) the bottles for 10 seconds at a rate of 60 SL/min and 10 L/min, respectively, resulted in acceptable DO levels that consistently met the specifications. Table 80 below shows the results of the CQAs of samples of the process validation batches that were not purged or blanketed with nitrogen prior to or during packaging. The results up to 3 months under accelerated conditions show that the CQAs for these samples comfortably meet specifications even in the absence of nitrogen blanketing or purging. Therefore, it was concluded that if the nitrogen purging and blanketing rate and duration are fixed, measurement of dissolved oxygen during commercial batches is not necessary as it is unlikely that the product attributes will be outside the acceptance limits even without nitrogen purging or blanketing.

manufacturing was not considered to further reduce the levels of dissolved oxygen. Additionally, the product did not exhibit any discoloration upon storage, even in the absence of the nitrogen blanket.

TABLE 80

Results of the Samples of Stability Batches Packaged without Nitrogen Purging or Blanketing after Storage Under Various Environmental Conditions

| Sampling Time Point | Condition | Appearance | pH | Assay (%) | EDTA Content (% LC) | Sodium Benzoate Content (% LC) | Impurities (%) A | UD | Total |
|---|---|---|---|---|---|---|---|---|---|
| Batch # S24319 (30 mg/mL) | | | | | | | | | |
| Packaging | Bottle Configuration: 120 cc PET; Bottles were not purged with nitrogen but were induction sealed | | | | | | | | |
| 0 Hour | NA | clear liquid, | 3.9 | 101.0 | 99.0 | 99.2 | <0.05 | <0.05 | <0.05 |
| 7 Days | 60° C. | clear liquid, | 4.2 | 98.8 | 46.9 | 99.8 | 0.60 | <0.05 | 0.60 |
| 15 Days | 60° C. | clear liquid, | 4.2 | 94.2 | 41.3 | 101.8 | 0.64 | <0.05 | 0.64 |
| 1 Month | 40° C./NMT25% RH | clear liquid, | 4.1 | 101.4 | 65.7 | 100.6 | 0.44 | <0.05 | 0.44 |
| 2 Months | 40° C./NMT25% RH | clear liquid, | 4.1 | 100.7 | 54.7 | 102.4 | 0.51 | <0.05 | 0.51 |
| 3 Months | 40° C./NMT25% RH | clear liquid, | 4.1 | 100.8 | 48.9 | 100.7 | 0.64 | <0.05 | 0.64 |
| 3 Mouths | 25° C./40% RH | clear liquid, | 3.9 | 100.2 | 88.7 | 98.7 | 0.28 | <0.05 | 0.28 |
| Batch # 524100119 (100 mg/mL) | | | | | | | | | |
| Packaging | Bottle Configuration: 240 cc PET; Bottles were not purged with nitrogen but were induction sealed | | | | | | | | |
| 0 Hour | NA | clear liquid, | 3.9 | 100.6 | 99.4 | 99.5 | <0.05 | <0.05 | <0.05 |
| 7 Days | 60° C. | clear liquid, | 4.0 | 99.5 | 69.9 | 102.0 | 0.14 | <0.05 | 0.14 |
| 15 Days | 60° C. | clear liquid, | 4.1 | 98.5 | 58.0 | 99.3 | 0.19 | <0.05 | 0.19 |
| 1 Month | 40° C./NMT25% RH | clear liquid, | 4.0 | 101.0 | 71.9 | 98.7 | 0.14 | <0.05 | 0.14 |
| 2 Months | 40° C./NMT25% RH | clear liquid, | 3.7 | 99.8 | 62.5 | 100.5 | 0.18 | <0.05 | 0.18 |
| 3 Mouths | 40° C./NMT25% RH | clear liquid, | 3.8 | 101.3 | 61.4 | 100.1 | 0.17 | <0.05 | 0.17 |
| 3 Months | 25° C./40% RH | clear liquid, | 3.9 | 99.9 | 89.3 | 100.5 | 0.08 | <0.05 | 0.08 |
| Acceptance Criteria | Appearance | Clear Liquid | | | | | | | |
| | pH | 2.0-5.0 | | | | | | | |
| | Assay | 90.0%-110.0% | | | | | | | |
| | Impurities | Impurity A NMT 5.0%, Any Unidentified Impurity: NMT 0.10%; Total impurities: NMT 7.0% | | | | | | | |
| | Sodium Benzoate Content | 30 mg/ml: 0.015%-0.045% w/v (As labeled 50.0%-150%) 100 mg/ml: 0.050%-0.150% w/v (As labeled 50.0%-150%) | | | | | | | |
| | EDTA Content | 0.010 to 0.150% w/v | | | | | | | |

UD—Unidentified,
ND—Not Detected,
NMT—Not More Than,
NA—Not Available

The manufacturing and packaging processes for the composition including 100 mg/mL chlorpromazine hydrochloride may be identical to the processes for the composition including 30 mg/mL chlorpromazine hydrochloride. During the product development studies it was observed that the DO levels for the compositions including 100 mg/mL chlorpromazine hydrochloride are generally lower than for compositions including 30 mg/mL chlorpromazine hydrochloride. Consequently, the impurity levels for the 100 mg/mL strength composition observed during accelerated stability studies are considerably lower than those for the 30 mg/mL composition. Therefore, identical purging and blanketing times with nitrogen were considered acceptable for the packaging of the 100 mg/mL strength PPQ batches.

The hold time study results demonstrated that the bulk liquid stored without nitrogen for a period of up to 30 days had slightly higher impurity levels in comparison to those under nitrogen blanket; however, the levels were significantly under the specification limits. Since the product met the stability specifications, sparging with nitrogen during Results from the evaluation of nitrogen purging/blanketing flow rate and duration showed that samples from containers that were not nitrogen purged or blanketed with nitrogen also met specifications after 15 days of storage at 60° C. and 3 months at accelerated stability conditions. However, the levels of impurities were much lower and EDTA content was relatively higher for samples purged and or blanketed with nitrogen. Accelerated stability studies (40° C./75% RH) for 6 months during formulation development already showed that the results comfortably met the specifications. In spite of acceptable stability in the absence of nitrogen, nitrogen purging and blanketing was included as a precautionary measure to prevent product discoloration and to limit the impurity levels. The nitrogen purging flow rate and duration were defined with experimental evaluation. The corresponding dissolved oxygen levels were determined and specifications for dissolved oxygen levels at time zero were established for process performance qualification batches.

Based on the product and process understanding gained throughout development and process parameter ranges established during process optimization, stability/PPQ (process performance qualification) batches were manufactured. The final batch formulae for the compositions including 30 mg/mL and 100 mg/mL chlorpromazine hydrochloride is the same as that used for the verification batches. The formulae are given in Table 62 and Table 63. The holding tank was purged with nitrogen before and after transferring the bulk drug product liquid as described herein. The bottles for primary packaging were purged with nitrogen before and after filling the product with the purging parameters defined during process optimization. The level of dissolved oxygen in the bottles was measured to ensure that the bottles were consistently purged with a sufficient amount of nitrogen. The equipment and process parameters were as defined during the process optimization batches.

A summary of the drug product tests, analytical procedures, acceptance limits, and results for the PPQ/stability batches for finished product testing results are summarized in Tables 81 and 82.

TABLE 81

Release Testing for Packaged Product-Chlorpromazine
Hydrochloride Oral Concentrate, USP, 30 mg/mL
Packaging Samples

| | Batch Lot Number | | |
|---|---|---|---|
| Test | 1 | 2 | 3 |
| Description | Meets Specification | Meets Specification | Meets Specification |
| Container closure | Meets Specification | Meets Specification | Meets Specification |
| Identification A: HPLC | Meets Specification | Meets Specification | Meets Specification |
| pH | 3.9 | 3.9 | 3.9 |
| Assay: HPLC | 98.4% | 101.5% | 101.4% |
| Preservative Content: Sodium Benzoate (Label Claim) | 0.030% w/v (101%) | 0.030% w/v (100%) | 0.030% w/v (99%) |
| Edetate Disodium Content (Label Claim) | 0.096% w/v (96%) | 0.099% w/v (99%) | 0.097% w/v (97%) |
| Deliverable Volume | Meets Specification | Meets Specification | Meets Specification |
| Microbial Limits: | | | |
| Total Aerobic Microbial Count | <10 cfu/g | <10 cfu/g | <10 cfu/g |
| Total Mold and Yeast Count | <10 cfu/g | <10 cfu/g | <10 cfu/g |
| Escherichia coli | Absent | Absent | Absent |
| Burkholderia cepacia | Absent | Absent | Absent |
| Specifications | | | |
| Description | Clear Liquid | | |
| Container Closure | No damage to the container closure and no leakage of the product detected. | | |
| Identification A: HPLC | The retention time of the chlorpromazine Hydrochloride peak in the sample chromatogram corresponds to that of the standard as determined in the Assay. | | |
| pH | Between 2.0-5.0 | | |
| Assay: HPLC | 90.0%-110.0% | | |
| Preservative Content: Sodium Benzoate | 30 mg/mL | 0.015% w/v-0.045% w/v (50%-150% of the labeled amount) | |
| Edetate Disodium Content | 0.050% w/v-0.150% w/v (50%-150% of the Label Claim) | | |
| Deliverable Volume | Meets the acceptance criteria for USP <698> for multiple dose containers | | |
| Microbial Limits: | | | |
| Total Aerobic Microbial Count | NMT 100 cfu/g | | |
| Total Mold and Yeast Count | NMT 10 cfu/g | | |
| Escherichia coli | Absent | | |
| Burkholderia cepacia | Absent | | |

TABLE 82

Release Testing for Packaged Product-Chlorpromazine
Hydrochloride Oral Concentrate, USP, 100 mg/mL
Packaging Samples

| | Genus Lot Number | | |
|---|---|---|---|
| Test | 11 | 12 | 13 |
| Description | Meets Specification | Meets Specification | Meets Specification |
| Container Closure | Meets Specification | Meets Specification | Meets Specification |
| Identification A: HPLC | Meets Specification | Meets Specification | Meets Specification |
| pH | 3.9 | 3.9 | 3.9 |
| Assay: HPLC | 100.9% | 101.5% | 100.6% |
| Preservative Content: Sodium Benzoate (Label Claim) | 0.099% w/v (99%) | 0.100% w/v (100%) | 0.100% w/v (100%) |
| Edetate Disodium Content (Label Claim) | 0.097% w/v (97%) | 0.098% w/v (98%) | 0.098% w/v (98%) |

TABLE 82-continued

Release Testing for Packaged Product-Chlorpromazine
Hydrochloride Oral Concentrate, USP, 100 mg/mL
Packaging Samples

| | Genus Lot Number | | |
|---|---|---|---|
| Test | 11 | 12 | 13 |
| Deliverable Volume | Meets Specification | Meets Specification | Meets Specification |
| Microbial Limits: | | | |
| Total Aerobic Microbial Count | <10 cfu/g | <10 cfu/g | <10 cfu/g |
| Total Mold and Yeast Count | <10 cfu/g | <10 cfu/g | <10 cfu/g |
| *Escherichia coli* | Absent | Absent | Absent |
| *Burkholderia cepacia* | Absent | Absent | Absent |
| | Specifications | | |
| Description | Clear Liquid | | |
| Container Closure | No damage to the container closure and no leakage of the product detected. | | |
| Identification A: HPLC | The retention time of the chlorpromazine Hydrochloride peak in the sample chromatogram corresponds to that of the standard as determined in the Assay. | | |
| pH | Between 2.0-5.0 | | |
| Assay: HPLC | 90.0%-110.0% | | |
| Preservative Content: Sodium Benzoate | 100 mg/mL | 0.050% w/v-0.150% w/v (50%-150% of the labeled amount) | |
| Edetate Disodium Content | 0.050% w/v-0.150% w/v (50%-150% of the Label Claim) | | |
| Deliverable Volume | Meets the acceptance criteria for USP <698> for multiple dose containers | | |
| Microbial Limits: | | | |
| Total Aerobic Microbial Count | NMT 100 cfu/g | | |
| Total Mold and Yeast Count | NMT 10 cfu/g | | |
| *Escherichia coli* | Absent | | |
| *Burkholderia cepacia* | Absent | | |

Mixing speed and time were optimized during process development. The results for CQAs were found to be consistent across the established range during process optimization. The CQAs were also found to be consistent and met the specifications for the process performance qualification batches.

The results for the CQAs of the samples taken from the beginning, middle, and end of the filtration process for all the process optimization and process performance qualification batches were found to be consistent and within specifications. There was no change in the pH, decrease in the assay values, or increase in the level of impurities. The type and pore size of the filter were fixed.

The hold time studies demonstrated that the product met the specifications even in the absence of nitrogen blanket during storage. There was a minor increase in the level of impurities for the product held without the nitrogen blanket; however, the impurities were still significantly under the respective limits. Although the hold time results without a nitrogen blanket are acceptable, the tank may be purged with nitrogen before and after filling to minimize potential oxidative degradation. The rate and duration of nitrogen purge was fixed.

The process optimization studies showed that the packaged product met specifications even in the absence of nitrogen purging. However, the level of impurity A was relatively higher and the EDTA content was relatively lower for bottles without nitrogen in comparison to those purged with nitrogen. Therefore, to avoid the risk of discoloration due to consumption of EDTA in the product during long term storage, the bottles may be purged with nitrogen before and after the product is filled.

Example 17

Typically, liquid oral chlorpromazine compositions are sold as concentrates that are diluted prior to administration to a subject. Thus, the size of the storage container can be selected such that additional liquid can be added to the liquid oral composition. However, the inventors determined that the additional headspace may lead to increased oxidation of the chlorpromazine. Thus, the following example was performed to determine the optimal headspace for a container to store the liquid oral compositions. The compositions of the tested batches is provided in Tables 83 and 84. The results of bottle size on the generation of impurity A are shown in Table 85.

TABLE 83

Composition for Batches NB538-0052 and NB538-0054

| Weight/Volume (mg/mL) | Component |
|---|---|
| 100.000 | Chlorpromazine Hydrochloride |
| 3.000 | Sucralose, USP |
| 1.000 | Sodium Benzoate, NF |
| 5.220 | Sodium Citrate Dihydrate, USP |
| 3.393 | Citric Acid Anhydrous, USP |
| 0.500 | Ascorbic Acid |
| 0.062 | FD&C Yellow #6 |
| qs | Purified Water, USP |
| qs to 1 mL | Total |

TABLE 84

Composition for Batch N9538-0055

| Weight/Volume (mg/mL) | Component |
|---|---|
| 100.000 | Chlorpromazine Hydrochloride |
| 3.000 | Sucralose, USP |
| 1.000 | Sodium Benzoate, NF |

TABLE 84-continued

Composition for Batch N9538-0055

| Weight/Volume (mg/mL) | Component |
|---|---|
| 5.220 | Sodium Citrate Dihydrate, USP |
| 3.393 | Citric Acid Anhydrous, USP |
| qs | Purified Water, USP |
| qs to 1 mL | Total |

TABLE 85

Effect of Headspace on Stability-Stability Increases with Decrease in Headspace

| Batch | Bottle Size (Fill Volume) | Time | Condition | Impurities (% w/w) A | B | D | E | Any UD | Total |
|---|---|---|---|---|---|---|---|---|---|
| NB538-052 | 500 mL | $T_0$ | NA | ND | ND | 0.06 | ND | ND | 0.06 |
|  | (Fill Volume: 30 mL) | 7 Days | 60° C. | 0.47 | ND | 0.05 | 0.04 | ND | 0.57 |
| NE538-054 | 60 mL | $T_0$ | NA | ND | ND | 0.06 | ND | ND | 0.06 |
|  | (Fill Volume: 30 mL) | 9 Days | 60° C. | 0.08 | ND | 0.06 | 0.05 | ND | 0.19 |
| NE538-055* | 60 mL | $T_0$ | NA | ND | ND | 0.06 | ND | ND | 0.06 |
|  | (Fill Volume 60 mL): | 9 Days | 60° C. | 0.05 | ND | 0.07 | ND | ND | 0.11 |

All bottles Packaged with Nitrogen Purge and Induction Seal
*Color and Ascorbic Acid were removed from the formulation and the rest of the formulation was the same as NB538-052 and NB538-054
*PET bottles were used for batch NB538-054 and NB538-055

Example 18

The following study was performed on Batches NB538-079 and NB538-080 to determine the effect of EDTA on the color of the solution during storage. The batches' compositions are provided in Tables 86 and 87. During the processing and stability studies of batches NB538-079 and NB538-080 the solution was seen to change color within 24 hours upon storage if it was not packaged immediately upon manufacturing. Therefore, EDTA (ethylenediaminetetraacetic acid) (chelating agent) was added to the formulation to prevent the complexation between chlorpromazine with metal ions which may be present in trace amounts as impurities in the excipients. Batches NB538-088 and NB538-089 (with EDTA) did not show any color change even after 6 months of storage under accelerated conditions 40° C./75% RH.

TABLE 86

Composition for Batch NB538-0079

| Weight/Volume (mg/mL) | Component |
|---|---|
| 30.000 | Chlorpromazine Hydrochloride |
| 9.000 | Sucralose, NF |
| 0.300 | Sodium Benzoate, NF |
| 1.566 | Sodium Citrate Dihydrate, USP |
| 1.018 | Citric Acid Anhydrous, USP |
| 968.116 | Purified Water, USP |
| 1010.000 | Total |

TABLE 87

Composition for Batch NB538-0080

| Weight/Volume (mg/mL) | Component |
|---|---|
| 100.000 | Chlorpromazine Hydrochloride |
| 30.000 | Sucralose, NF |
| 1.000 | Sodium Benzoate, NF |
| 5.220 | Sodium Citrate Dihydrate, USP |
| 3.393 | Citric Acid Anhydrous, USP |
| 898.387 | Purified Water, USP |
| 1038.000 | Total |

Example 19

The following example was performed to determine the effect of nitrogen purging and dissolved oxygen levels on the stability of liquid oral compositions including chlorpromazine. Batches NB-538-106 and NB538-107 as previously described herein were stored at various conditions and evaluated for impurities as shown in Table 88 below.

TABLE 88

Effect of Nitrogen Purging/Dissolved Oxygen Levels on Stability

| Batch | Time | Condition | Nitrogen Purging | Dissolved Oxygen Level | Assay | EDTA Content | Impurities (% w/w) A | Any UD | Total |
|---|---|---|---|---|---|---|---|---|---|
| NB538-106 | $T_0$ | NA | No | 9.49 | 100.7 | 98 | ≤0.05 | ≤0.05 | ≤0.05 |
| (100 mg/ml) | 15 Days | 60° C. | No | NA | 101.5 | 57 | 0.21 | ≤0.05 | 0.21 |
|  | 15 Days | 60° C. | Yes | 2 to 4.5 mg/L* | 101.2 | 89 | 0:08 | ≤ 0.05 | 0.08 |
| NB538-107 | $T_0$ | NA | No | 8.22 | 101.2 | 98 | ≤0.05 | ≤0.05 | ≤0.05 |
| (30 mg/ml) | 15 Days | 60° C. | No | NA | 102.1 | 40 | 0.71 | ≤0.05 | 0.71 |
|  | 15 Days | 60° C. | Yes | 2 to 4.5 mg/L* | 102.3 | 76 | 0.36 | ≤ 0.05 | 0.36 |

*Dissolved oxygen levels prior to initiation of stability studies

Example 20

The following study was performed to determine the effect of primary packaging on the stability of the compositions. Batches NB-538-057 as previously described herein and batch NB-538-051 (composition provided in Table 89 below) were stored at various conditions and evaluated for impurities as shown in Table 90 below.

TABLE 89

Composition for Batch NB538-0051

| Weight/Volume (mg/mL) | Component |
|---|---|
| 100.000 | Chlorpromazine Hydrochloride |
| 1.500 | Sucralose, NF |
| 1.000 | Sodium Benzoate, NF |
| 5.220 | Sodium Citrate Dihydrate, USP |
| 3.393 | Citric Acid Anhydrous, USP |
| 0.500 | Asorbic Acid |
| 0.062 | FD&C Yellow #6 |
| qs | Purified Water, USP |
| qs to 1 mL | Total |

TABLE 90

Effect of Primary Packaging (Material of Construction) on Stability—Stable Formulation with PET bottles

| Batch | Bottle Type | Time | Condition | Impurities (% w/w) A | B | D | E | Any UD | Total |
|---|---|---|---|---|---|---|---|---|---|
| N13538-051 | HDPE | T0 | NA | ND | ND | 0.06 | ND | ND | 0.06 |
|  |  | 7 Days | 60° C. | 0.47 | ND | 0.05 | 0.04 | ND | 0.57 |
| NE538-057 | PET | T0 | NA | ND | ND | 0.06 | ND | ND | 0.06 |
|  |  | 7 Days | 60° C. | 0.06 | ND | 0.07 | ND | ND | 0.13 |

Example 21

The following study was performed to determine the effect of the chlorpromazine concentration on the stability of the liquid oral compositions. Batches NB538-088 (100 mg/mL chlorpromazine) and NB528-089 (3 mg/mL chlorpromazine) as previously described herein were stored at various conditions and evaluated for impurities as shown in Table 91 below.

TABLE 91

Formulation with Impurity A <0.6% for 30 mg/mL and <0.2% for 100 mg/ml for the Intended Shelf Life of 2 Years

| Batch | Bottle Type | Time | Condition | Assay | Impurities (% w/w) A | UD | Total | % EDTA | Appearance |
|---|---|---|---|---|---|---|---|---|---|
| NB538-089 | PET | T0 | NA | 99.6 | ≤0.05 | ≤0.05 | ≤0.05 | NA | Clear |
| (30 mg/mL) |  | 6 M | 40° C./75% RH | 98.4 | 0.58 | ≤0.05 | 0.58 | 45 | Clear |
| NB5384088 | PET | T0 | NA | 98.9 | ≤0.05 | ≤0.05 | ≤0.05 | N/A | Clear |
| (100 mg/mL) |  | 6 M | 40° C./75% RH | 98.2 | 0.16 | ≤0.05 | 0.16 | 67 | Clear |

Parameters

A control strategy can be used to ensure consistent quality and comprises raw material controls, process controls, monitoring of individual or multiple unit operations, and final product specifications. For the oral liquid compositions according to the present disclosure, non-limiting examples of the excipients and commercial scale process along with the operation ranges for process parameters that may be used are provided in Table 92 and Table 93 below.

TABLE 92

Raw Material Control Strategy for Chlorpromazine
Hydrochloride Oral Concentrate, USP 30 mg/mL and 100 mg/mL

| Factor | Attribute/ Parameter | Range Studied/ Vendors Specifications | Result for the Stability/ PPQ Batches | | Proposed Operating Range for Commercial Scale | Purpose of Control |
|---|---|---|---|---|---|---|
| Input Material Attributes | | | | | | |
| Chlorpromazine Hydrochloride | Assay | 98.0 to 101.5% | Lot# 19-0102 19-0103 | Result 100.6 100.0 | NMI 0.1% | To ensure the API is within specification since the API is sensitive to oxidative and photolytic degradation |
| | Impurity A | NMT 0.1% | 19-0102 19-0103 | <0.05% <0.05% | | |
| | Total impurities (specified & unspecified) | NMT 1.0% | 19-0102 19-0103 | 0.06% 0.06% | NMT 1.0% | |
| | Melting Point | 195-198° C. | 19-0102 19-0103 | 197° C. 198° C. | 195-198° C. | To verify the polymorphic form |
| Sucralose, NF Sodium Benzoate, NF Titriplex III EDTA Disodium Salt Dihydrate, USP Sodium Citrate Dihydrate, USP Citric Acid Anhydrous, USP Purified Water USP Nitrogen, NF | | Current USP-NF monographs available for respective components | 18-0333 19-0112 19-0095 19-0128 19-0129 18-0339 19-0188 and 19-0193 | Respective lots meet the compendial specifications | Respective lots used meet the compendial monograph specifications | To meet finished product specifications |

TABLE 93

Process Control Strategy for Chlorpromazine Hydrochloride Oral Concentrate, USP 30 mg/mL and 100 mg/mL

| Factor | Attribute/Parameter | Range Studied | Result for the Stability/ PPQ Batches Batches | Proposed Operating Range for Commercial Scale | | | Purpose of Control |
|---|---|---|---|---|---|---|---|
| Melting Mixing and Dispersion of Ingredients Process Parameters | | | | | | | |
| Mixing Tank | | Strength (mg/ml) | Speed (RPM) | Strength (mg/ml) | Batch 1/2/3 Speed (RPM) | Strength (mg/ml) | Speed (RPM) | Ensure complete dissolution of ingredients |
| | Mixer Speed- Dissolution of Sucralose, Sodium Benzoate, Titriplex III EDTA Disodium Salt Dihydrate, Sodium Citrate Dihydrate, Citric Acid Anhydrous in Purified Water | 30 100 | 130-201 130-200 | 30 100 | 190/170/180 182/178/174 | 30 100 | 135-195 | |
| | Mixer Speed (Impeller Speed)-Dissolution of Chlorpromazine Hydrochloride | 30 100 100 | 130-200 130-200 | 30 100 | 191/173/183 182/173/176 | 30 100 | | |

TABLE 93-continued

Process Control Strategy for Chlorpromazine Hydrochloride Oral Concentrate, USP 30 mg/mL and 100 mg/mL

| Factor | Attribute/Parameter | Range Studied | Result for the Stability/PPQ Batches | | Proposed Operating Range for Commercial Scale | | Purpose of Control | | |
|---|---|---|---|---|---|---|---|---|---|
| | Mixing Time-Dissolution of Sucralose, Sodium Benzoate, Titriplex III EDTA Disodium Salt Dihydrate, Sodium Citrate Dihydrate, Citric Acid Anhydrous in Purified Water | | Strength (mg/ml) 30 | Time (min) 10-30 | Strength (mg/ml) 30 | Time (min) 28/26/25 | Strength (mg/ml) 30 | Time (min) 11-29 | |
| | | | 100 | 15-35 | 100 | 34/30/30 | 100 | 16-34 | |
| | Mixing Time-Dissolution of Chlorpromazine Hydrochloride | | 30 | 15-35 | 30 | :30/31/3:3 | 30 | 16-34 | |
| | | | 100 | 20-40 | 100 | 33/35/36 | 100 | 21-39 | |
| Holding Tank | Nitrogen Purging | 0-36 (min) at 50 scfh | 36 min at 50 scfh | | 36 min at 50 scfh | | | | Fixed to ensure product stability |
| | Nitrogen Blanket | 0-24 (min) at 50 scfh | 24 min at 50 scfh | | 24 min at 50 scfh | | | | |
| Packaging | Nitrogen Purging Time-Empty Bottle | 0 to 10 (sec) at SLPM | Value 60 for 10 seconds | | Result Dissolved Oxygen Level: <8 mg/L | | 60 SLPM for 10 seconds | | Ensure product stability upon long term storage |
| | Nitrogen Purging Time (Blanket)-Filled Bottle | 0 to 10 (see) at 10 LPM | 10 LPM for 10 seconds | | | | 10 LPM for 10 seconds | | |

The following numbered clauses are directed to various non-limiting aspects according to the present disclosure:

1. An oral liquid pharmaceutical composition comprising:
   about 25 mg/mL to about 35 mg/mL chlorpromazine or a pharmaceutically acceptable salt or solvate thereof;
   about 0.1 mg/mL to about 5 mg/mL sodium benzoate;
   about 0.5 mg/mL to about 5 mg/mL EDTA; and
   water;
   provided that the oral liquid pharmaceutical composition retains at least about 90% of an initial amount of chlorpromazine or pharmaceutically acceptable salt or solvate thereof after three months stored at a temperature ranging from about 38° C. to about 42° C. and a relative humidity ranging from about 70% to about 80%.

2. The oral liquid pharmaceutical composition of clause 1, provided that the oral liquid pharmaceutical composition retains at least about 95% of an initial amount of chlorpromazine or pharmaceutically acceptable salt or solvate thereof after three months stored at a temperature ranging from about 38° C. to about 42° C. and a relative humidity ranging from about 70% to about 80%.

3. The oral liquid pharmaceutical composition of any of clauses 1 and 2, provided that the oral liquid pharmaceutical composition retains at least about 95% of an initial amount of chlorpromazine or pharmaceutically acceptable salt or solvate thereof after six months stored at a temperature ranging from about 38° C. to about 42° C. and a relative humidity ranging from about 70% to about 80%.

4. The oral liquid pharmaceutical composition of any of clauses 1-3, provided that the oral liquid pharmaceutical composition contains less than 5% of impurity A after three months stored at a temperature ranging from about 38° C. to about 42° C. and a relative humidity ranging from about 70% to about 80%.

5. The oral liquid pharmaceutical composition of any of clauses 1-3, provided that the oral liquid pharmaceutical composition contains less than 1% of impurity A after three months stored at a temperature ranging from about 38° C. to about 42° C. and a relative humidity ranging from about 70% to about 80%.

6. The oral liquid pharmaceutical composition of any of clauses 1-5, provided that the oral liquid pharmaceutical composition is stored in a polyethylene terephthalate bottle.

7. An oral liquid pharmaceutical composition comprising:
   about 90 mg/mL to about 110 mg/mL chlorpromazine or a pharmaceutically acceptable salt or solvate thereof;
   about 0.1 mg/mL to about 5 mg/mL sodium benzoate;
   about 0.5 mg/mL to about 5 mg/mL EDTA; and
   water;
   provided that the oral liquid pharmaceutical composition retains at least about 90% of an initial amount of chlorpromazine or pharmaceutically acceptable salt or solvate thereof after three months stored at a temperature ranging from about 38° C. to about 42° C. and a relative humidity ranging from about 70% to about 80%.

8. The oral liquid pharmaceutical composition of clause 7, provided that the oral liquid pharmaceutical composition retains at least about 95% of an initial amount of chlorpromazine or pharmaceutically acceptable salt or solvate thereof after three months stored at a temperature ranging from about 38° C. to about 42° C. and a relative humidity ranging from about 70% to about 80%.

9. The oral liquid pharmaceutical composition of any of clauses 7 and 8, provided that the oral liquid pharmaceutical composition retains at least about 95% of an initial amount of chlorpromazine or pharmaceutically acceptable salt or solvate thereof after six months stored at a temperature ranging from about 38° C. to about 42° C. and a relative humidity ranging from about 70% to about 80%.

10. The oral liquid pharmaceutical composition of any of clauses 7-9, provided that the oral liquid pharmaceutical composition contains less than 5% of impurity A after three months stored at a temperature ranging from about 38° C. to about 42° C. and a relative humidity ranging from about 70% to about 80%.

11. The oral liquid pharmaceutical composition of any of clauses 7-9, provided that the oral liquid pharmaceutical composition contains less than 1% of impurity A after three months stored at a temperature ranging from about 38° C. to about 42° C. and a relative humidity ranging from about 70% to about 80%.

12. The oral liquid pharmaceutical composition of any of clauses 7-11, provided that the oral liquid pharmaceutical composition is stored in a polyethylene terephthalate bottle.

What is claimed is:

1. An oral liquid pharmaceutical composition comprising:
about 25 mg/mL to about 35 mg/mL chlorpromazine or a pharmaceutically acceptable salt or solvate thereof;
about 0.1 mg/mL to about 5 mg/mL sodium benzoate;
about 0.5 mg/mL to about 5 mg/mL EDTA; and
water;
provided that a pH of the oral liquid pharmaceutical composition is about 3.0 to about 5.0.

2. The oral liquid pharmaceutical composition of claim 1, provided that the oral liquid pharmaceutical composition comprises less than 5% of chlorpromazine sulfoxide after three months stored at a temperature ranging from about 38° C. to about 42° C. and a relative humidity ranging from about 70% to about 80%.

3. The oral liquid pharmaceutical composition of claim 1, provided that the oral liquid pharmaceutical composition contains less than 1% of chlorpromazine sulfoxide after three months stored at a temperature ranging from about 38° C. to about 42° C. and a relative humidity ranging from about 70% to about 80%.

4. The oral liquid pharmaceutical composition of claim 1, provided that the pH of the oral liquid pharmaceutical composition is about 3.5 to about 4.5.

5. The oral liquid pharmaceutical composition of claim 1, further comprising about 0.1 mg/mL to about 4 mg/mL citric acid.

6. The oral liquid pharmaceutical composition of claim 1, further comprising about 0.5 mg/mL to about 7 mg/mL sodium citrate.

7. The oral liquid pharmaceutical composition of claim 1, provided that the oral liquid pharmaceutical composition is stored in a polyethylene terephthalate bottle.

8. The oral liquid pharmaceutical composition of claim 1 comprising:
about 25 mg/mL to about 35 mg/mL chlorpromazine or a pharmaceutically acceptable salt or solvate thereof;
about 0.1 mg/mL to about 5 mg/mL sodium benzoate;
about 0.5 mg/mL to about 5 mg/mL EDTA;
about 0.1 mg/mL to about 4 mg/mL citric acid;
about 0.5 mg/mL to about 7 mg/mL sodium citrate; and
water;
provided that a pH of the oral liquid pharmaceutical composition is about 3.0 to about 5.0.

9. The oral liquid pharmaceutical composition of claim 8, provided that the oral liquid pharmaceutical composition comprises less than 5% of chlorpromazine sulfoxide after three months stored at a temperature ranging from about 38° C. to about 42° C. and a relative humidity ranging from about 70% to about 80%.

10. The oral liquid pharmaceutical composition of claim 8, provided that the oral liquid pharmaceutical composition contains less than 1% of chlorpromazine sulfoxide after three months stored at a temperature ranging from about 38° C. to about 42° C. and a relative humidity ranging from about 70% to about 80%.

11. The oral liquid pharmaceutical composition of claim 8, provided that the pH of the oral liquid pharmaceutical composition is about 3.5 to about 4.5.

12. An oral liquid pharmaceutical composition comprising:
about 90 mg/mL to about 110 mg/mL chlorpromazine or a pharmaceutically acceptable salt or solvate thereof;
about 0.1 mg/mL to about 5 mg/mL sodium benzoate;
about 0.5 mg/mL to about 5 mg/mL EDTA; and
water;
provided that a pH of the oral liquid pharmaceutical composition is about 3.0 to about 5.0.

13. The oral liquid pharmaceutical composition of claim 12, provided that the oral liquid pharmaceutical composition comprises less than 5% of chlorpromazine sulfoxide after three months stored at a temperature ranging from about 38° C. to about 42° C. and a relative humidity ranging from about 70% to about 80%.

14. The oral liquid pharmaceutical composition of claim 12, provided that the oral liquid pharmaceutical composition contains less than 1% of chlorpromazine sulfoxide after three months stored at a temperature ranging from about 38° C. to about 42° C. and a relative humidity ranging from about 70% to about 80%.

15. The oral liquid pharmaceutical composition of claim 12, provided that the pH of the oral liquid pharmaceutical composition is about 3.5 to about 4.5.

16. The oral liquid pharmaceutical composition of claim 12, further comprising about 0.05 mg/mL to about 5 mg/mL citric acid.

17. The oral liquid pharmaceutical composition of claim 12, further comprising about 0.5 mg/mL to about 7 mg/mL sodium citrate.

18. The oral liquid pharmaceutical composition of claim 12, provided that the oral liquid pharmaceutical composition is stored in a polyethylene terephthalate bottle.

19. The oral liquid pharmaceutical composition of claim 12 comprising:
about 25 mg/mL to about 35 mg/mL chlorpromazine or a pharmaceutically acceptable salt or solvate thereof;
about 0.1 mg/mL to about 5 mg/mL sodium benzoate;
about 0.5 mg/mL to about 5 mg/mL EDTA;
about 0.05 mg/mL to about 5 mg/mL citric acid;
about 0.5 mg/mL to about 7 mg/mL sodium citrate; and
water;
provided that a pH of the oral liquid pharmaceutical composition is about 3.0 to about 5.0.

20. The oral liquid pharmaceutical composition of claim 19, provided that the oral liquid pharmaceutical composition comprises less than 5% of chlorpromazine sulfoxide after three months stored at a temperature ranging from about 38° C. to about 42° C. and a relative humidity ranging from about 70% to about 80%.

21. The oral liquid pharmaceutical composition of claim 19, provided that the oral liquid pharmaceutical composition contains less than 1% of chlorpromazine sulfoxide after three months stored at a temperature ranging from about 38° C. to about 42° C. and a relative humidity ranging from about 70% to about 80%.

22. The oral liquid pharmaceutical composition of claim 19, provided that the pH of the oral liquid pharmaceutical composition is about 3.5 to about 4.5.

23. A method for treating a medical condition, the method comprising administering a therapeutically effective amount of the oral liquid pharmaceutical composition of claim 1 to a human subject in need thereof, wherein the medical condition is selected from the group consisting of: a manifestation of a psychotic disorder; nausea and vomiting; restlessness and apprehension before surgery; acute intermittent *porphyria*; tetanus; a manifestation of a manic type manic-depressive illness; intractable hiccups; and a severe behavioral problem in a child 1 to 12 years of age.

24. A method for treating a medical condition, the method comprising administering a therapeutically effective amount of the oral liquid pharmaceutical composition of claim 12 to a human subject in need thereof, wherein the medical condition is selected from the group consisting of: a manifestation of a psychotic disorder; nausea and vomiting; restlessness and apprehension before surgery; acute intermittent *porphyria*; tetanus; a manifestation of a manic type manic-depressive illness; intractable hiccups; and a severe behavioral problem in a child 1 to 12 years of age.

\* \* \* \* \*